(12) United States Patent
Shimizu

(10) Patent No.: US 12,426,816 B2
(45) Date of Patent: Sep. 30, 2025

(54) EMOTION ASSESSMENT APPARATUS, EMOTION ASSESSMENT METHOD AND EMOTION ASSESSMENT PROGRAM

(71) Applicant: CITIZEN WATCH CO., LTD., Nishitokyo (JP)

(72) Inventor: Hideki Shimizu, Tokyo (JP)

(73) Assignee: CITIZEN WATCH CO., LTD., Tokyo (JP)

( * ) Notice: Subject to any disclaimer, the term of this patent is extended or adjusted under 35 U.S.C. 154(b) by 364 days.

(21) Appl. No.: 18/246,503

(22) PCT Filed: Sep. 24, 2021

(86) PCT No.: PCT/JP2021/035163
§ 371 (c)(1),
(2) Date: Mar. 23, 2023

(87) PCT Pub. No.: WO2022/065446
PCT Pub. Date: Mar. 31, 2022

(65) Prior Publication Data
US 2023/0363680 A1    Nov. 16, 2023

(30) Foreign Application Priority Data
Sep. 24, 2020   (JP) .............................. 2020-159837

(51) Int. Cl.
*A61B 5/16* (2006.01)
*A61B 5/024* (2006.01)
*G06V 40/16* (2022.01)

(52) U.S. Cl.
CPC .......... *A61B 5/165* (2013.01); *A61B 5/02427* (2013.01); *G06V 40/172* (2022.01); *G06V 40/174* (2022.01); *A61B 2503/12* (2013.01)

(58) Field of Classification Search
None
See application file for complete search history.

(56) References Cited

U.S. PATENT DOCUMENTS

| | | | |
|---|---|---|---|
| 2017/0238859 A1* | 8/2017 | Sadowsky | G16H 50/20 |
| 2019/0269361 A1* | 9/2019 | Shimizu | A61B 5/7475 |
| 2020/0099890 A1 | 3/2020 | Tanaka et al. | |

FOREIGN PATENT DOCUMENTS

| | | |
|---|---|---|
| EP | 3263024 A1 | 1/2018 |
| JP | 2005-198828 A | 7/2005 |

(Continued)

OTHER PUBLICATIONS

WIPO, International Search Report for International Application No. PCT/JP2021/035163, Dec. 14, 2021.

(Continued)

*Primary Examiner* — Leon Viet Q Nguyen

(57) ABSTRACT

The emotion assessment apparatus has a detecting unit detecting heartbeat information including the heart rate of a subject, an emotion assessment unit assessing whether the emotion of the subject is a negative emotion or a positive emotion based on the heartbeat information, a counting unit counting the number of heart rate variations within a predetermined time period, an emotional expression assessment unit assessing the mental state of the subject based on the number of heart rate variations, and using the assessment results from the emotion assessment unit to assess the mental state, and an output unit outputting the assessment results from the emotional expression assessment unit.

15 Claims, 34 Drawing Sheets

(56) References Cited

FOREIGN PATENT DOCUMENTS

| | | |
|---|---|---|
| JP | 2005-311915 A | 11/2005 |
| JP | 2019-130344 A | 8/2019 |
| JP | 2020-48149 A | 3/2020 |
| JP | 2020-126645 A | 8/2020 |

OTHER PUBLICATIONS

WIPO, International Preliminary Report on Patentability, including Written Opinion for International Application No. PCT/JP2021/035163, Dec. 14, 2021.

* cited by examiner

FIG. 25

| Compatibility | Image stimulus | Sound stimulus |
|---|---|---|
| Vision/hearing | Images of specific caregiver | Voice audio of specific caregiver |
| Mental illness | Images of colors alone | Beat sound at specific frequency |
| | Illusion picture image, scary image without color stimulus | Meaningful words |

FIG. 33

| | | Reaction to first stimulus for vision /hearing assessment | Reaction to second stimulus for mental illness assessment | Reaction to third stimulus for compatibility assessment |
|---|---|---|---|---|
| Normal | Image reaction | Yes | Yes | No/yes and positive reaction |
| | Sound reaction | Yes | Yes | No/yes and positive reaction |
| Mental abnormality assessment example | Image reaction | Yes | No | No/yes and positive reaction |
| | Sound reaction | Yes | No | No/yes and positive reaction |
| Auditory abnormality assessment example | Image reaction | Yes | Yes | No/yes and positive reaction |
| | Sound reaction | No | No/yes | No/yes and positive reaction |
| Visual abnormality assessment example | Image reaction | No | No/yes | No/yes and positive reaction |
| | Sound reaction | Yes | Yes | No/yes and positive reaction |
| Compatibility assessment example | Image reaction | Yes | Yes | Yes and negative reaction |
| | Sound reaction | Yes | Yes | Yes and negative reaction |

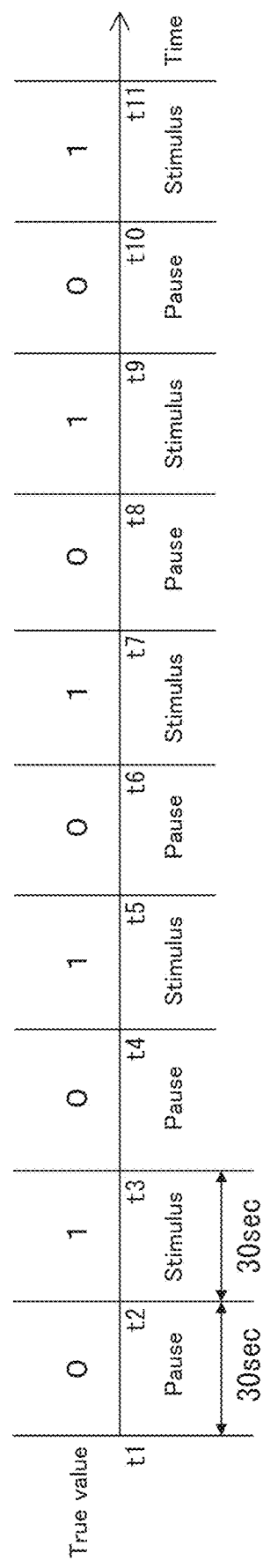
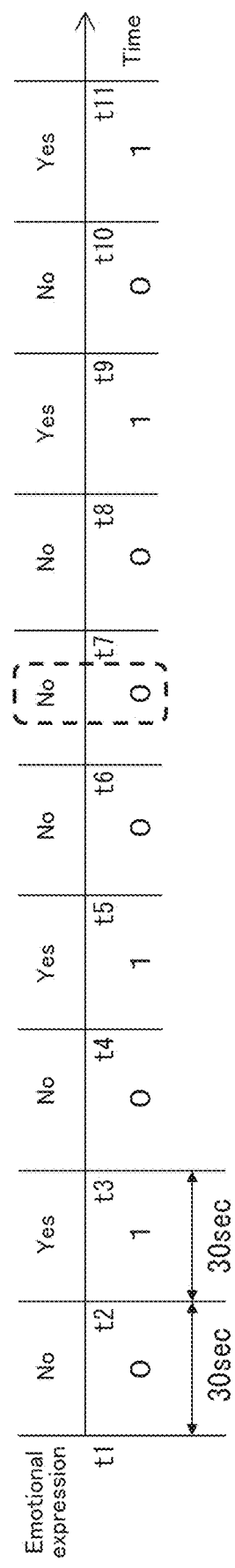
FIG. 34A
FIG. 34B

EMOTION ASSESSMENT APPARATUS, EMOTION ASSESSMENT METHOD AND EMOTION ASSESSMENT PROGRAM

FIELD

The present invention relates to an emotion assessment apparatus, an emotion assessment method and an emotion assessment program for assessment of the emotion of a subject.

BACKGROUND

At facilities where elderly persons receive care, it is extremely important for caregivers who provide the care to be able to discern the emotional state of the elderly, in order to formulate future caregiving policy. However, elderly persons often exhibit subdued facial expression due to their age and may also be difficult to converse with, making it difficult for their emotions to be discerned from their facial expressions, atmosphere or conversational content.

In general video communications or video conferencing as well, for conversations to proceed smoothly it is extremely important for each speaker to discern the emotions of listeners in response to the words spoken by the speaker. However, because images showing the facial expressions of listeners during video conferences are limited to images taken by cameras, it has been problematically difficult to discern the emotions of listeners from their facial expressions and atmosphere. Conferencing using monitors via communication lines is generally referred to as either "video conferencing" or "web conferencing", depending on the situation, and although other terms are sometimes used, the term "web conferencing" will be used throughout the present specification.

PTL 1 discloses a communication device comprising emotion analyzing means that analyzes the emotions of another party during communication, storing means that stores emotion data analyzed by the emotion analyzing means and corresponding to the other party whose emotions were analyzed, notification means that gives a notification based on the emotion data stored in the storing means, and control means that reads the emotion data corresponding to the other party from the storing means when the other party has been selected, and causes the notification means to provide a notification.

PTL 2 discloses an image processing device comprising an image data acquisition unit that acquires image data taken of multiple conference participants, a facial image detector that detects the facial images of each conference participant from image data acquired by the image data acquisition unit, an image compositing unit that cuts out detected facial images and composites them into one image, an emotion estimating unit that estimates the emotion of each participant based on the detected facial images, and a display mode switching unit that switches the display mode for the facial images of each participant based on the estimated emotion.

Since the invention described in PTL 1 analyzes the voices of communicating parties and assesses their emotions, it requires the other parties to speak and is therefore not applicable for minimally talkative participants or for conference listeners. The invention described in PTL 2 estimates facial expressions from facial images of conference participants and estimates their emotions based on the estimated facial expressions, but has difficulty estimating the emotions of participants with few facial expressions.

CITATION LIST

Patent Literature

[PTL 1] Japanese Unexamined Patent Publication No. 2005-311915

[PTL 2] Japanese Unexamined Patent Publication No. 2020-48149

SUMMARY

It is an object of the present invention to provide an emotion assessment apparatus, emotion assessment method and emotion assessment program that allow contactless detection of the emotions of other parties.

The emotion assessment apparatus according to one embodiment of the disclosure has a detecting unit detecting heartbeat information including the heart rate of a subject, an emotion assessment unit assessing whether the emotion of the subject is a negative emotion or a positive emotion based on the heartbeat information, a counting unit counting the number of heart rate variations within a predetermined time period, the heart rate variations being transitions from a state in which the heart rate is below the average heart rate to a state in which the heart rate is greater than or equal to the average heart rate and being with heart rate increase greater than or equal to a predetermined value, an emotional expression assessment unit assessing the mental state of the subject based on the number of heart rate variations, and using the assessment results from the emotion assessment unit to assess the mental state, and an output unit outputting the assessment results from the emotional expression assessment unit.

The emotion assessment apparatus may also have a photographing unit for photographing the face of the subject, and the detecting unit may detect heartbeat information based on changes in image data acquired by the photographing unit.

For this emotion assessment apparatus, the mental state may include a first mental state that can be assessed based on the number of heart rate variations, regardless of whether the emotion is positive or negative, and a second mental state that can be assessed based on whether the emotion is positive or negative and on the number of heart rate variations, and the emotional expression assessment unit may use the assessment results from the emotion assessment unit at least when assessing the second mental state.

The predetermined time period for this emotion assessment apparatus may be set repeatedly, and the emotional expression assessment unit may perform assessment for each predetermined time period.

The photographing unit for this emotion assessment apparatus may photograph faces of multiple subjects, while the emotion assessment apparatus may also have measuring location identifying means for identifying each face from the screen on which the multiple subjects are displayed and identifies measuring locations for each identified face, and the detecting unit may acquire heartbeat information based on changes in the images at the measuring location for each face.

For this emotion assessment apparatus, the subjects may be students attending a lecture, and the emotional expression assessment unit may assess whether or not the students are in the optimal mental state for attending the lecture, based on the number of heart rate variations and the assessment results from the emotion assessment unit.

The emotion assessment apparatus may also have a stimulus generation unit for generating stimuli being recognized in a sensory manner either visually or audibly when generated, stimuli with informational content that is understood either visually or audibly, and stimuli including at least one of an image or voice of a specific person and wherein the stimulus generation unit repeatedly generates the same type of stimuli during multiple previously established periods before and after a pause period, and the emotional expression assessment unit assesses the mental state of the subject at least during the multiple previously established periods.

For this emotion assessment apparatus, negative emotions may be emotions felt by the subject when the subject is in at least one condition of brain fatigue, anxiety or depression.

For this emotion assessment apparatus, the mental state of the subject being assessed by the emotional expression assessment unit may include at least one of a stable state, a surprised state, an emotionally moved state or an angry state.

When the number of heart rate variations counted by the counting unit of the emotion assessment apparatus is one time, the emotional expression assessment unit may assess that the mental state is a surprised state.

When the number of heart rate variations counted by the counting unit is multiple times and the emotion of the subject assessed by the emotion assessment unit is a positive emotion, the emotional expression assessment unit may assess that the mental state is an emotionally moved state.

When the number of heart rate variations counted by the counting unit is multiple times and the emotion of the subject assessed by the emotion assessment unit is a negative emotion, the emotional expression assessment unit may assess that the mental state is an angry state.

When the number of heart rate variations counted by the counting unit is zero times and a state in which the heart rate is below the average heart rate has been maintained during a predetermined time period, the emotional expression assessment unit may assess that the mental state is a stable state.

When the number of heart rate variations counted by the counting unit is zero times and a state in which the heart rate is greater than or equal to the average heart rate has been maintained during a predetermined time period, the emotional expression assessment unit may assess that the mental state is an emotion-unassessable state in which the mental state cannot be assessed.

The emotion assessment program according to one embodiment of the disclosure causes a computer to perform: a step of detecting heartbeat information including the heart rate of a subject, a step of assessing whether the emotion of the subject is a negative emotion or a positive emotion based on the heartbeat information, a step of counting the number of heart rate variations within a predetermined time period, the heart rate variations being transitions from a state in which the heart rate is below the average heart rate to a state in which the heart rate is greater than or equal to the average heart rate and with heart rate increase greater than or equal to a predetermined value, a step of assessing the mental state of the subject based on the number of heart rate variations, and using the assessment results to assess the mental state, and a step of outputting the assessment results for the mental state.

The emotion assessment method according to one embodiment of the disclosure comprises detecting heartbeat information including the heart rate of a subject by a detecting unit, assessing whether the emotion of the subject is a negative emotion or a positive emotion based on the heartbeat information by an emotion assessment unit, counting the number of heart rate variations within an predetermined time period by a counting unit, the heart rate variations being transitions from a state in which the heart rate is below the average heart rate to a state in which the heart rate is greater than or equal to the average heart rate and with heart rate increase greater than or equal to a predetermined value, assessing the mental state of the subject based on the number of heart rate variations by an emotional expression assessment unit, the emotional expression assessment unit using the assessment results from the emotion assessment unit to assess the mental state, and outputting the assessment results from the emotional expression assessment unit by an output unit.

The emotion assessment apparatus, emotion assessment method and emotion assessment program of the invention allow contactless detection of emotions of other parties.

BRIEF DESCRIPTION OF DRAWINGS

FIG. 25 is an example of image stimuli and sound stimuli used for assessing communication obstacle factors in the three categories of compatibility, vision/hearing and mental illness.

FIG. 33 is an example of assessment of the cause of obstructed communication with an elderly person.

FIG. 34(A) is an example of true values for reactions expressed upon periodic exposure to a stimulus, and FIG. 34(B) is an example of assessment of emotional expression when a subject has been exposed to a stimulus at the timing represented in FIG. 34(A).

DESCRIPTION OF EMBODIMENTS

The emotion assessment apparatus, emotion assessment method and emotion assessment program of the invention will now be explained with reference to the attached drawings. However, it is to be understood that the technical scope of the invention is not limited to the embodiments described herein and includes the invention and its equivalents as laid out in the Claims.

Figure 1:
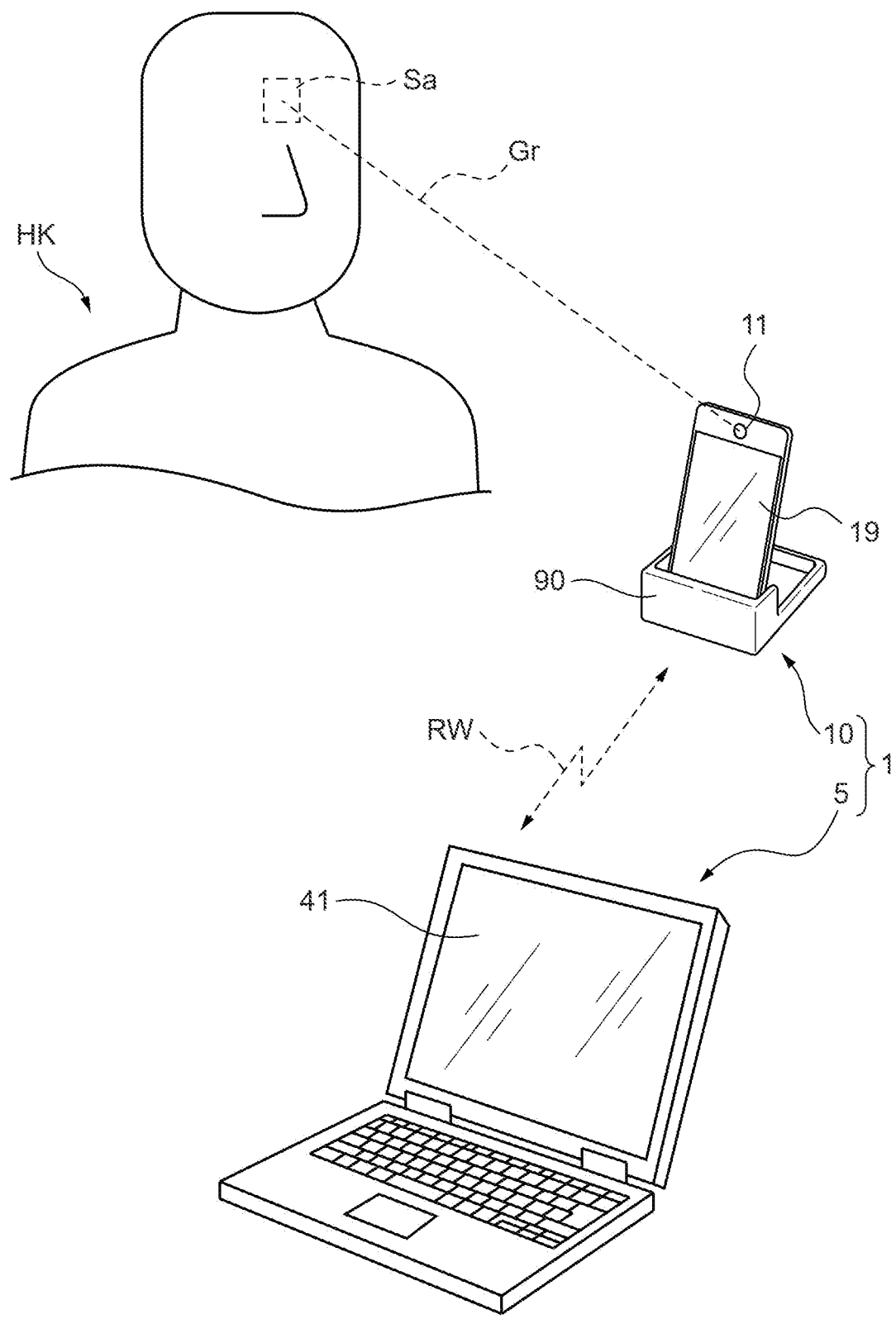
FIG. 1 is a perspective view showing an emotion assessment apparatus according to an embodiment of the disclosure in a state of use.

FIG. 1 is a perspective view showing an emotion assessment apparatus 1 according to an embodiment of the disclosure in a state of use. As shown in FIG. 1, the emotion assessment apparatus 1 comprises an imaging unit 10 and a data terminal 5. In the example shown, the imaging unit 10 is a portable terminal such as a smartphone, and the data terminal 5 is a laptop computer (PC) equipped with a display screen 41. There is no limitation to this example, however, and a tablet terminal or digital camera may be used as the imaging unit 10 while a tablet terminal, desktop PC or specialized processing device may be used as the data terminal 5. The imaging unit 10 and data terminal 5 may also be integrated.

FIG. 1 shows a state where the imaging unit 10 is mounted on a stand 90 that holds the imaging unit 10. As shown in FIG. 1, the imaging unit 10 comprises an imaging device 11 and a display screen touch panel 19 for setting operation of the imaging unit 10.

Many elderly in particular are persons with a fear of measurements, persons with resistance to the act of measurement itself, such as attachment of a sensor during measurement, or persons that experience temporary negative emotion simply by hearing an explanation of measurement, and such persons may not allow accurate measurement of negative emotion. The emotion assessment apparatus 1 therefore uses an imaging unit 10 with an imaging device (camera) 11, photographing the exposed parts of the skin of the subject (for example, the facial forehead or cheeks), so that the measurement itself is not stressful. The emotion assessment apparatus 1 also extracts brightness changes in synchronization with blood flow from the obtained image, and automatically detects a pulse wave signal as heartbeat information of the subject, without contacting the subject and without the subject being conscious of it.

The imaging device 11 is a CMOS (Complementary Metal Oxide Semiconductor) or CCD (Charge Coupled Device) type image sensor, for example. For each measurement, the imaging device 11 performs automatic photography of images Gr of a measuring region Sa of the forehead of the subject HK, as shown in FIG. 1, taking several images in a continuous manner without operation by the subject. The imaging unit 10 functions to automatically follow the measuring region Sa of the forehead of the subject HK, using an internal facial recognition application. This allows the pulse wave of the subject HK to be obtained even when the subject HK moves around within the installed area of the imaging unit 10. As shown in FIG. 1, the imaging unit 10 sends the photographed image data of the subject HK to the data terminal 5 by radio waves RW using an internal wireless communication function.

Figure 2:
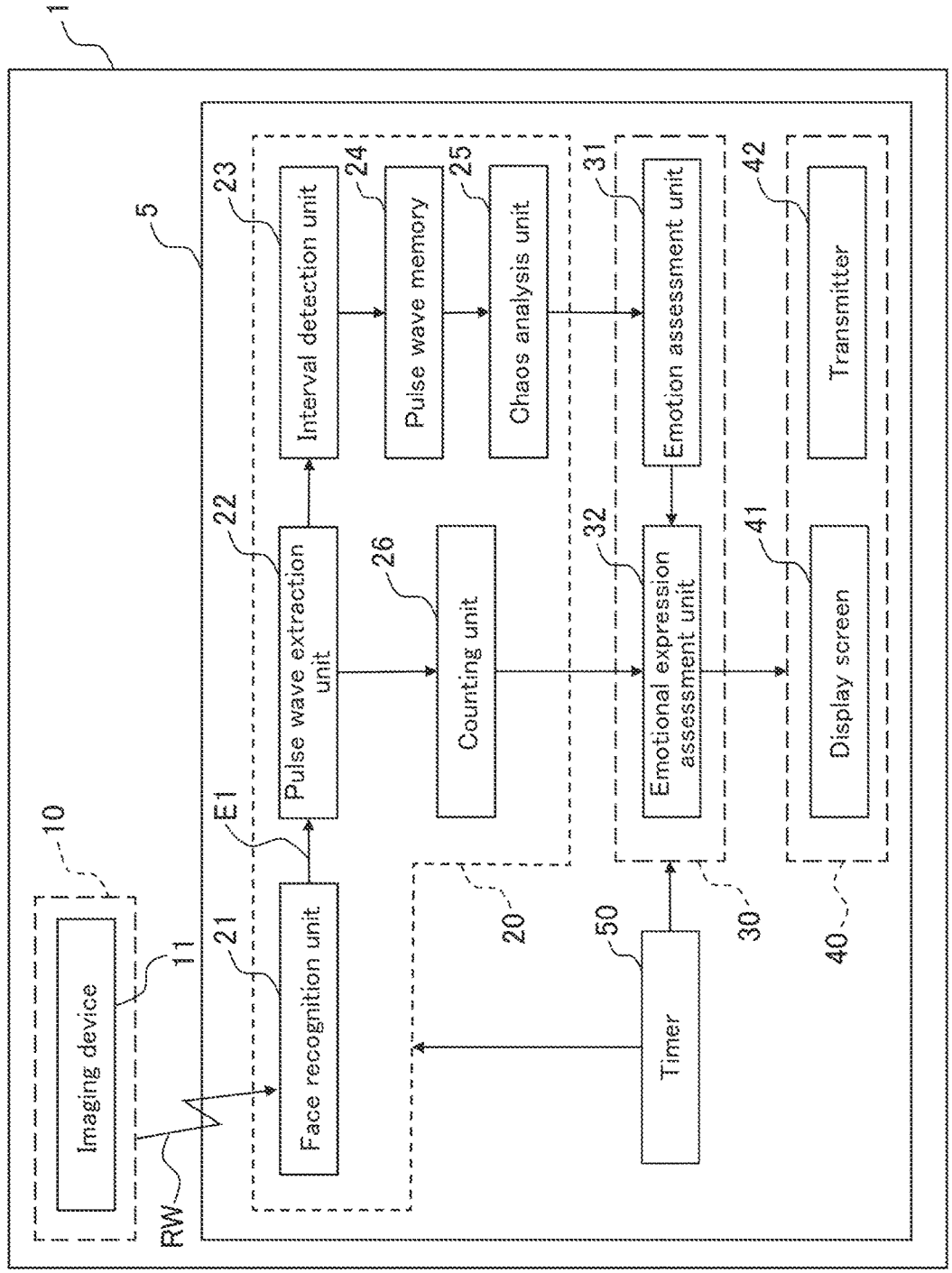
FIG. 2 is a block diagram of the emotion assessment apparatus according to an embodiment of the disclosure.

FIG. 2 is a block diagram of the emotion assessment apparatus 1. As shown in FIG. 1, the data terminal 5 of the emotion assessment apparatus 1 includes an emotion detection unit 20, an assessing unit 30, a notification unit 40 and a timer 50. The emotion detection unit 20 includes a face recognition unit 21, a pulse wave extraction unit 22, an interval detection unit 23, a pulse wave memory 24, a chaos analysis unit 25 and a counting unit 26. The assessing unit 30 comprises an emotion assessment unit 31 and an emotional expression assessment unit 32. The notification unit 40 comprises a display screen 41 and a transmitter 42. The pulse wave memory 24 may be composed of a hard disk or semiconductor memory, the display screen 41 may be composed of a liquid crystal display, and the timer 50 may be composed of a publicly known clock circuit. The other elements are realized as software (programs) executed by a computer in the data terminal 5 including a CPU, ROM and RAM.

The face recognition unit 21 analyzes facial states using a contour detection algorithm or feature point extraction algorithm against the image Gr of the subject HK photographed by the imaging device 11, and identifies skin exposed sections such as the forehead as measuring locations. The face recognition unit 21 outputs a time series signal E1, as skin color-representing data for the measuring location, to the pulse wave extraction unit 22.

The pulse wave extraction unit 22 extracts a pulse wave signal for the subject HK from the time series signal E1, and outputs the signal to the interval detection unit 23. Since capillaries are concentrated inside the measuring region Sa of the forehead of the subject HK, a brightness change component synchronized with blood flow of the subject HK is contained within the image Gr. In particular, since the pulse wave (blood flow change) is maximally reflected in the brightness change component for green light in the image Gr, the pulse wave extractor 22 uses a bandpass filter which allows passage of frequencies of about 0.5 to 3 [Hz] (the range of human pulse waves) to extract the pulse wave signal from the brightness change component for green light in the time series signal E1.

The imaging unit 10, face recognition unit 21 and pulse wave extraction unit 22 are examples of detecting units that detect heartbeat information of a subject. However, the function of the detecting unit does not necessarily need to be separated into the imaging unit 10 and data terminal 5, and for example, the functions of the face recognition unit 21 and pulse wave extraction unit 22 may be performed by the imaging unit 10, and the imaging unit 10 may be included in the data terminal 5.

Figure 3:
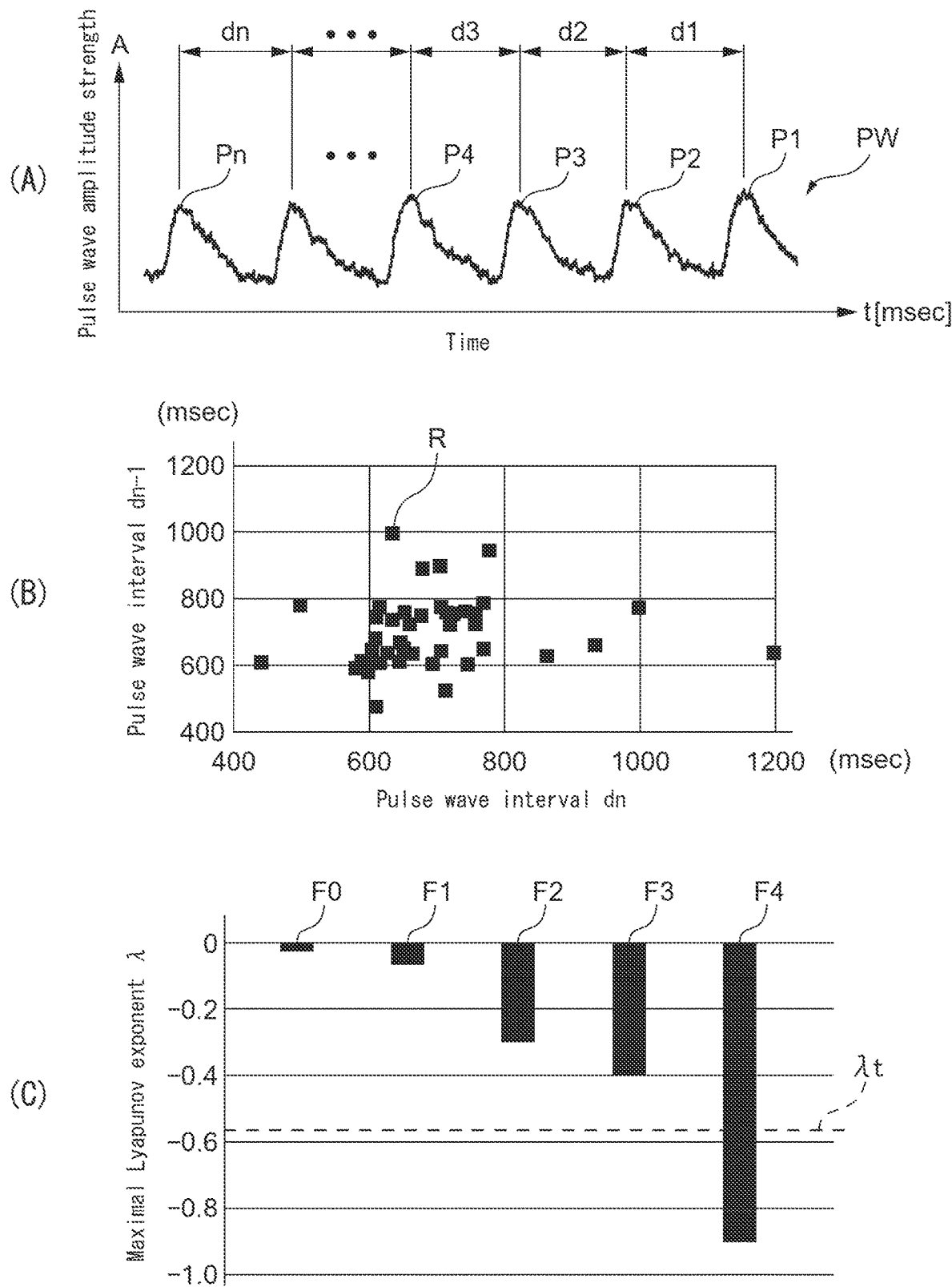
FIG. 3(A) to (C) are graphs illustrating the principle by which a negative emotion is assessed from a pulse wave.

FIG. 3(A) to (C) are graphs illustrating the principle by which a negative emotion is assessed from a pulse wave. FIG. 3(A) represents an example of a waveform for a pulse wave signal PW, the horizontal axis t being time (milliseconds) and the vertical axis A being amplitude intensity of the pulse wave. As shown in FIG. 3(A), the pulse wave signal PW is a triangular wave reflecting variation in blood flow due to heart beat, the intervals between peak points P1 to P(n+1) of strong amplitude intensity, for pulse waves representing the highest blood flow points, being designated as pulse wave intervals dl to dn.

The interval detector 23 detects peak points P1 to P (n+1) for the pulse wave signal PW of the subject HK, calculates the pulse wave intervals dl to dn in millisecond units using the timer 50, and generates pulse wave interval time series data from the pulse wave intervals dl to dn.

The pulse wave memory 24 stores the pulse wave intervals dl to dn detected by the interval detector 23, as pulse wave interval time series data.

FIG. 3(B) is a graph showing an example of fluctuation in pulse wave intervals. This type of graph is known as a Lorenz plot, with the abscissa representing the pulse wave interval dn and the ordinate representing the pulse wave interval dn−1 (both in millisecond units), where time series data for pulse intervals are plotted on coordinates (dn, dn−1) for n=1, 2, . . . . Since the degree of variation of the dots R in the graph of FIG. 3(B) is known to reflect brain fatigue in a subject HK, displaying the data scatter plot of FIG. 3(B) on the display screen 41 allows convenient monitoring of brain fatigue during measurement of the subject HK.

The chaos analysis unit 25 uses the pulse wave interval time series data stored in the pulse wave memory 24, i.e. the coordinates (dn, dn−1) in the Lorenz plot of FIG. 3(B), to calculate the maximal Lyapunov exponent λ by the following formula (1).

[Mathematical Formula 1]

$$\lambda = \frac{1}{M}\sum_{k=1}^{M}\log_2\frac{d(k)}{d(k-1)} \quad (1)$$

Here, M is the total sample time for pulse wave intervals dl to dn, and d is the distance between patterns at time k and time k−1 in the time series data (the distance on the two-dimensional plane of the Lorenz plot). The interval detector 23 and chaos analyzer 25 are examples of calculating units that calculate the maximal Lyapunov exponent representing the degree of fluctuation in heartbeat interval from heartbeat information.

The maximal Lyapunov exponent will now be explained in brief. When the hearts of mammals including humans are active in a fixed cycle, certain parts become exhausted and are more prone to breakdown, similar to mechanical devices. Such activity continues for prolonged periods, and therefore exhaustion is normally avoided by fluctuation in a complex system. This latter function is performed by autonomic nerves. Stress and psychological damage, however, causes autonomic nerves to concentrate on the stressors and makes them less able to manage fluctuation of the complex system. Positive or negative emotion (related to autonomic nerves) correlates not with just the presence of fluctuation in a complex (chaotic) system, but with the degree of fluctuation in the complex system. For example, when the fluctuation has a fixed periodicity the graph is circular or elliptical, in which case there is no fluctuation in the complex system. Therefore, a positive maximal Lyapunov exponent means that the complex system has fluctuation, indicating that the subject has a positive emotion. A negative maximal Lyapunov exponent, on the other hand, means that there is no fluctuation in the complex system, indicating that the subject has a negative emotion. The maximal Lyapunov exponent may thus be used as an index for quantitation of the degree of fluctuation in the complex system, allowing assessment of whether the subject has positive emotion or negative emotion. This is the principle behind emotion sensing using the maximal Lyapunov exponent.

The LF/HF method may also be used for emotion assessment instead of the maximal Lyapunov exponent. The LF/HF method evaluates autonomic nerve activity from heart rate variability, using the ratio (LF/HF) between the low-frequency component (LF) and the high frequency component (HF) as an index of the sympathetic nerve activity. Frequency analysis is performed on fluctuation in the heartbeat or pulse wave interval, and with LF in a power spectrum of 0.04 to 0.15 Hz and HF in a power spectrum of 0.15 to 0.4 Hz, an LF/HF ratio of less than 2.0 can be judged to be "positive emotion", a ratio of 2.0 and <5.0 can be judged to be "somewhat negative emotion", and a ratio of 5.0 or greater can be judged to be "negative emotion". However, while the maximal Lyapunov exponent can be analyzed even with 30-second pulse wave fluctuation, the LF/HF method requires a measurement time of about 3 minutes for accurate measurement of low-LF frequency components.

FIG. 3(C) is a graph showing the relationship between maximal Lyapunov exponent indicating the degree of fluctuation of heartbeat or pulse wave intervals, and negative emotion. This graph shows the results of a physician inquiry questionnaire of 10 male and female adults, with responses to the degree of fatigue and whether or not the fatigue was due to brain fatigue, anxiety or depression, measuring the maximal Lyapunov exponent λ for pulse wave intervals of the same subjects, and representing the relationship between obtained responses and X value. F0 corresponds to "no fatigue", F1 to "age-related fatigue", F2 to "temporary fatigue", F3 to "chronic fatigue", and F4 to "negative emotion". The ordinate of the graph is the maximal Lyapunov exponent λ.

Based on FIG. 3(C) it is seen that the maximal Lyapunov exponent λ is a small absolute value close to zero with simple fatigue, but with negative emotion it is a negative value with a large absolute value. Taking measurement variation into consideration for the 10 male and female adults, the threshold for the maximal Lyapunov exponent indicating whether or not negative emotion was felt can be set to about −0.6.

The emotion assessment unit 31 assesses that a negative emotion has developed in the subject when the maximal Lyapunov exponent λ acquired from the chaos analyzer 25 satisfies formula (2) below, and assesses that a negative emotion has not developed in the subject when λ does not satisfy formula (2).

$$\lambda \le \lambda t \tag{2}$$

The threshold λt is −0.6 in this case, but another value may be used depending on the properties required for the emotion assessment apparatus 1. The emotion assessment unit 31 is an example of an emotion assessment unit that assesses that the emotion of the subject is at least one negative emotion from among brain fatigue, anxiety and depression, or assesses that the emotion of the subject is a positive emotion without brain fatigue, anxiety or depression, based on the maximal Lyapunov exponent.

Figure 4:
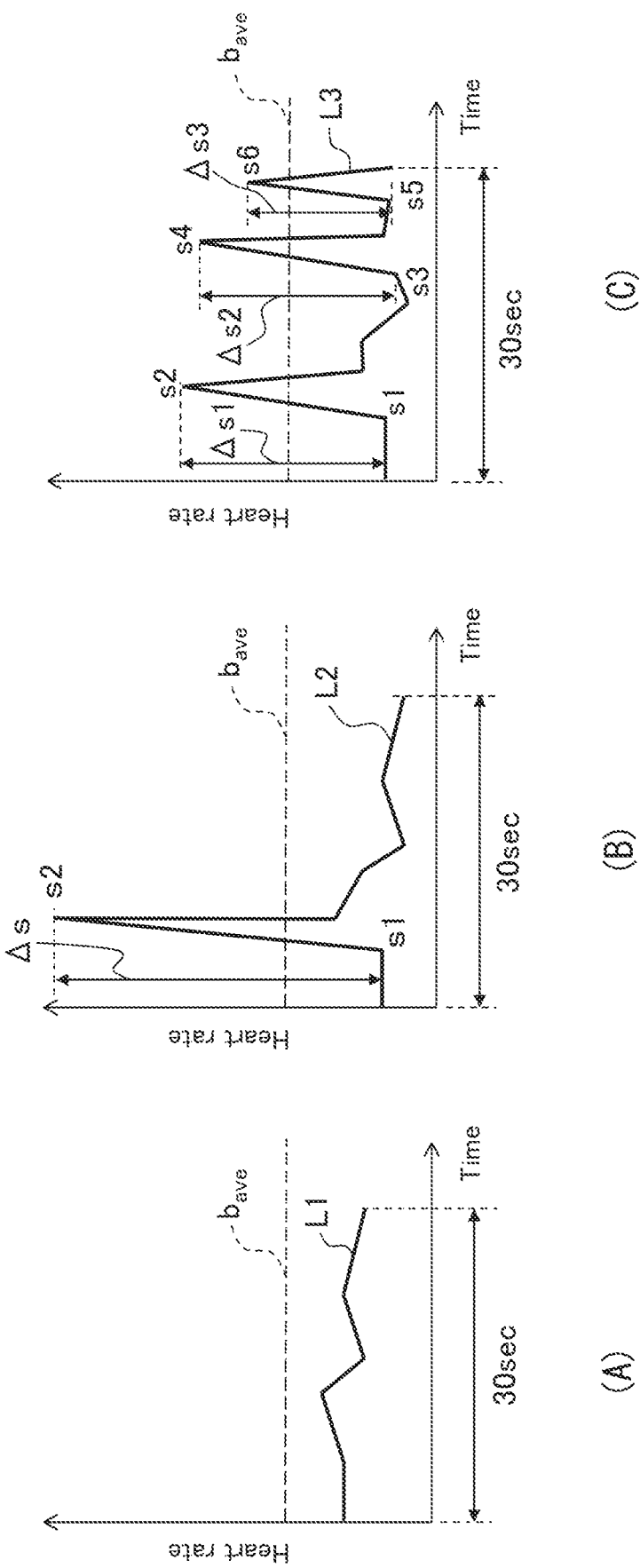
FIG. 4(A) to (C) are graphs illustrating the principle by which an emotion is assessed from heart rate variation during a predetermined time period.

The counting unit 26 counts the number of heart rate variations for transition from a state in which the heart rate is below the average heart rate to a state in which the heart rate is above the average heart rate, where heart rate increase is greater than or equal to a predetermined value during a predetermined time period. FIG. 4(A) to (C) are graphs illustrating the principle by which an emotion is assessed from heart rate variation during a predetermined time period. The ordinate represents heart rate, and the abscissa represents time. The value $b_{ave}$ represents the average heart rate for the subject HK. When the average heart rate of the subject HK is unknown, an average value of 65 [bpm] may be used. The region where the heart rate is above the average heart rate $b_{ave}$ is designated as the "emotional zone", and the region where the heart rate is below the average heart rate $b_{ave}$ is designated as the "calm zone".

The heart rate varies with time, as shown by FIG. 4(A) to (C). The counting unit 26 counts the number of heart rate variations in which the heart rate transitions from the calm zone to the emotional zone, i.e. transitions from a state in which the heart rate is below the average heart rate $b_{ave}$ to a state in which the heart rate is above the average heart rate $b_{ave}$, and wherein the variation range Δs in the heart rate is greater than or equal to a predetermined value, during a predetermined time period. For example, the predetermined time period may be 30 [sec] and the predetermined value may be 10 [bpm]. The predetermined time period 30 [sec] matches the minimum period that allows precision in Lyapunov analysis to be maintained. There is no limitation to these values, however, and the predetermined time period and predetermined value may be set as appropriate for the degree of variation in the heart rate of the subject as their emotion changes.

FIG. 4(A) shows an example where the heart rate is below the average heart rate $b_{ave}$ during the predetermined time period. In this case, the curve L1 representing the heart rate during the predetermined time period is in the calm zone, and the counting unit 26 counts "0" as the number of heart rate variations in which the heart rate transitions from a state below the average heart rate to a state above the average heart rate.

FIG. 4(B) shows an example of a single large fluctuation in heart rate. As shown in FIG. 4(B), in the curve L2 representing the heart rate, the heart rate s1 is below the average heart rate $b_{ave}$ and the heart rate s2 is above the average heart rate $b_{ave}$. When Δs as the difference between s1 and s2 is above the predetermined value, the counting unit 26 counts "1" as the number of heart rate variations for transition from a state below the average heart rate to a state above the average heart rate, where heart rate increase is above a predetermined value during a predetermined time period.

FIG. 4(C) shows an example of multiple fluctuations in heart rate. As shown in FIG. 4(C), in the curve L3 representing the heart rate, the heart rates s1, s3 and s5 are below the average heart rate $b_{ave}$ and the heart rates s2, s4 and s6 are above the average heart rate $b_{ave}$. When Δs1 as the difference between s1 and s2, Δs2 as the difference between s3 and s4, and Δs3 as the difference between s5 and s6 are all above the predetermined value, the counting unit 26 counts "3" as the number of heart rate variations for transition from a state below the average heart rate to a state above the average heart rate, where heart rate increase is above a predetermined value during a predetermined time period. FIG. 4(C) shows an example where the number of heart rate variations is 3, but there is no limitation to this example, and the counting unit 26 counts multiple heart rate variations even when the number of heart rate variations is 2, or 4 or more.

The emotional expression assessment unit 32 assesses the mental state of the subject HK based on the assessment results from the emotion assessment unit 31 and the number of heart rate variations counted by the counting unit 26. In FIG. 4(A) to (C), the predetermined time period shown is only a period of 30 [sec] as the initially set period, but the predetermined time period may be set repeatedly. The emotional expression assessment unit may also perform assessment for different predetermined time periods. The mental states of the subject HK include a stable state, a surprised state, an emotionally moved state and an angry state. The emotional expression assessment unit 32 therefore assesses whether or not the mental state of the subject HK is a stable state, surprised state, emotionally moved state or angry state, based on the assessment results from the emotion assessment unit 31 and the number of heart rate variations counted by the counting unit 26. Incidentally, the term "emotionally moved" means strong feeling or rising emotion, but it also includes other concepts with similar definitions, such as "stirred", "impressed" and "affected", or "joy". The term "anger" means being indignant, and also includes the meanings of similar terms such as "vexed".

When the number of heart rate variations counted by the counting unit 26 is zero times and a state in which the heart rate of the subject HK is below the average heart rate has been maintained for a predetermined time period, the emotional expression assessment unit 32 assesses that the mental state of the subject HK is a stable state. Since the heart rate during the predetermined time period is less than the average heart rate and has never risen above the average heart rate, the heart rate is in the calm zone, and the emotional expression assessment unit 32 can assess that the mental state of the subject HK is a stable state.

When the number of heart rate variations counted by the counting unit 26 is one time, the emotional expression assessment unit 32 may assess that the mental state is a surprised state. When the mental state of the subject HK is a surprised state, it is assumed that the heart rate varies once during the predetermined time period and does not continue. A surprised state of the subject HK may mean either that the emotion of the subject HK is a positive emotion or a negative emotion. When the number of heart rate variations counted by the counting unit 26 is "1", the emotional expression assessment unit 32 may assess that the mental state of the subject HK is a surprised state, regardless of whether the emotion of the subject HK that has been assessed by the emotion assessment unit 31 is a positive emotion or a negative emotion.

When the number of heart rate variations counted by the counting unit 26 is multiple times and the emotion of the subject HK assessed by the emotion assessment unit 31 is a positive emotion, the emotional expression assessment unit 32 assesses that the mental state of the subject HK is an emotionally moved state. When the emotion of the subject HK is a positive emotion, the subject HK is likely in a pleasant mental state. When the subject HK is in an emotionally moved mental state, such as when laughing at an humorous movie being appreciated by the subject HK, it is likely that the variation is from a calm zone where the heart rate is below the average value to an emotional zone above the average value, with the variation continuing for a certain time. Therefore, when the number of heart rate variations counted by the counting unit 26 is several times and the emotion of the subject HK assessed by the emotion assessment unit 31 is a positive emotion, the emotional expression assessment unit 32 can assess that the mental state of the subject HK is an emotionally moved state.

When the number of heart rate variations counted by the counting unit 26 is multiple times and the emotion of the subject HK assessed by the emotion assessment unit 31 is a negative emotion, the emotional expression assessment unit 32 assesses that the mental state of the subject HK is an angry state. When the emotion of the subject HK is a negative emotion, the subject HK is likely in an unpleasant mental state. When the subject HK is in an angered mental state such as having been scolded by a disliked person, it is likely that the variation is from a calm zone where the heart rate is below the average value to an emotional zone above the average value, with the variation continuing for a certain time. Therefore, when the number of heart rate variations counted by the counting unit 26 is several times and the emotion of the subject HK assessed by the emotion assessment unit 31 is a negative emotion, the emotional expression assessment unit 32 can assess that the mental state of the subject HK is an angry state.

Figure 5:
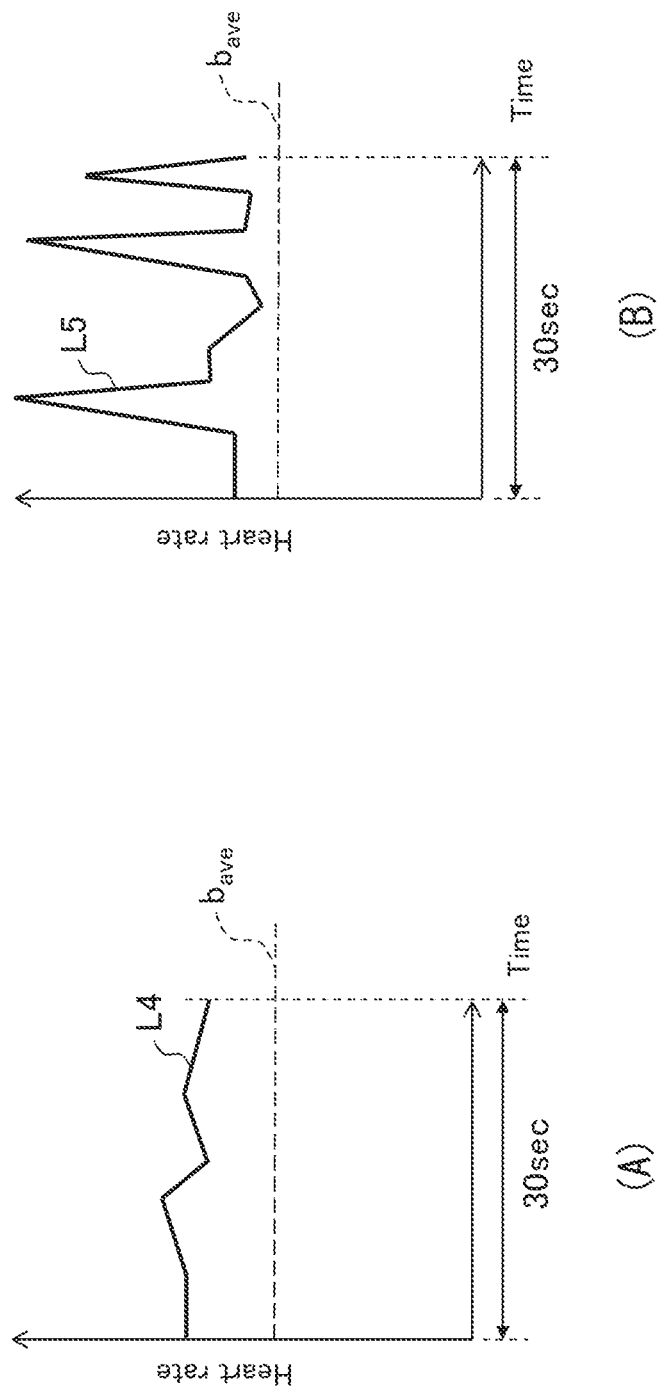
FIGS. 5(A) and (B) are graphs showing a case where it is difficult to assess an emotion from heart rate variation during a predetermined time period.

When the number of heart rate variations counted by the counting unit 26 is zero times and a state in which the heart rate of the subject HK is above the average heart rate has been maintained for a predetermined time period, the emotional expression assessment unit 32 assesses that mental state of the subject HK cannot be assessed, as an emotion-unassessable state. FIGS. 5(A) and (B) are graphs showing a case where it is difficult to assess an emotion from heart rate variation during a predetermined time period. FIG. 5(A) shows a state where the curve L4 representing the heart rate during the predetermined time period has stabilized in the emotional zone, and FIG. 5(B) shows a state where the curve L5 representing the heart rate during the predetermined time period varies significantly in the emotional zone. In these cases, however, the heart rate is in the emotional zone and is constantly above the average heart rate during the predetermined time period. This may be because the body of the subject HK is either in a fatigued state or has done intense exercise, making it difficult to make a proper assessment of emotional expression. Therefore when the number of heart rate variations counted by the counting unit 26 is "0" and a state in which the heart rate of the subject HK is above the average heart rate has been maintained for a predetermined time period, the emotional expression assessment unit 32 may assess that the mental state of the subject HK cannot be assessed, as an emotion-unassessable state.

Table 1 shows a list of mental states of a subject HK assessed by the emotional expression assessment unit 32 based on the assessment results for emotion of the subject HK by the emotion assessment unit 31, and the number of heart rate variations counted by the counting unit 26.

TABLE 1

| | | Number of heart rate variations during predetermined time period | | |
|---|---|---|---|---|
| | | Zero times | One time | Multiple times |
| Emotion analysis result | Positive emotion | Stable | Surprised | Emotionally moved |
| | Negative emotion | Stable | Surprised | Resentment |

As explained above, when the heart rate variability count is zero times, the emotional expression assessment unit 32 assesses that the mental state of the subject is in a "stable" state, regardless of whether the assessment results from the emotion assessment unit 31 indicates a positive emotion or a negative emotion, and when the heart rate variability count is one time, it assesses that the mental state of the subject is in a "surprised" state, regardless of whether the assessment results from the emotion assessment unit 31 indicate a positive emotion or a negative emotion. Thus, when the heart rate variability count is zero times or one time, the emotional expression assessment unit 32 can assess the mental state of the subject from the heart rate variability count regardless of whether the emotion assessment results indicate a positive emotion or a negative emotion. A mental state that can be assessed based on the number of heart rate variations regardless of whether the emotion is positive or negative will hereunder be referred to as a "first mental state".

When the number of heart rate variations is multiple times, the emotional expression assessment unit 32 assesses that the mental state of the subject is in an "emotionally moved" state if the assessment results from the emotion assessment unit 31 indicate a positive emotion, and assesses that the mental state of the subject is in a state of "resentment" if the assessment results from the emotion assessment unit 31 indicate a negative emotion. Thus, when the number of heart rate variations is multiple times, the emotional expression assessment unit 32 can assess the mental state of the subject based on the number of heart rate variations, whether the results of emotion assessment indicate a positive emotion or a negative emotion. A mental state that can be assessed based on whether the result of the emotion assessment is a positive or negative emotion and on the number of heart rate variations will hereunder be referred to as a "second mental state". The mental state of the subject includes the first mental state and the second mental state. The emotional expression assessment unit 32 uses the assessment results for whether the emotion of the subject assessed by the emotion assessment unit 31 is a positive emotion or a negative emotion when the number of heart rate is multiple times and when assessing whether the second mental state is an "emotionally moved" state or a "resentment" state. That is, the emotional expression assessment unit 32 uses the assessment results from the emotion assessment unit 31 at least when assessing the second mental state.

Thus, the emotional expression assessment unit 32 can use the assessment results from the emotion assessment unit 31 for assessment of the mental state, according to the mental state that is to be assessed.

However, the emotional expression assessment unit 32 may assess the mental state using the assessment results from the emotion assessment unit 31 (for example, a more detailed mental state), even if the heart rate variability count is zero times or one time. This is another example where the emotional expression assessment unit 32 can use the assessment results from the emotion assessment unit 31 to assess the mental state.

The notification unit 40 displays the assessment results for emotion of the subject HK from the emotional expression assessment unit 32 onto the display screen 41. In particular, the notification unit 40 displays the assessment results for the emotion of the subject HK from the emotional expression assessment unit 32 onto the display screen 41 while sending them out via the transmitter 42. The notification unit 40 is an example of an output unit that outputs the assessment results of the emotional expression assessment unit 32.

Figure 6:
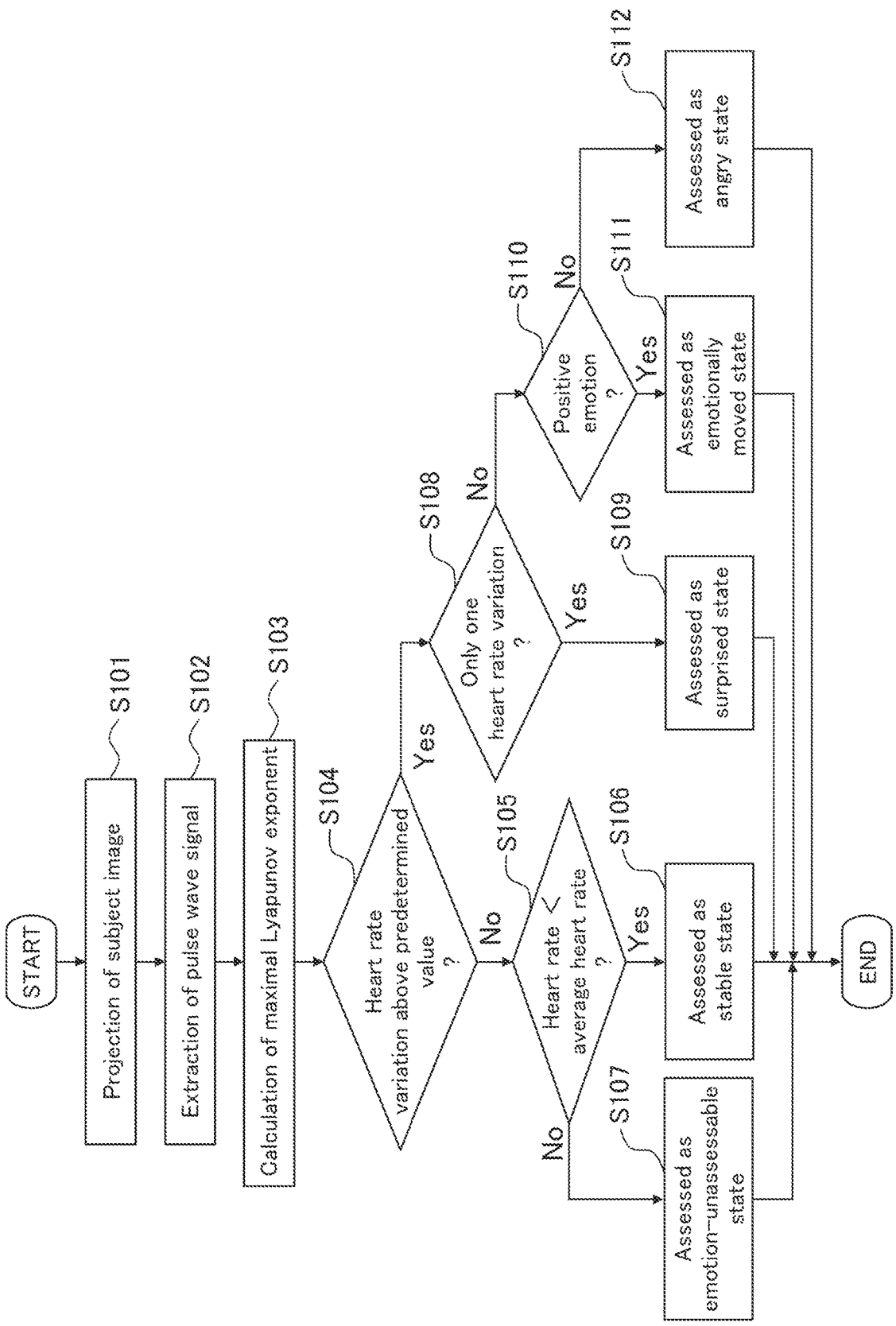
FIG. 6 is a flow chart showing an example of operation of an emotion assessment apparatus according to an embodiment of the disclosure.

FIG. 6 is a flow chart showing operation of the emotion assessment apparatus 1. First, in step S101, the imaging unit 10 takes an image Gr of the measuring region Sa of the subject HK with the imaging device 11, and sends the image data to the data terminal 5. Next, the face recognition unit 21 identifies the measuring location from the image data for the subject HK.

In step S102, the pulse wave extraction unit 22 extracts the pulse wave signal for the subject HK from the time series signal E1 for skin color at the measuring location identified by the face recognition unit 21. The interval detection unit 23 calculates the pulse wave interval from the pulse wave signal to generate time series data, and stores the time series data in the pulse wave memory 24.

Next, in step S103, the chaos analysis unit 25 calculates the maximal Lyapunov exponent $\lambda$ for the pulse wave interval based on the pulse wave interval time series data stored in S102.

In step S104, the counting unit 26 assesses whether or not heart rate variation greater than or equal to the predetermined value exists during the predetermined time period, based on the time-dependent change in heart rate extracted from the pulse wave signal. When heart rate variation above the predetermined value does not exist, it is assessed in step S105 whether or not the heart rate of the subject HK is below the average heart rate during the predetermined time period.

When a state in which the heart rate of the subject HK is below the average heart rate has been maintained for the predetermined time period, the emotional expression assessment unit 32 assesses in step S106 that the emotion of the subject HK is in a stable state. When a state in which the heart rate of the subject HK is above the average heart rate has been maintained for the predetermined time period, the emotional expression assessment unit 32 assesses in step S107 that the emotional expression assessment of the subject HK cannot be made, i.e. that it is an emotion-unassessable state.

When it has been assessed in step S104 that heart rate variation above the predetermined value exists, the counting unit 26 assesses in step S108 whether or not the number of heart rate variations of the subject HK is only one time during the predetermined time period. If the number of heart rate variations of the subject HK is only one time, the emotional expression assessment unit 32 assesses in step S109 that the emotion of the subject HK is in a surprised state.

On the other hand, when the number of heart rate variations of the subject HK during the predetermined time period is not only one time in step S108, i.e. when the count is multiple times, the emotion assessment unit 31 in step S110 compares the threshold $\lambda t$ with the maximal Lyapunov exponent $\lambda$ calculated in step S103, and judges that the subject HK has a positive emotion or a negative emotion.

When it has been judged that the emotion of the subject HK is a positive emotion, the emotional expression assessment unit 32 in step S111 assesses that the emotion of the subject HK is an emotionally moved state. When it has been judged that the emotion of the subject HK is a negative emotion, on the other hand, the emotional expression assessment unit 32 in step S112 assesses that the emotion of the subject HK is an angry state.

Thus, the emotion assessment apparatus according to an embodiment of the disclosure can assess, in a contactless manner, whether the mental state of a subject HK is a stable state, a surprised state, an emotionally moved state or an angry state, based on image data for the subject HK.

By using the emotion assessment apparatus according to an embodiment of the disclosure it is possible to discern the emotion of a person with whom it is difficult to communicate, at a nursing home, for example. That is, it is possible to discriminate whether an elderly person is delighted (emotionally moved) or angry (vexed) in regard to a caregiving activity carried out for the elderly person. This allows the caregiver to make a decision for how to carry out the caregiving activity for the elderly person, in response to the discrimination results. The emotional rhythm of a subject such as an elderly person may also be stored for the same activity every day during the same time period, allowing the emotional rhythm for the same activity at the same time period to be viewed. Knowing the emotional rhythm for the same activity during the same time period allows changes in subject condition to be ascertained indirectly. In addition, if the emotion assessment apparatus according to an embodiment of the disclosure is incorporated into an automatic training device for elderly persons, then the automatic training device may assess the emotion of elderly persons with poor emotional expression or facial expression, so that training can be carried out while providing suitable advice for them.

EXAMPLE 1

Figure 7:
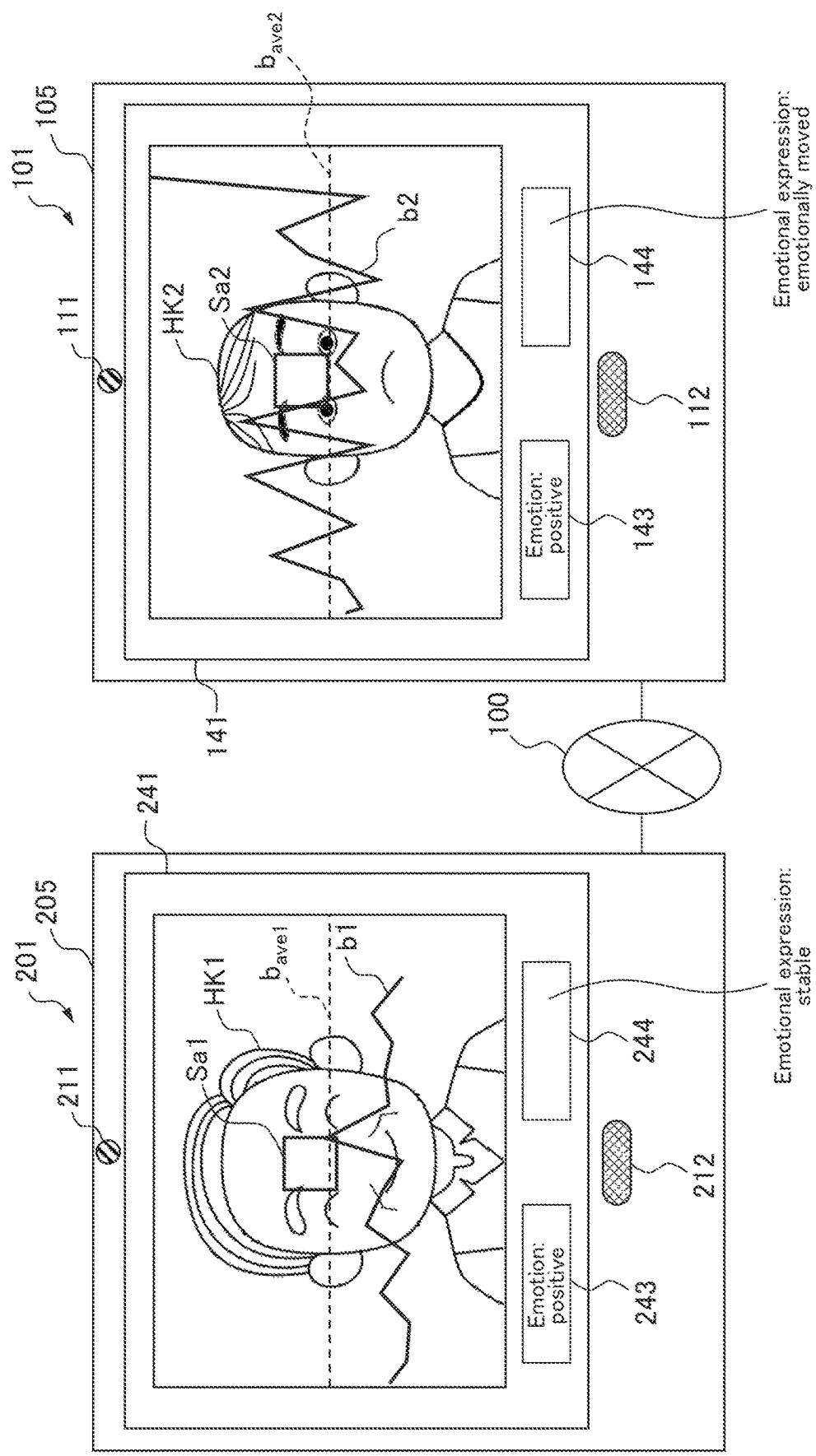
FIG. 7 is a diagram showing an example of screen display for web conferencing using the emotion assessment apparatus of Example 1.

The emotion assessment apparatus of Example 1 will now be described. FIG. 7 is a general schematic drawing of a web conferencing system using a data terminal equipped with the emotion assessment apparatus of Example 1.

During video communication such as web conferencing, it is often problematically difficult to read emotions from the facial expressions of other parties shown on the display screen. The emotion assessment apparatus of Example 1 assesses the emotion of another party from image data from the other party sent from the other party end in web conferencing.

The first emotion assessment apparatus 101 provided in front of the first subject HK1 and the second emotion assessment apparatus 201 provided in front of the second subject HK2 are connected via the internet 100, allowing web conferencing to take place between them. The first emotion assessment apparatus 101 has a first data terminal 105, a camera 111 and a microphone 112. The camera 111 takes an image of the first subject HK1, and sends it to the second data terminal 205 of the second subject HK2 via the internet 100, together with voice data collected through a microphone 112. Specifically, the camera 111 takes an image of the measuring region Sa1 of the first subject HK1, and the first data terminal 105 sends the image taken by the camera 111 to the second data terminal 205. Real time data for the heart rate b1 of the first subject HK1 are displayed on the display screen 241 of the second data terminal 205, together with images of the first subject HK1. The second data terminal 205 compares the heart rate b1 of the first subject HK1 with the average heart rate $b_{ave1}$, allowing the emotion of the first subject HK1 to be assessed from time-dependent change in the heart rate b1 during a predetermined time period. The assessment results for the emotion (for example, positive emotion) may be displayed in an emotion assessment region 243 of the display screen 241, or the assessment results for emotional expression (such as a stable state) may be displayed in an emotional expression display region 244.

The second emotion assessment apparatus 201 likewise has a second data terminal 205, a camera 211 and a microphone 212. The camera 211 takes an image of the second subject HK2, and sends it to the first data terminal 105 of the first subject HK1 via the internet 100, together with voice data collected through a microphone 212. Specifically, the camera 211 takes an image of the measuring region Sa2 of the second subject HK2, and the second data terminal 205 sends the image taken by the camera 211 to the first data terminal 105. Real time data for the heart rate b2 of the second subject HK2 are displayed on the display screen 141 of the first data terminal 105, together with images of the second subject HK2. The first data terminal 105 compares the heart rate b2 of the second subject HK2 with the average heart rate $b_{ave2}$, allowing the emotion of the second subject HK2 to be assessed from time-dependent change in the heart rate b2 during a predetermined time period. The assessment results for the emotion (for example, positive emotion) may be displayed in an emotion assessment region 143 of the display screen 141, or the assessment results for emotional expression (such as an emotionally moved state) may be displayed in an emotional expression display region 144.

FIG. 7 shows an example of web conferencing using an emotion assessment apparatus between two subjects, but the emotion assessment apparatus may likewise be used for web conferencing in the same manner between more than two subjects.

Figure 8:
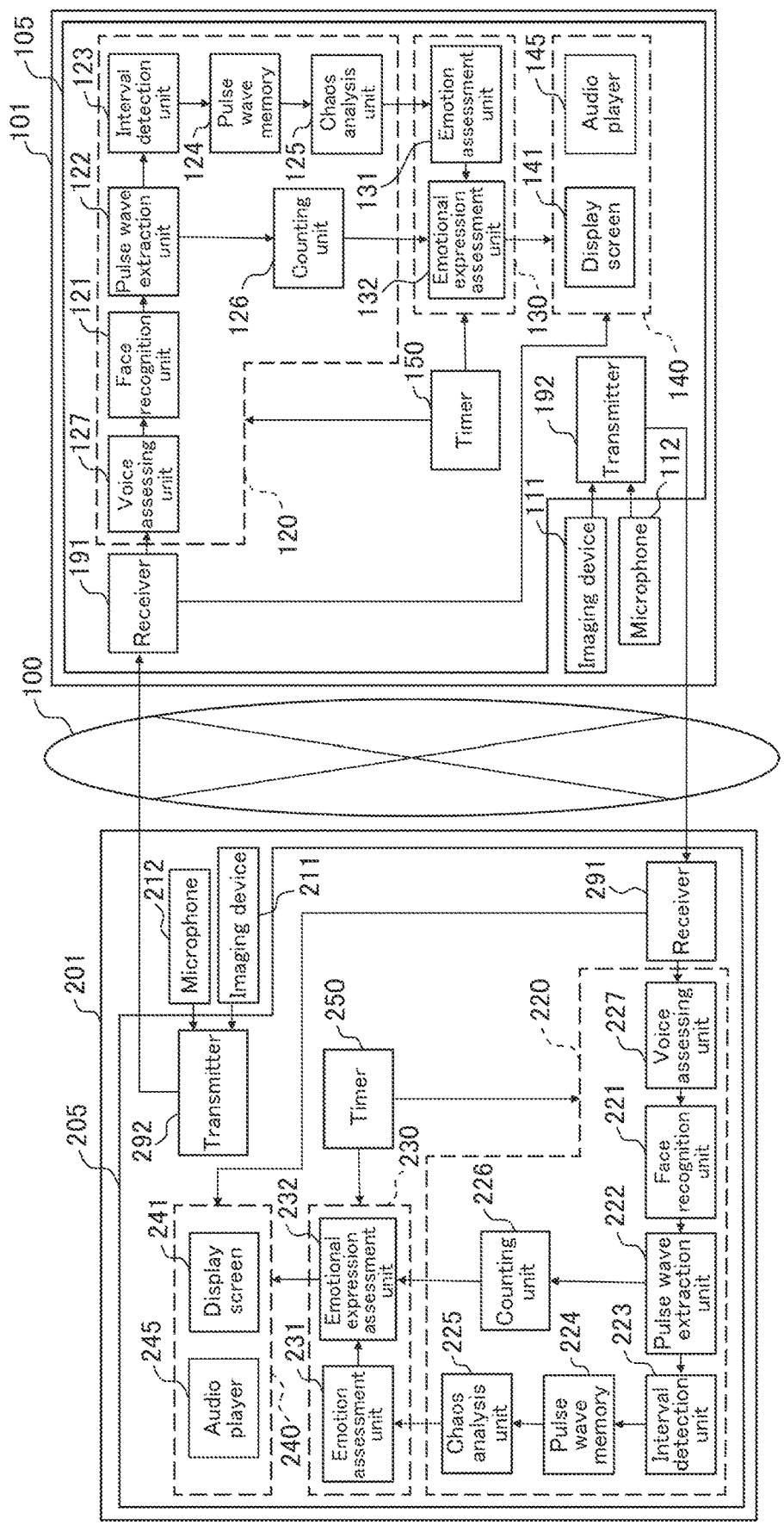
FIG. 8 is a block diagram for the emotion assessment apparatus of Example 1.

FIG. 8 is a block diagram for the emotion assessment apparatus of Example 1. The configurations of the first data terminal 105 and second data terminal 205 respectively comprise, in addition to the data terminal 5 of the embodiment shown in FIG. 2, also a receiver (191, 291), an audio player (145, 245), a voice assessing unit (127, 227) and a transmitter (192, 292).

Each transmitter (192, 292) sends image data and voice data for the first subject HK1 or second subject HK2 taken by the camera (111, 211) and microphone (112, 212), to the receiver 291 of the second data terminal 205 and the receiver 191 of the first data terminal 105, as the respective party terminals, via the internet 100.

Each receiver (191, 291) receives image data and voice data of the second subject HK2 and first subject HK1 sent from the transmitter 292 of the second data terminal 205 and the transmitter 192 of the first data terminal 105, respectively.

Each audio player (145, 245) plays back voice data included in the data received by the respective receiver (191, 291). The audio players (145, 245) may employ audio speaker units.

Each voice assessing unit (127, 227) judges which of the first subject HK1 and second subject HK2 is the speaker and which is the listener, from the duration of the voice data, based on the voice data received by each receiver (191, 291).

The speaker may express emotion simply by the act of speaking itself, making it impossible to make an accurate emotion assessment. Therefore, after the relationship between speaker and listener has continued for a certain time (such as 10 seconds or longer), the voice assessing unit (127, 227) may carry out emotion assessment and emotional expression assessment for the listener, constantly displaying the assessment results for the emotion of the listener on the display screen of the data terminal at the speaker end. This allows the speaker end to ascertain the emotion of the listener who is listening to the words of the speaker.

The Examples described above represent analysis of emotions at the receiving end based on image data send from the sending end. Since the emotion assessment apparatus of Example 1 calculates the heart rate (pulse) from acquired image information, the sampling rate is the frame rate of the images. Therefore, the transmission rate of received images may be monitored and emotion assessment may be carried out only when the transmission rate is in an appropriate range.

When multiple persons are simultaneously participating in web conferencing, it may not be possible for the image data for the other party ends to be acquired at appropriate timings given the restrictions of the communication line capacity. In such cases, emotion assessment may be switched to either the sending end or the receiving end, depending on the transmission rate value. Specifically, instead of assessing emotions based on the image data transmitted in real time, the method used may be either a method of first sending previously acquired image data of the listener to the speaker and then assessing emotions at the speaker end (first method), or a method of sending the emotion results assessed at the listener end to the speaker end (second method). The first method is expected to handle a greater volume of transmitted image data. The second method, on the other hand, requires adjustment of the communication format for addition of assessment result data to the image data. The first method and second method are preferably switched as appropriate depending on the transmission rate.

When the sending end is angry, direct transmission of the emotion assessment results can potentially create a negative impression for the other party. In such cases, indirect feedback may be provided for the emotion assessment results, such as changing the color of the borders of the images of the sending end subject depending on the assessment results. In addition to changing the subject image borders, the colors of the measuring regions (Sa1, Sa2) and the curves in the graph for the heart rates (b1, b2) may also be changed. For example, it is possible to display emotional expression with the colors of the measuring regions (Sa1, Sa2), and to display emotion with the colors of the curves of the graphs for heart rate (b1, b2).

With the emotion assessment apparatus of Example 1, it is possible to assess the emotion of a listener who is listening to words of the speaker during web conferencing or the like.

EXAMPLE 2

Figure 9:
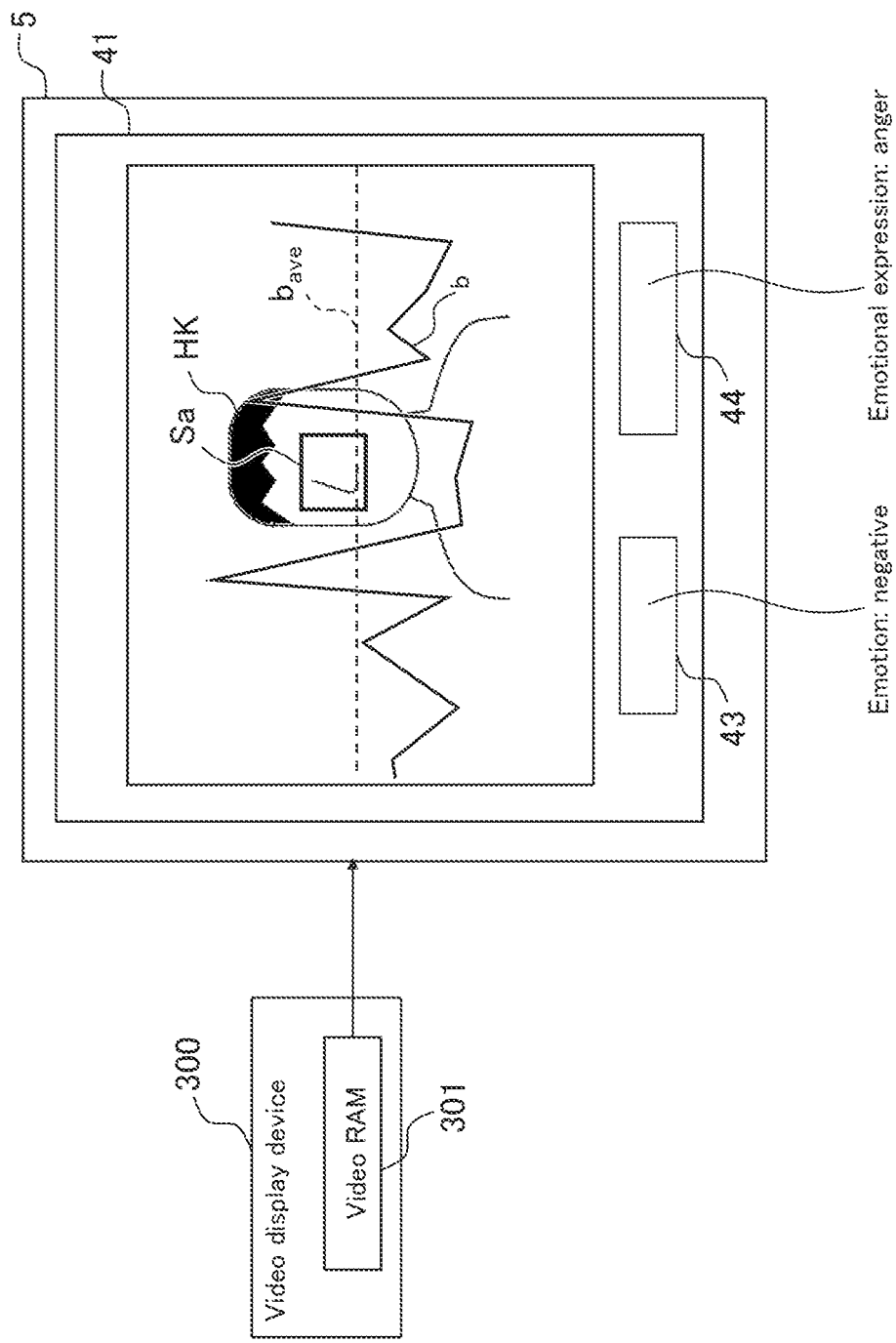
FIG. 9 is a diagram showing an example of the screen of the emotion assessment apparatus of Example 2.

The emotion assessment apparatus of Example 2 will now be described. FIG. 9 is a diagram showing an example of the screen of the emotion assessment apparatus of Example 2. The emotion assessment apparatus of Example 2 carries out emotion assessment using video displayed on a video display device 300 with provided software such as specialized web conferencing software or a video playback application or video player.

Unlike the emotion assessment apparatus of Example 1, the emotion assessment apparatus of Example 2 carries out emotion assessment by loading display images from video RAM (VRAM) 301 onto the screen using existing software, instead of using an imaging device to acquire images of subjects. The images of a subject HK loaded from video RAM 301 are displayed on the display screen 41 of the data terminal 5, while time-dependent changes in the heart rate b obtained from a pulse wave of the measuring region Sa are displayed on the display screen 41 together with the average heart rate $b_{ave}$. In addition, the assessment results for emotion (for example, negative emotion) may be displayed in an emotion assessment region 43 of the display screen 41, or the assessment results for emotional expression (such as an angered state) may be displayed in an emotional expression display region 44.

Figure 10:
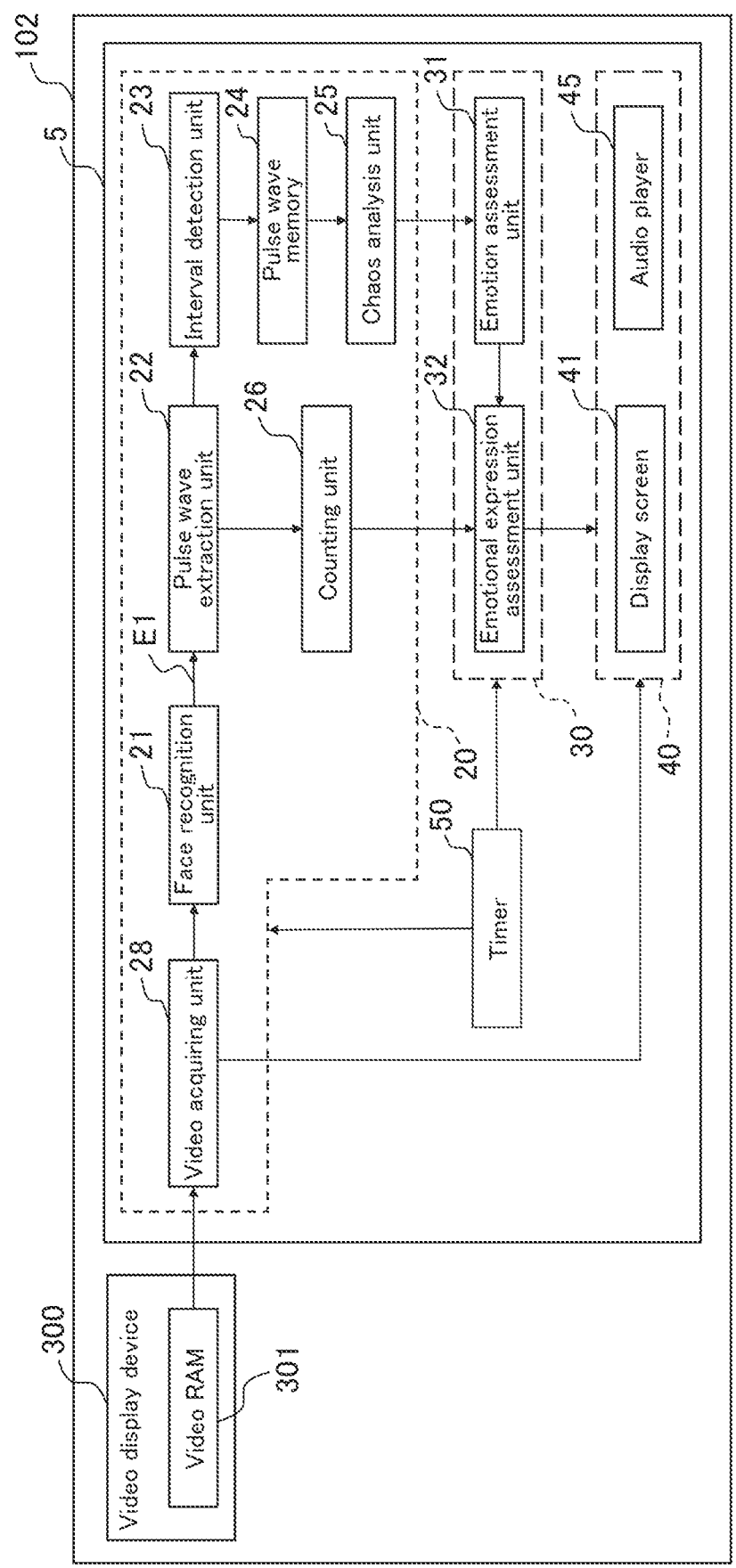
FIG. 10 is a block diagram for the emotion assessment apparatus of Example 2.

FIG. 10 is a block diagram for the emotion assessment apparatus 102 of Example 2. The emotion assessment apparatus 102 comprises a video display device 300 and a data terminal 5. In addition to the data terminal 5 of the embodiment shown in FIG. 2, this data terminal 5 also comprises a video acquiring unit 28, and comprises an audio player 45 instead of a transmitter.

The video acquiring unit 28 continuously and automatically takes multiple images of the measuring region Sa of the subject HK. The video acquiring unit 28 functions to automatically follow the measuring region Sa of the forehead of the subject HK, using an internal facial recognition application. This allows the pulse wave of the subject HK to be obtained even if the location of the measuring region Sa of the subject HK moves within the display area of the display screen 41.

The audio player 45 regenerates voice data that is included in the information acquired by the video acquiring unit 28. A speaker may also be used in the audio player 45.

In the emotion assessment apparatus of Example 1, images of the subject were taken with a camera, but in the emotion assessment apparatus of Example 2, existing images, with the person in the images as the subject, may be used for emotion assessment of the person, rather than taking new images. Emotion assessment may thus be carried out on a person appearing in an image uploaded to a video-sharing service, for example. Specifically, when images from an apology press conference for a certain person have been uploaded to a video display device 300, for example, the image data for the person may be loaded into the video acquiring unit 28 from the video RAM 301 for emotion assessment, to assess the emotion of the person during the apology press conference.

Alternatively, when an image of the other party has been displayed during a video call using the video display device 300, the image of the other caller may be loaded into the video acquiring unit 28 from the video RAM 301 for emotion assessment, to allow real time assessment of the emotion of the other party in the video call.

When the video display device 300 has been used to display video software for a movie or drama, images of the actors in the movie or drama may be loaded into the video acquiring unit 28 from the video RAM 301 for emotion assessment, to allow assess of the emotion of the actors during their performance.

As explained above, the emotion assessment apparatus of Example 2 allows assessment of the emotions of speakers during an apology press conference or allows video to be appreciated while analyzing the emotions of actors in the move or drama.

EXAMPLE 3

Figure 11:
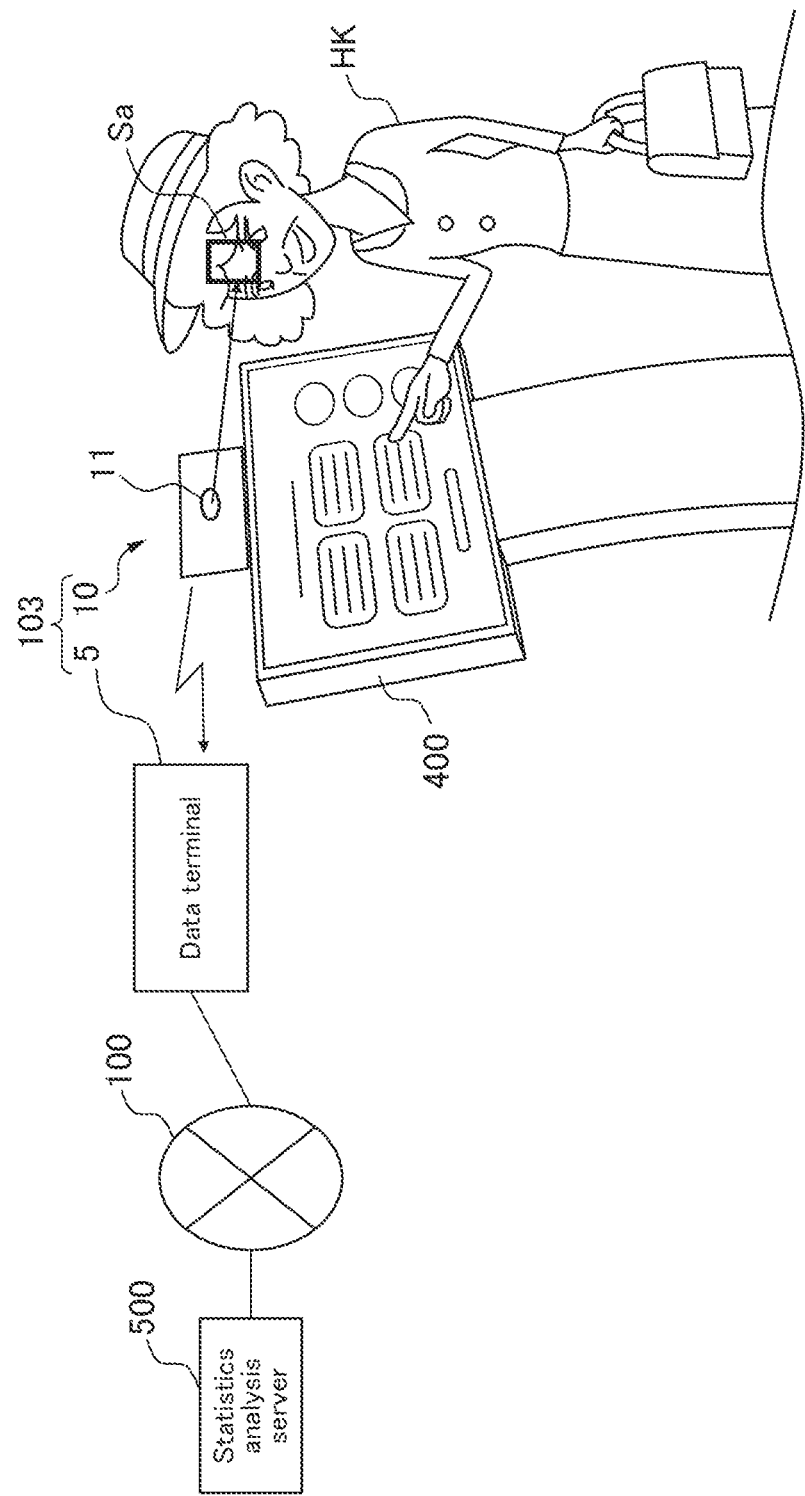
FIG. 11 is a schematic configuration diagram of a marketing research system using the emotion assessment apparatus of Example 3.

The emotion assessment apparatus of Example 3 will now be described. FIG. 11 is a schematic configuration diagram of a marketing research system using the emotion assessment apparatus of Example 3. The emotion assessment apparatus 103 of Example 3 has a data terminal 5 and an imaging unit 10. A subject HK observes images of products displayed on the display 400. The imaging device 11 of the imaging unit 10 takes images of the measuring region Sa of the subject HK while the imaging unit 10 sends the images of the subject HK taken by the imaging device 11 to the data terminal 5. The data terminal 5 assesses the emotion of the subject HK which observing the product displayed on the display 400, and sends the assessment results to the statistics analysis server 500 via the internet 100. The statistics analysis server 500 analyzes the emotions of multiple subjects observing the same product, allowing analysis of the appeal effect of the product for the subjects as consumers.

Figure 12:
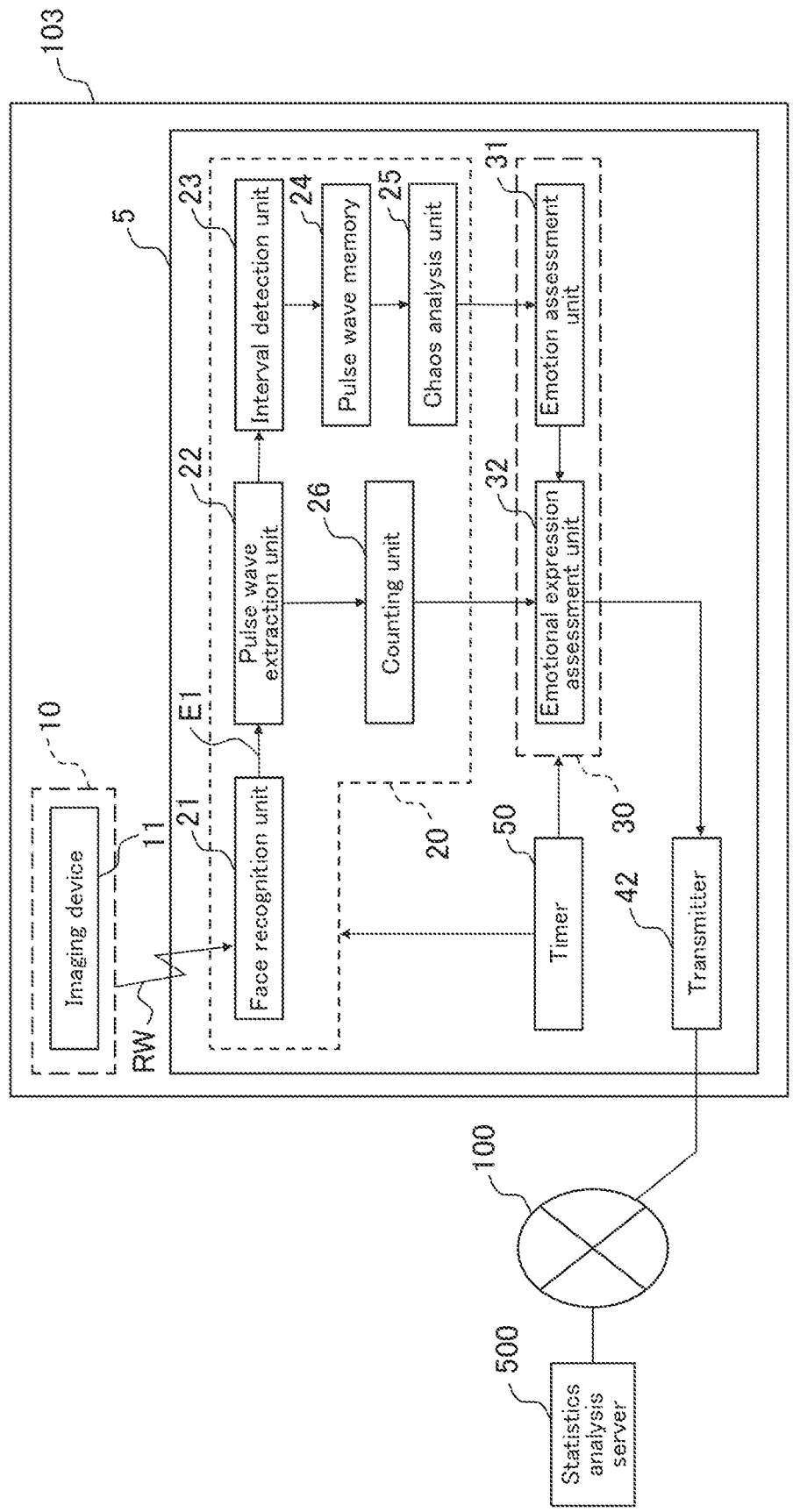
FIG. 12 is a block diagram for the emotion assessment apparatus of Example 3.

FIG. 12 is a block diagram for the emotion assessment apparatus of Example 3. The emotion assessment results for the subject HK are sent from the transmitter 42 to the statistics analysis server 500 via the internet 100, and the emotion assessment results for the subject HK are analyzed at the statistics analysis server 500. Since it is therefore not necessary for the emotion assessment results for the subject HK to be displayed on the data terminal 5, it is not necessary to provide a display screen.

The emotion assessment apparatus 103 of Example 3 applies marketing research using digital signage, allowing analysis of whether the product creates a favorable impression, based on the emotion assessment results for the subject (consumer). For example, an information display device such as digital signage may be combined with the emotion assessment apparatus 103 for product display, to allow marketing research in a manner such that consumer (subject) emotions in regard to the product are observed in real time, and the product is judged to be favored by consumers if the frequency of positive emotional expression is high.

Since the emotion assessment apparatus 103 can extract only consumer (subject) emotion assessment data for the given product, marketing research can be carried out without handling personal information.

EXAMPLE 4

Figure 13:
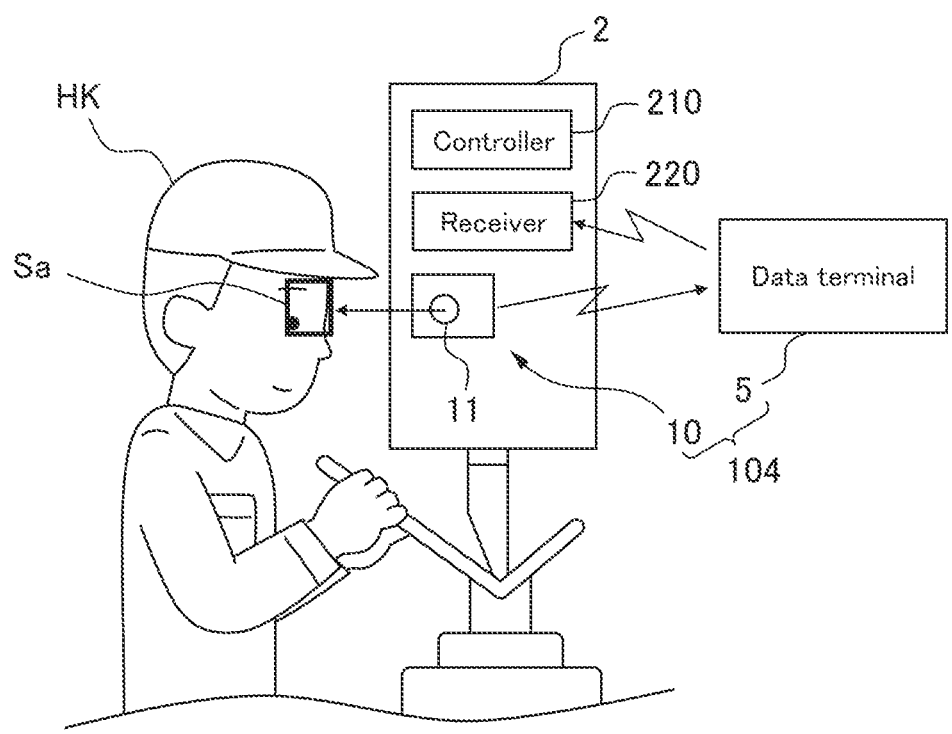
FIG. 13 is a schematic configuration diagram of a machine control system using the emotion assessment apparatus of Example 4.

The emotion assessment apparatus of Example 4 will now be described. FIG. 13 is a schematic configuration diagram of a machine control system using the emotion assessment apparatus of Example 4. The emotion assessment apparatus 104 of Example 4 has a data terminal 5 and an imaging unit 10. In the emotion assessment apparatus 104, the data terminal 5 assesses the emotion of a subject HK carrying out machine operation, and based on the results, the data terminal 5 sends a control signal to the machine 2 to help the subject HK to safely operate the machine. The imaging device 11 of the imaging unit 10 installed in the machine 2 takes images of the measuring region Sa of the subject HK who is operating the machine 2, and sends it to the data terminal 5. The data terminal 5 assesses the emotion of the subject HK from the received image data, and based on the assessment results, sends a control signal for control of the machine 2 to the receiver 220 of the machine 2. The receiver 220 inputs the received control signal into the controller 210 and the controller 210 controls the machine 2 according to the control signal. For example, when the emotion of the subject HK, as an operator, is an angry state, and it has been judged that the state of the operator is such that they cannot properly operate the machine 2, the data terminal 5 may send a control signal for forced stopping of the machine 2 to the machine 2. When forced stopping of the machine 2 instead has the potential to expose the subject HK to danger, a signal may be sent to raise a warning for the subject HK to return to a stable emotional state.

Figure 14:
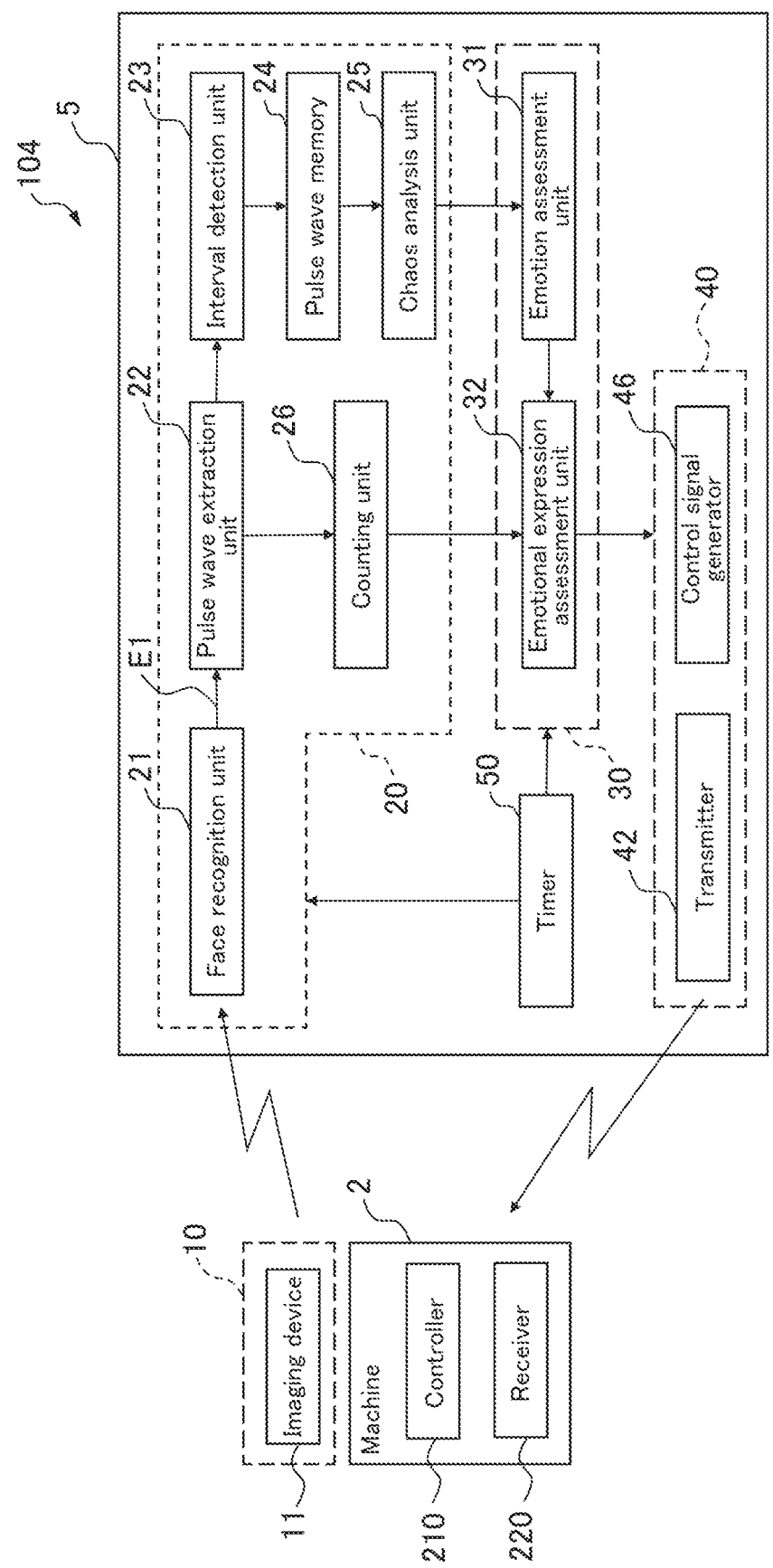
FIG. 14 is a block diagram for the emotion assessment apparatus of Example 4.

FIG. 14 is a block diagram for the emotion assessment apparatus 104 of Example 4. The data terminal 5 in the emotion assessment apparatus 104 of Example 4 comprises a control signal generator 46 that generates signals for control of the machine 2.

The control signal generator 46 generates control signals for control of the machine 2 based on the results of emotion assessment of the subject HK as assessed by the emotional expression assessment unit 32. For example, since it can be judged that there is no problem with continued operation of the machine 2 when the emotion of the subject HK operating the machine 2 is a stable state or an emotionally moved state, no control signal is generated for the machine 2 in this case. Alternatively, since it is judged that there is no problem with continued operation of the machine 2 by the subject HK, a signal may be generated for continued control of the machine 2.

On the other hand, when the emotion of the subject HK assessed by the emotional expression assessment unit 32 is an angry state and there is a risk that the operator (subject) may not be able to maintain safety if operation of the machine 2 is continued in that state, the control signal generator 46 generates a signal for forced stopping of the machine 2 or a signal to raise a warning to the operator, based on the emotion assessment results of the emotional expression assessment unit 32.

The control signal for the machine 2 generated by the control signal generator 46 is sent to the receiver 220 of the machine 2 via the transmitter 42. The receiver 220 of the machine 2 inputs the received control signal into the controller 210 and the controller 210 controls the machine 2 based on the control signal.

When the results of continuously assessing the emotion of the operator (subject) by the emotional expression assessment unit 32 indicate a change from an angry state to a stable state, the control signal generator 46 may generate a signal to resume operation of the machine 2, based on the results of emotion assessment by the emotional expression assessment unit 32, and may send the signal to the machine 2.

In this example, a control signal was sent by the data terminal 5 to the machine 2 based on the emotion assessment results for the operator (subject) from the data terminal 5, but there is no limitation to this method. For example, the emotion assessment results for the operator as assessed by the data terminal 5 may be sent to a management center that manages multiple machines 2, and the control signal for the machine 2 may be sent from the management center end. This will allow the management center to ascertain emotion assessment results for operators, for simultaneous health care management of the operator.

By using the emotion assessment apparatus of Example 4 for control of a machine based on the emotion assessment results for the operator, the safety of the operator can be ensured and the emotion assessment apparatus can be made to function as a near-miss sensor.

The Example described above used the emotion assessment apparatus as a data terminal, but there is no limitation to this usage. For example, when operation of the emotion assessment apparatus is carried out on a control board and applied to digital signage, the control board may be incorporated into the display device. In this case, the camera may be installed in the display device and the results of emotion assessment carried out on the control board may be sent to a server for statistical analysis at the server end.

Moreover, the aforementioned Examples used a portable terminal such as a smartphone as the imaging unit, but the faces of elderly persons may also be recognized using an eye-level camera as the imaging unit to take images of elderly subjects while providing care at a nursing home or the like, making emotion assessment based on the images acquired when caregivers meet with the elderly persons. The emotion assessment results may also be audio notifications. Specifically, notification of the emotion assessment results may be given by from an earphone worn by the caregiver or a tablet terminal speaker. When an eye-level camera is used the measurement target is on the line of sight, possibly making the emotion assessment results difficult to confirm on the screen of an eye-level camera, and therefore the emotion assessment results can be recognized from voice in such cases as well. When an eye-level camera is used as the imaging device, even though the eye-level camera is miniature and convenient for a cellphone, the throughput capacity is often inadequate, and therefore acquired images may be transmitted to another terminal by wireless connection for emotion assessment at the receiving terminal end.

Notification of the emotion assessment results by audio may be carried out with a machine control system using the emotion assessment apparatus of another Example, such as Example 4. Audio notification of emotion assessment results and warnings allows emotion assessment results and warnings to be recognized audibly even when the machine operator is concentrating on work and has not looked at the control screen.

A camera-equipped smart watch may be used as an alternative imaging device. The images taken by a smart watch may be used for emotion assessment by the smart watch itself, or the images may be sent to another terminal for emotion assessment at the receiving terminal end.

EXAMPLE 5

(Simultaneous Measurement of Multiple Persons)

The frequency of occasions of web conferencing via the internet and intranet have been increasing in recent years. Examples of web conferencing include presentations by companies to multiple customers via the internet, and internet classes for multiple students conducted by teachers. It is preferred if the hosts of web conferences, such as companies or teachers, can ascertain whether or not multiple students such as multiple customers or pupils are giving their attention to the speaker, or whether the presentation or class is proceeding in a satisfactory fashion. Because lecture students are participants to the lecture, "students" will be referred to hereunder as "participants".

For seminars using the Web, however, similar to the web conferencing of Example 2, the teacher does not look at the faces of the multiple participants directly but rather looks at the faces of the multiple participants through the screen, and it is therefore difficult for the seminar host to ascertain the state in which each participant is listening. The various types of events that a web conferencing host provides for participants, such as a "presentation", "class" or "seminar", will all be referred to as "lectures" throughout the present specification.

The emotion assessment apparatus of Example 5 of the disclosure is designed so that, even with multiple participants, it is possible to ascertain the state in which the multiple participants are listening. The emotion assessment apparatus of Example 1 of the disclosure carries out emotion analysis of a single subject, while the emotion assessment apparatus of Example 5 carries out simultaneous emotion analysis of multiple subjects. The emotion assessment apparatus of Example 5 also calculates the optimal listening time, which represents the time that the participant is listening in the optimal state as described below, and assesses in what state the participant was listening.

Figure 15:
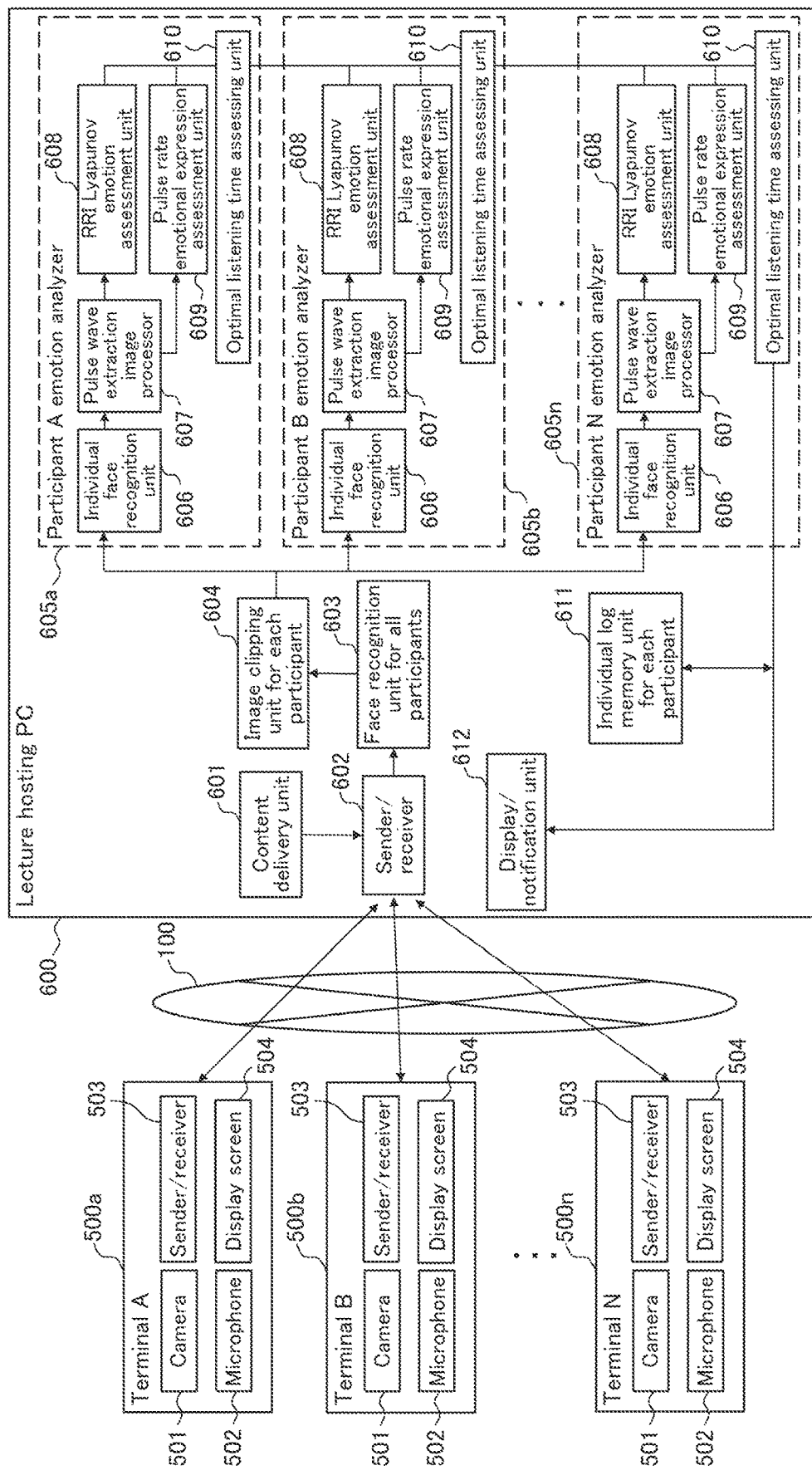
FIG. 15 is a block diagram for a lecture hosting PC, as the emotion assessment apparatus of Example 5.

An example in which a lecture host is conducting a lecture for multiple participants will now be described as an example of the emotion assessment apparatus of Example 5 according to the disclosure. Specifically, the subjects are students (participants) attending a lecture. FIG. 15 is a block diagram for a lecture hosting PC 600, as the emotion assessment apparatus of Example 5. The lecture hosting PC 600 sends and receives data between terminal A (500a), terminal B (500b), . . . terminal N (500n) used by multiple participants: participants A, participant B, . . . participant N while attending the lecture, by way of the internet 100.

Terminal A (500a) comprises a camera 501, a microphone 502, a sender/receiver 503 and a display screen 504. The camera 501 takes images of the face of the participant A. The microphone 502 collects audio from participant A. The camera 501 and microphone 502 may be built-in to the terminal A (500a) or external. The sender/receiver 503 sends and receives data to and from the lecture host end PC 600 via the internet 100. The display screen 504 displays information relating to the lecture that is sent from the lecture host end PC 600. The display screen 504 may also display an image of the face of the teacher who is hosting the lecture, and an image of the face of participant A. The configurations of terminal B (500b) and terminal N (500n) are the same as the configuration of terminal A (500a).

The lecture host end PC 600 has a content delivery unit 601, a sender/receiver 602, a face recognition unit for all participants 603, an image clipping unit for each participant 604, participant emotion analyzers (605a, 605b, . . . 605n), an individual log memory unit for each participant 611 and a display/notification unit 612.

The content delivery unit 601 delivers content such as videos and images used in the lecture by the teacher hosting the lecture, at the predetermined timings. The content may be delivered by the teacher in real time, or it may be delivered by playback of video prepared beforehand.

Figure 16:
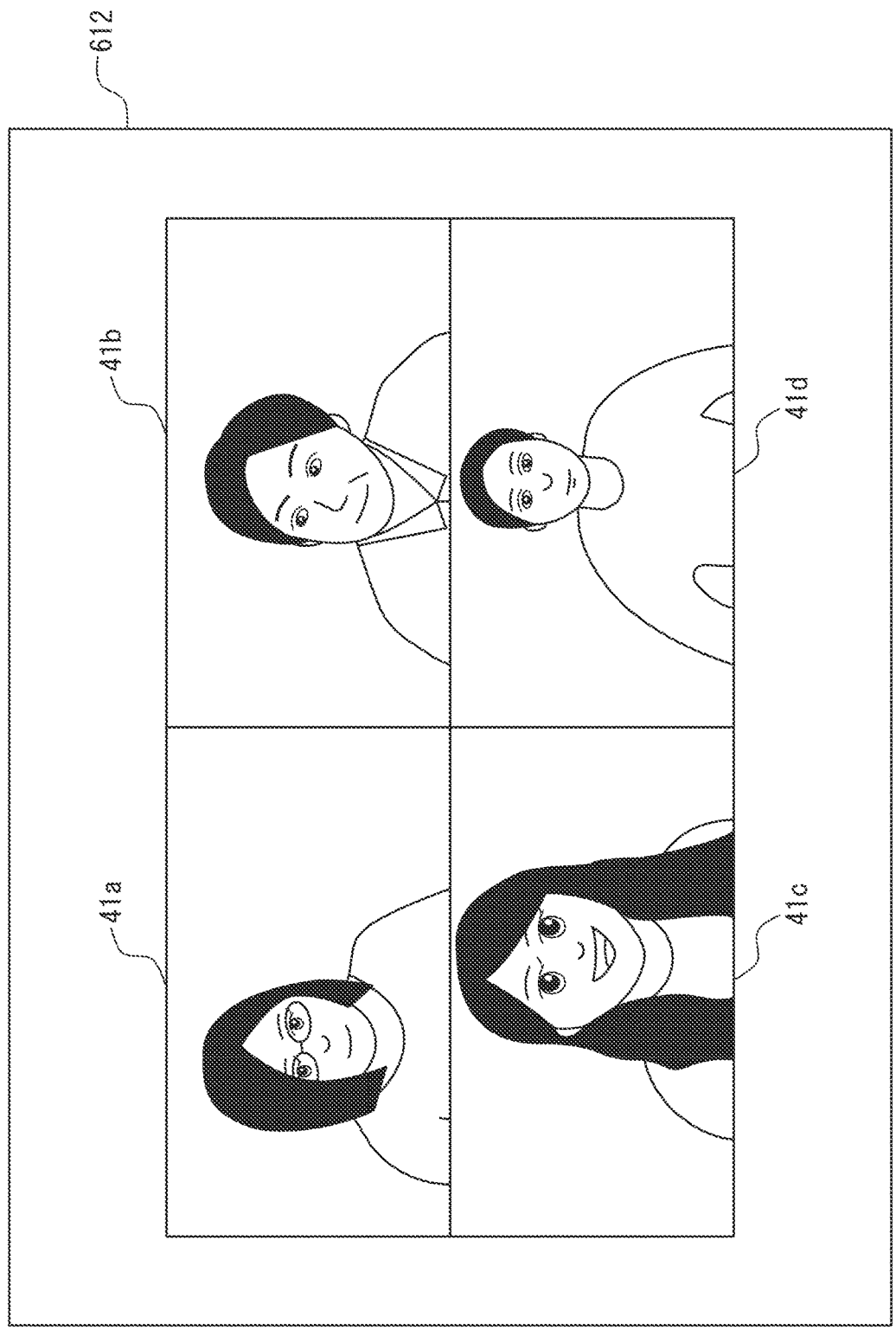
FIG. 16 is an example of image display of participants, for a case with multiple participants.

The sender/receiver 602 receives data containing images of the faces of participant A, B, . . . N from the terminal A (500a), terminal B (500b), . . . terminal N (500n) via the internet 100. For example, when 4 participants are attending the lecture, images of the participants (41a to 41d) are each displayed on the screen of the display/notification unit 612, as shown in FIG. 16. The number of participants in FIG. 16 is 4, but this is not limitative.

The face recognition unit for all participants 603 recognizes the images of the faces of all of the multiple participants. That is, the face recognition unit for all participants 603 is an example of a photographing unit that can photograph the faces of multiple subjects. Application software used for web conferencing during lectures is usually not provided with a function for recognizing where the faces of participants appear on the screen, and the number of participants is also unclear. For example, even if the terminals (500a, 500b, . . . 500n) are connected to the lecture hosting PC 600, it cannot be recognized that participants are listening if the images of participant faces are not being sent. Therefore the face recognition unit for all participants 603 takes in images displayed by application software, first scanning the general locations of faces to ascertain how many participants are present. The face recognition unit for all participants 603 also acquires face location coordinates for each of the multiple participants. The method of facial recognition is described below.

Figure 17:
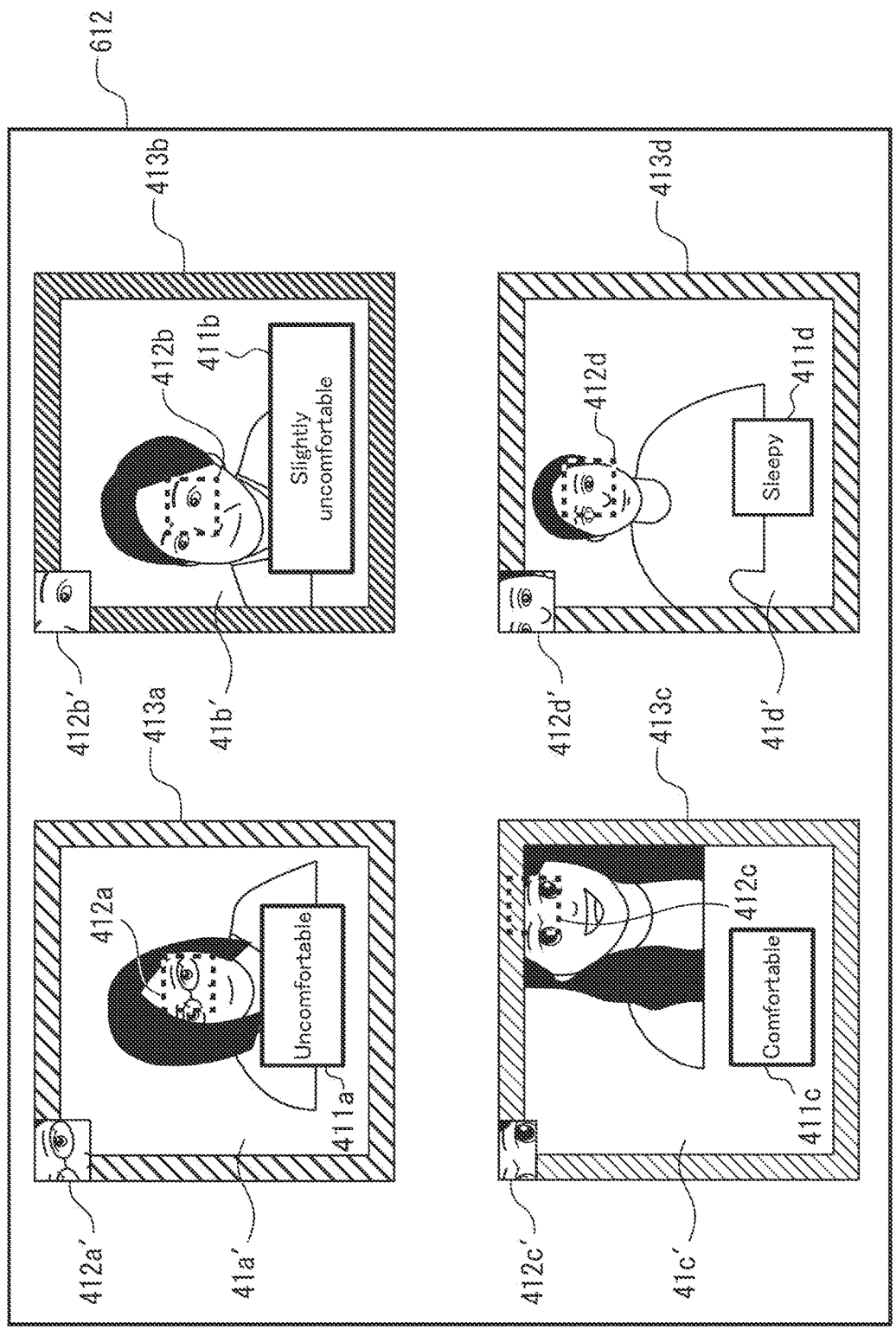
FIG. 17 is an example of image display for a case where partial images are cut out from the facial images of multiple participants.

The image clipping unit for each participant 604 clips out images to be used for pulse wave analysis, from the acquired participant images. This is done to reduce the volume of data used for image processing, because in the case of multiple participants the volume of data for image processing increases and makes simultaneous parallel processing more difficult. FIG. 17 shows an example of clipping a partial image from a facial image of a participant. The image clipping unit for each participant 604 clips a part 41a' of the image 41a of the participant A, as shown at top left in FIG. 17, for example. Similarly, the image clipping unit for each participant 604 clips parts (41b', 41c', 41d') of the images (41b, 41c, 41d) of the other participants B to D.

The emotion analyzer 605a of participant A has an individual face recognition unit 606, a pulse wave extraction image processor 607, an RRI Lyapunov emotion assessment unit 608, a pulse rate emotional expression assessment unit 609, and an optimal listening time assessing unit 610.

The individual face recognition unit 606 of the emotion analyzer 605a of participant A carries out facial recognition of participant A. The individual face recognition unit 606 clips out a region for extraction of a pulse wave from the image 41a' of the face of participant A. For example, a portion 412a is clipped out from the image 41a' of participant A shown at top left in FIG. 17. The clipped image 412a may be displayed at top left of the image 41a' of the participant A, for example (412a'). Similarly, the individual face recognition units 606 of the emotion analyzers (605b, 605c, 605d) of the other participants (B, C, D) carry out facial recognition of the other participants (B, C, D), respectively. The individual face recognition unit 606 of the emotion analyzers (605b, 605c, 605d) of the other participants (B, C, D) clip out regions for extraction of pulse waves from the images (41b', 41c', 41d') of the faces of the other participants (B, C, D). For example, portions (412b, 412c, 412d) of the images (41b', 41c', 41d') of the other participants (B, C, D) are clipped out. The clipped images (412b, 412c, 412d) may be displayed at top left of the images (41b', 41c', 41d') of the other participants (B, C, D), for example ((412b', 412c', 412d'). The method of clipping the images will be described below. Predetermined parts of the images (such as the facial portions of the images) are clipped out from among the entire participant images and used for image processing, to help reduce the volume of data processing during image processing.

The pulse wave extraction image processor 607 is an example of a detecting unit, and it uses the image 412a in a prescribed range of the facial image 41a' of the participant A that has been clipped out by the individual face recognition unit 606, to detect heartbeat information including the heart rate of the participant A, as the subject.

The pulse wave extraction image processor 607 functions as the counting unit explained in Example 1, counting the number of heart rate variations for transition from a state below the average heart rate to a state above the average heart rate, where heart rate increase is above a predetermined value during a predetermined time period.

The RRI Lyapunov emotion assessment unit 608 is an example of an emotion assessment unit, and it assesses whether the emotion of the participant A as the subject is a negative emotion or a positive emotion, based on heartbeat information detected by the pulse wave extraction image processor 607. RRI is an abbreviation for "R-R Interval" and represents the heartbeat or pulse wave interval. The RRI Lyapunov emotion assessment unit 608 corresponds to the 5 blocks comprising the pulse wave extractor 22, interval detector 23, pulse wave memory 24, chaos analyzer 25 and emotion assessment unit 31 in FIG. 2 of Example 1. It is generally said that a participant listening to a lecture exhibits maximum performance when the participant has a level of psychological "mild nervousness" while listening in a state that will be referred to as "peace of mind". In other words, the best state of the participant is not necessarily a lack of stress, but rather having a certain degree of "mild nervousness". A state of "mild nervousness" for a participant is a state in which the participant has "slightly negative emotion", i.e. a state in which the participant has a "slightly uncomfortable emotion". If the RRI Lyapunov emotion assessment unit 608 judges whether or not the participant has a "slightly negative emotion", then it can judge whether or not the participant has "slightly uncomfortable emotion", i.e. whether or not the participant has "mild nervousness".

Figure 18:
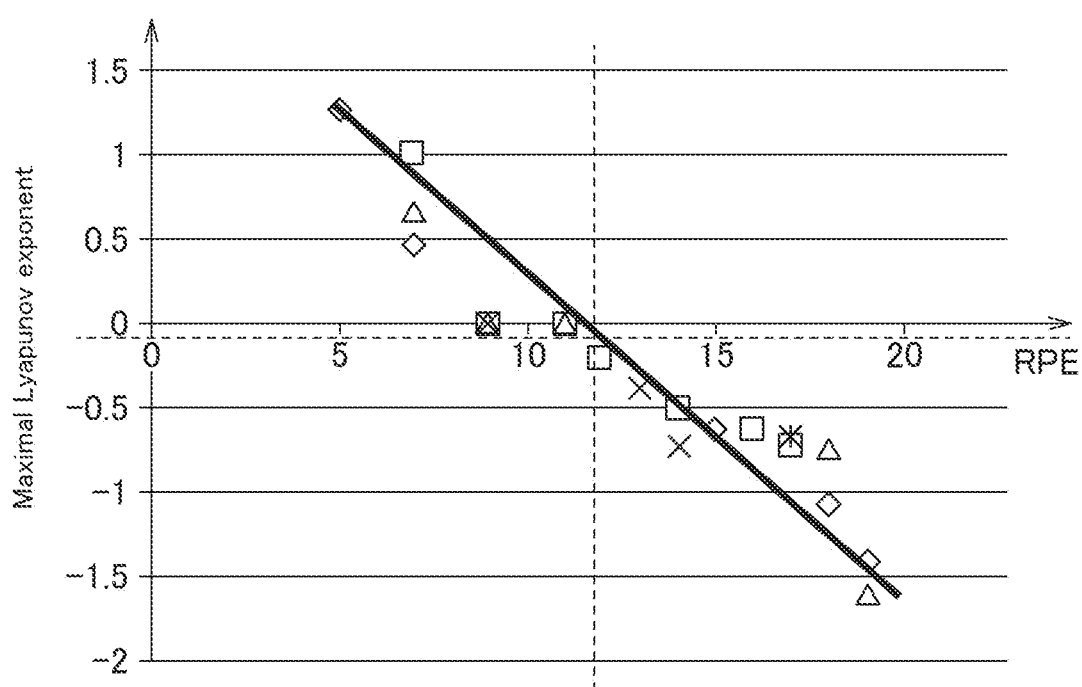
FIG. 18 is a graph showing the relationship between maximal Lyapunov exponent and Rating of Perceived Exertion RPE.

FIG. 18 shows the relationship between maximal Lyapunov exponent and Rating of Perceived Exertion (RPE). FIG. 18 is a graph plotting maximal Lyapunov exponent and heart rate difference measured from heartbeat information during different times of fatigue of different persons, against assessed RPE for 5 subjects, as one example. RPE is an index for numerical representation of subjective difficulty and fatigue during training and movement. The Borg scale is generally used to represent hardness of exertion on a scale of 6 to 20 for digitization of RPE. A correlation is seen between maximal Lyapunov exponent and RPE in FIG. 18, and the RPE value can be calculated from the maximal Lyapunov exponent calculated by the RRI Lyapunov emotion assessment unit 608. For example, a maximal Lyapunov exponent of 0 corresponds to RPE of 12, and a maximal Lyapunov exponent of −0.7 corresponds to RPE of 15.

Figure 19:
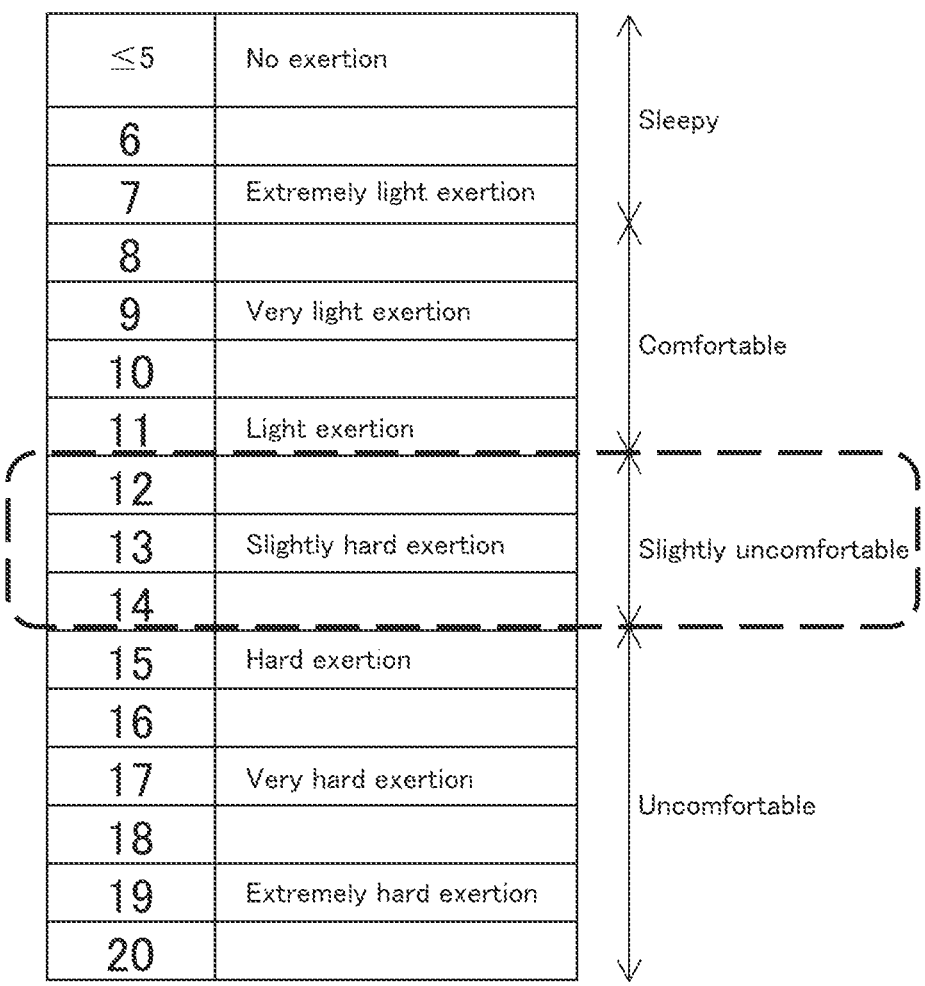
FIG. 19 is a Borg scale showing the relationship between RPE and perceived difficulty/exertion during training or exercise.

FIG. 19 shows the Borg scale. In the Borg scale, a subject with RPE of 12 to 15 is described as feeling "slightly hard exertion", such a state being thought to produce "mild nervousness" in a lecture participant as the subject. With RPE of 5, the subject has "no exertion", and with RPE of 6 to 7 the subject feels "extremely light exertion", such a state being thought to produce a feeling of "sleepiness" in a lecture participant. With RPE of 8 to 9, the subject has "very light exertion", and with RPE of 10 to 11 the subject feels "light exertion", such a state being thought to produce a feeling of "pleasantness" in a lecture participant. With RPE of 15 to 16, the subject has "hard exertion", with RPE of 17 to 18 the subject feels "very hard exertion" and with RPE of 19 to 20 the subject feels "extremely hard exertion", such a state being thought to produce a feeling of "discomfort" in a lecture participant.

Figure 20:
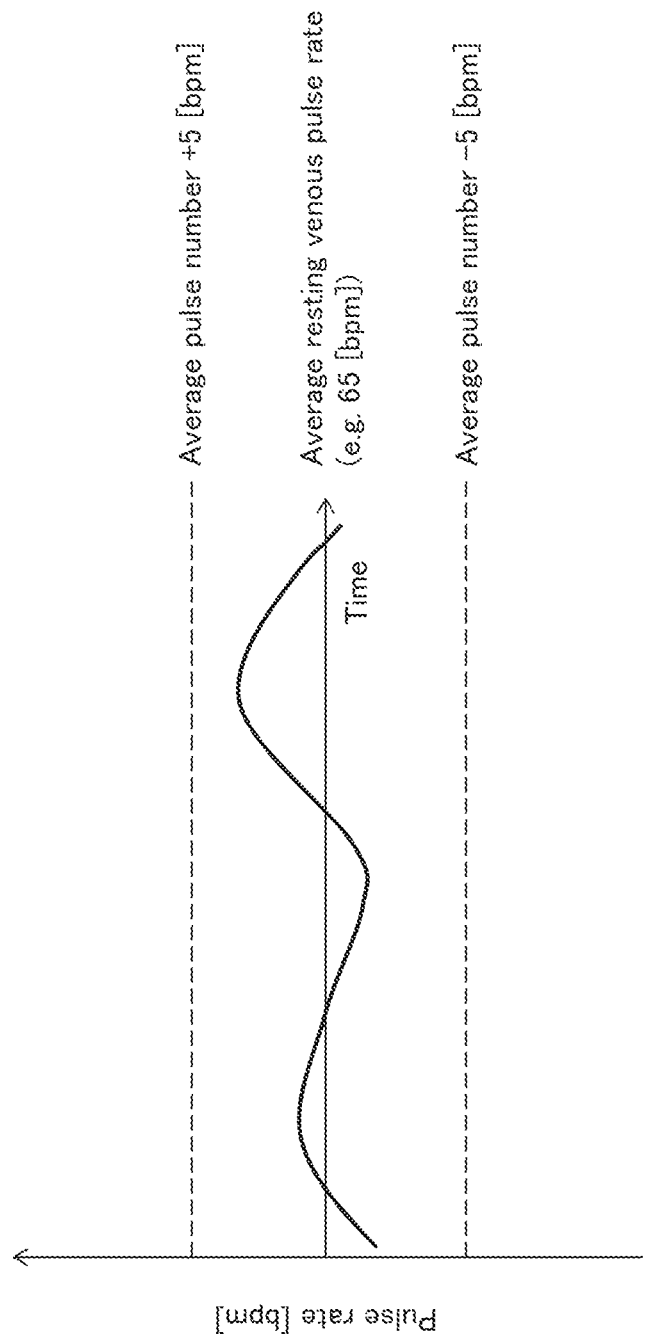
FIG. 20 is an example of time-dependent change in pulse rate, for a case where the pulse wave is within a predetermined range from the average resting venous pulse rate.

The pulse rate emotional expression assessment unit 609 assesses the emotional expression of the participant based on whether or not the extracted pulse wave is within a predetermined range from the average resting venous pulse rate. FIG. 20 is an example of time-dependent change in pulse rate, for a case where the pulse wave is within a predetermined range from the average resting venous pulse rate. The aforementioned state in which a participant has "peace of mind" is thought to be a state in which the pulse wave is calmed within the predetermined range from the average resting venous pulse rate. For example, the participant may be judged to have peace of mind if the pulse of the participant is within a range of plus or minus 5 [bpm], for example, around the average resting venous pulse rate as the center. The average resting venous pulse rate may be 65 [bpm], as the average resting venous pulse rate for Japanese, or the average resting venous pulse rate for individual participants may be used.

Analysis of emotion and emotional expression is preferably continuous analysis during the lecture attendance period. When the Lyapunov exponent used for emotion analysis is updated every 30 to 40 seconds, for example, the emotional expression analysis may also be matched to that timing, for analysis every 30 to 40 seconds.

The optimal listening time assessing unit 610 is an example of an emotional expression assessment unit, and it assesses the mental state of participants, as subjects, based on the number of heart rate variations counted by the pulse wave extraction image processor 607, while also using the assessment results from the RRI Lyapunov emotion assessment unit 608, as the emotion assessment unit, for assessment of mental state. The optimal listening time assessing unit 610, as an emotional expression assessment unit, assesses whether or not mental state is optimal while attending a lecture, based on the number of heart rate variations and the assessment results from the RRI Lyapunov emotion assessment unit 608, as the emotion assessment unit. In other words, when the participant satisfies both a first condition in which the positive/negative emotion is "slightly uncomfortable" indicating "mild nervousness", and a second condition in which the pulse is "within a predetermined range from the average pulse" indicating that the participant emotional expression state is "peace of mind", it is judged that the participant is in the optimal mental state. The time during which the participant is listening to the lecture in the optimal mental state is summed and the cumulative time is recorded as the optimal listening time. A longer optimal listening time corresponds to a longer time that the participant is listening to the lecture in the optimal state. The optimal listening time can be summed separately for each participant. The total value for the optimal listening times of multiple participants may also be divided by the number of participants to calculate the average. The optimal listening time is expected to be longer if the content of the lecture by the teacher is interesting for the participant, the optimal listening time can be used as an indicator for the competence of the teacher.

The emotion analyzer 605b for participant B and the emotion analyzer 605n for participant N have the same configuration as the emotion analyzer 605a for participant A.

The individual log memory unit for each participant 611 stores emotion and emotional expression for each of the multiple participants in a time series, from the start point until the end point of the lecture, or until the participant leaves. By referring to the log it is possible to know during what part of the lecture the participant was listening in the optimal state. Alternatively, since it can be known during what portions of the lecture a participant has felt sleepy by referring to the log, it is possible to know after the lecture what portions of the lecture contained explanations that were likely to cause sleepiness.

The display/notification unit 612 is an example of an output unit, and it outputs the assessment results of the RRI Lyapunov emotion assessment unit 608 and pulse rate emotional expression assessment unit 609. For example, as shown in FIG. 17, the positive/negative emotion assessment results 411a to 411d from the RRI Lyapunov emotion assessment unit 608 may be represented as characters at the bottom of the facial images of each of the multiple participants, and the assessment results 413a to 413d for emotional expression from the pulse rate emotional expression assessment unit 609 may be represented as rectangular frames around the facial images of the multiple participants.

In the example shown in FIG. 17, the positive/negative emotion assessment results 411a to 411d indicate that the emotion of the participant A is "uncomfortable", the emotion of the participant B is "slightly uncomfortable", the emotion of the participant C is "comfortable", and the emotion of the participant D is "sleepy". When displaying the characters, the character colors may be different to correspond to positive/negative emotion. For example, since it is normal to feel slightly nervous when attending a lecture, the positive/negative emotion expression may be indicated by showing "somewhat negative emotion" with "green characters" (safe color), and "negative emotion" with "red characters" (warning color). Extreme positive emotion tends to evoke sleepiness, and may therefore be shown with "black letters" indicating "sleepiness".

In the example shown in FIG. 17, from the assessment results 413a to 413d for emotional expression it is possible to represent whether the pulse of a participant is in the predetermined range or has exceeded the predetermined range, or has fallen below the predetermined range, with respect to the average resting venous pulse rate. For example, when the pulse of the participant A is within the resting venous pulse rate range (average pulse ±5 [bpm]), the frame for the emotional expression assessment result 413a may be shown with "green" color. In this case, the lecture host may recognize that participant A is in a "peace of mind" state, based on the fact that the emotional expression assessment result 413a is shown in green. When the pulse of participant B is below the resting venous pulse rate range, the frame for the emotional expression assessment result 413b may be shown with "black" color, for example. When the pulse of participant C is above the resting venous pulse rate range, the frame for the emotional expression assessment result 413c may be shown with "red" color, for example. When the pulse of participant D is within the resting venous pulse rate range, the frame for the emotional expression assessment result 413d may be shown with "green" color, for example. The colors for the frames of the emotional expression assessment results 413a to 413d may also be intermediate colors corresponding to the pulse rate, instead of simple colors.

This method for displaying the positive/negative emotion and emotional expression assessment results is merely an example, and the positive/negative emotion and emotional expression assessment results may optionally be displayed by a different display method. For example, the positive/negative emotion assessment results may be displayed using face marks corresponding to emotion. The emotional expression assessment results may also be displayed using characters or numerals corresponding to the pulse rate. The lecture host can refer to the positive/negative emotion assessment results and emotional expression assessment results to easily judge the state of each participant attending the lecture.

The optimal listening time for each participant may also be separately calculated and shown to each participant to allow the participant to easily ascertain their own listening state. The optimal listening time may also be summed for each participant and the optimal listening time for all of the participants may be totaled and divided by the number of participants attending the lecture to calculate the average, thus allowing calculation of the overall optimal listening time for the lecture. Since the lecture hosting time lasts for a predetermined time period such as 1 hour or 2 hours, the optimal listening time may be divided by the lecture hosting time to calculate the standard value per unit time. For example, if the cumulative value for the optimal listening time is 12 minutes for a 60-minute lecture, the optimal listening time per hour for the lecture overall may be calculated to be 20%.

Figure 21:
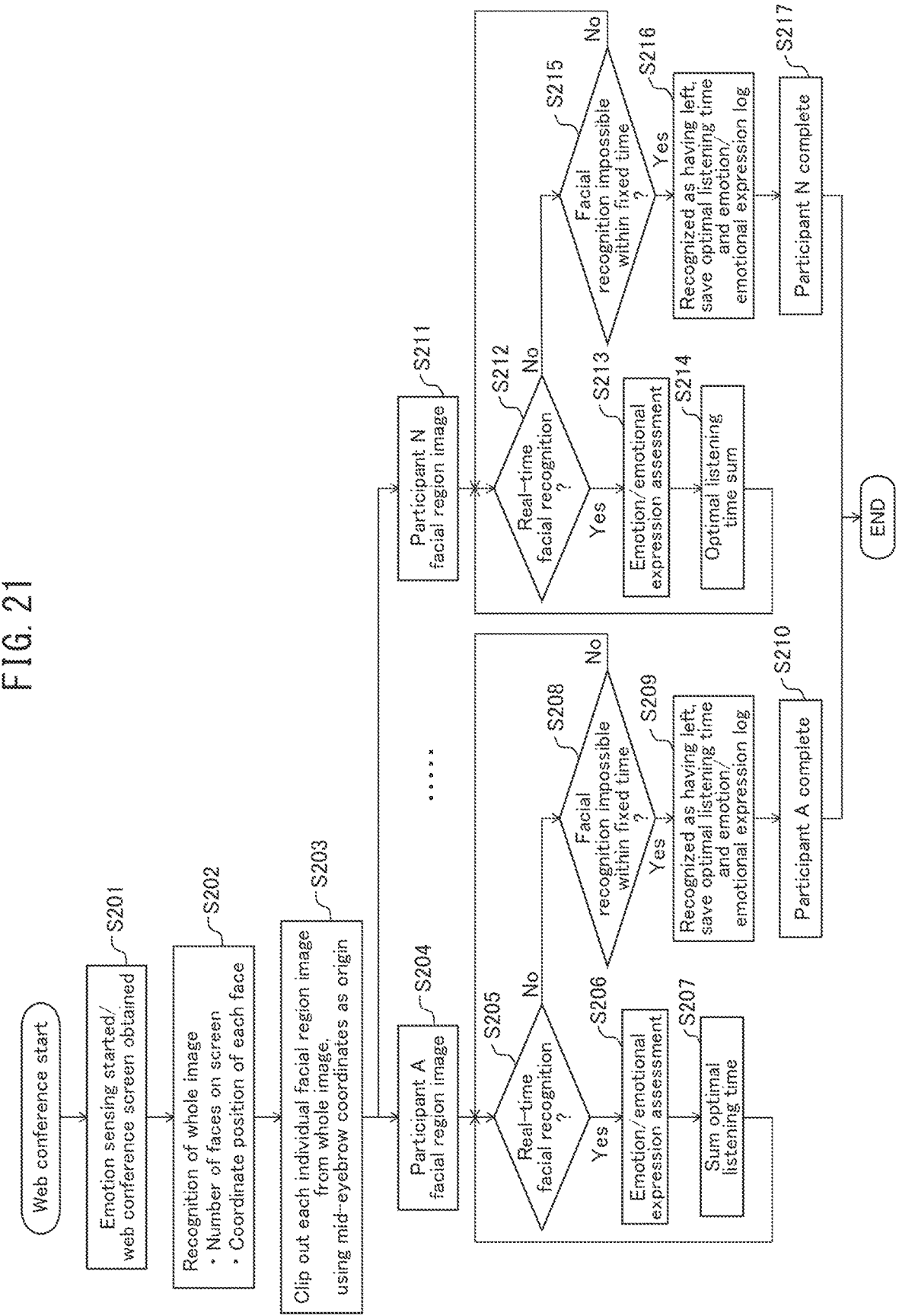
FIG. 21 is a flow chart illustrating the operation sequence for the emotion assessment apparatus of Example 5.

FIG. 21 is a flow chart illustrating the operation sequence for the lecture hosting PC 600 as an emotion assessment apparatus of Example 5. First, in step S201, a program is launched for emotion sensing, and a web conferencing screen is obtained. A case where multiple participants are taking part in a web conference will now be explained. Images of the multiple participants are displayed on the web conferencing host PC screen. Web conferencing software may be used to display only the faces of the participants on a different monitor from the monitor displaying the lecture content, for example. When an explanation is being made while sharing content on the screen during web conferencing, the content will sometimes be displayed on the entire screen, making it impossible to show the faces of the participants. When the facial expressions of the participants cannot be seen it is not possible to view the reactions of participants during explanation by the web conferencing host, and therefore it cannot be judged whether the participants are understanding the spoken content. Therefore, the software executed by the web conferencing may include a function allowing addition of a separate screen from the PC screen displaying the content, or allowing the screen to be split. Using such a function allows facial images for multiple participants to be displayed on a single screen, or allows a shared screen to be displayed on another screen. Arranged display of multiple participants on a single screen allows the web conferencing to be conducted while confirming the facial expressions of the multiple participants.

Next, in step S202, the facial images are all recognized and the number of participant faces on the screen is counted, calculating the coordinate location of each face. As mentioned above, a screen displaying all of the participants is obtained, and all of the facial images are initially recognized. Since each participant sometimes changes their position in the screen, the facial images of all of the participants are recognized at predetermined times, such as about 1 minute. Recognition of the facial images of all of the participants means counting the number of recognized facial images and calculating the coordinate positions where the faces were recognized in the screen. For the coordinate positions in the facial images, the coordinate positions of the eyes and nose may be calculated, and predetermined coordinate positions in the facial images, such as coordinates between eyebrow positions, for example, may be used as reference positions for each participant. When a participant face has been taken with a camera, since the actual position of the face moves slightly, images may be taken at predetermined intervals such as 1 minute, for example, and with the participant region defined to be within a predetermined pixel count (such as 300 pixels) for XY on the XY coordinate system, the same person may be identified even if the coordinates vary in the facial image within that range.

In the next step S203, the facial region image is clipped out from the whole image, using the mid-eyebrow coordinates as the origin. As shown in FIG. 17, for example, a region of likely variation of the facial position of the participant using the mid-eyebrow coordinate position as the origin, such as a region of plus or minus 300 pixels in the XY direction around the mid-eyebrow coordinate position as the center, is clipped out, and the clipped image is used as the image for assessment of emotion and emotional expression.

In the next step S204, the facial region image of participant A is acquired and the image is recognized.

In the next step S205, it is judged whether or not the facial image could be recognized in real time. When the facial image of the participant A could be recognized, emotion and emotional expression assessment are carried out in step S206, the optimal listening time is summed in step S207, and then the flow is returned to step S205 and it is judged whether or not the facial image could be recognized in real time. Because calculation of the maximal Lyapunov exponent for emotion assessment requires a certain period such as about 60 seconds, and emotional expression assessment is also being carried out simultaneously, the optimal listening time is calculated every 60 seconds, for example.

When the facial image of the participant A could not be recognized in step S205, it is then judged in step S208 whether or not the facial image could be recognized during a given time period. When the facial image could be recognized within the given time period in step S208, flow returns to step S205 where it is judged whether or not the facial image can be recognized in real time.

When the facial image could not be recognized within a given time period (such as 3 minutes) in step S208, on the other hand, the participant A can be judged to have left, and it is judged in step S209 that the participant A has left, storing the log of the optimal listening time, the emotion assessment results and the emotional expression assessment results. The inability to recognize the facial image of participant A includes cases where participant A has left the location of terminal A that participant A has connected with the lecture host end PC for web conferencing, while still maintaining a connected state, as well as cases where the connection between terminal A of the participant A and the lecture host end PC has been cut off, as well as after the lecture has ended.

In the next step S210, summing of the optimal listening time for participant A is completed. The process from steps S204 to S210 includes summing the optimal listening time for participant A, but the same processing is simultaneously carried out in parallel for the other participants as well, and their optimal listening times are summed. For example, steps S211 to S217 are carried out for participant N to sum the optimal listening time for participant N. This also applies for the other participants such as participant B.

The foregoing explanation was for an example where it is judged whether each of multiple participants is listening to the lecture or has left, and the optimal listening time is summed after each has left, but there is no limitation to this method, and instead the cumulative time may be summed for the optimal listening times at the end point of the web conference, when the facial images of all of the participants can no longer be recognized.

(Facial Image Recognition)

Figure 22:
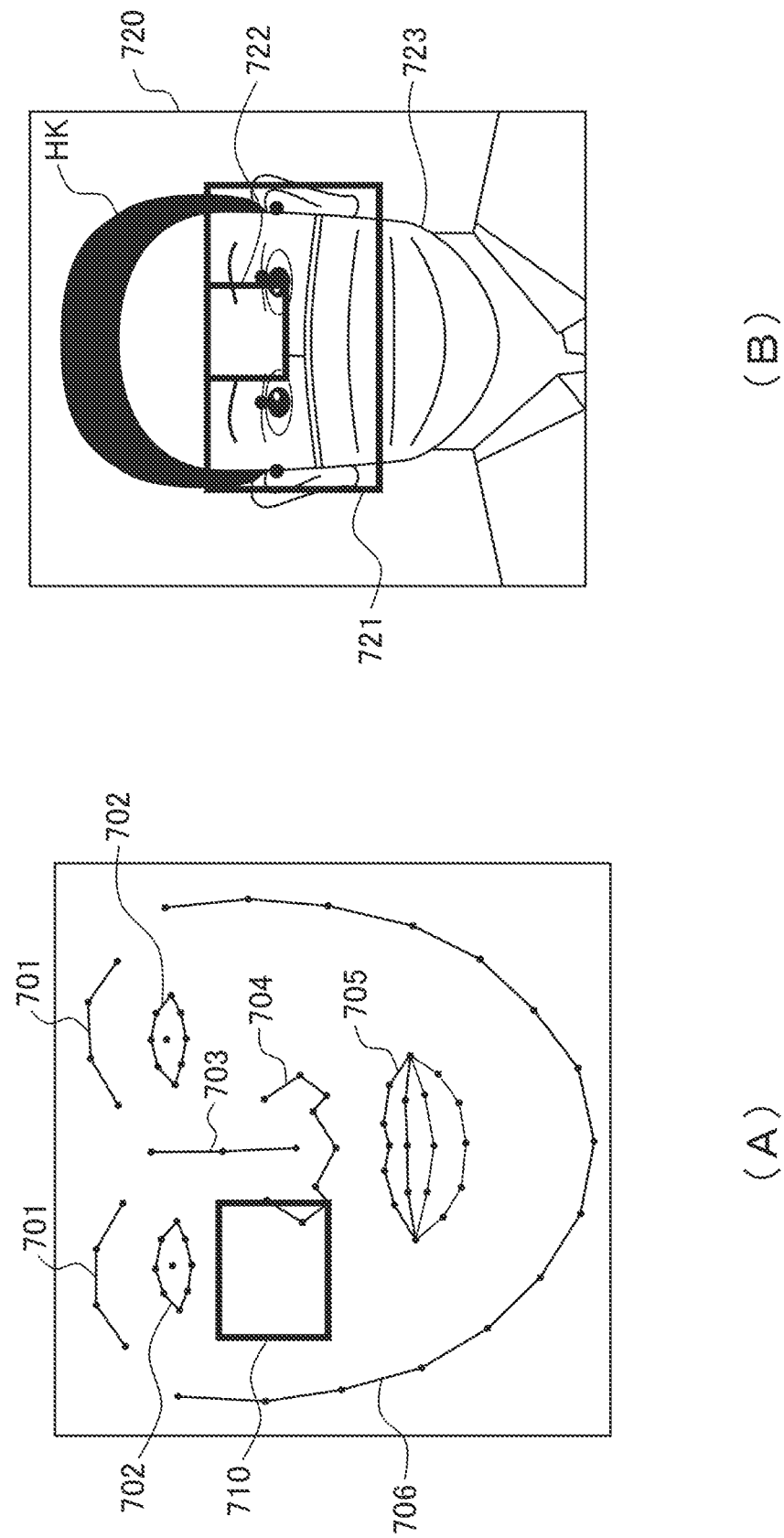
FIG. 22(A) is an example of output from a feature coordinate fitting method in which feature coordinates are extracted from a facial image.
FIG. 22(B) is an example of output from a method of detecting the location between eyebrows from a photographed facial image.

A method of recognizing facial images of subjects will now be explained. FIG. 22(A) shows an example of output from a feature coordinate fitting method in which feature coordinates are extracted from a facial image, and FIG. 22(B) shows an example of output from a system that detects the location between eyebrows from a photographed facial image.

FIG. 22(A) is an example in which the coordinate positions of the eyebrows 701, eyes 702, nose bridge 703, nose 704, mouth 705 and face outline 706 are extracted from a facial image of a subject, and an image clipped out for emotion assessment and emotional expression assessment is used as a predetermined region 710 of the cheek. This method is effective when the subject is not wearing a mask, but since a mask covers parts of the mouth, nose and facial outline it can prevent accurate measurement of the coordinate positions.

A method may therefore be used for clipping out specific regions of a facial image of a subject regardless of whether or not a mask is worn, as shown in FIG. 22(B), whereby image recognition is carried out by deep learning using an image 721 of eyes and facial outlines, and the facial image 720 of the subject HK is clipped to produce an image for emotion assessment and emotional expression assessment of the specific region 722 from the mid-eyebrow region to the temples. The location of the face used for image recognition is not limited to the eyes and outline and may instead be another location, but a location is preferred that is not covered by the mask 723 so as to allow image recognition even when the mask 723 is worn. In addition, the region clipped for emotion assessment and emotional expression assessment is not limited to the area between eyebrows, and may be the forehead, for example. The lecture hosting PC 600, as an emotion assessment apparatus, preferably has measuring location identifying means that identifies faces from a screen in which multiple persons are displayed, and identifies the measuring locations for the identified faces. The image clipping unit for each participant 604 is an example of measuring location identifying means. The pulse wave extraction image processor 607, as a detecting unit (see FIG. 15), allows heartbeat information to be acquired based on changes in the image of the measuring location of each face.

When a specific region such as the eyes or facial outline in a facial image is extracted from the image by deep learning, the computational volume increases, potentially putting a load on the processor that controls the lecture hosting PC 600 serving as the emotion assessment apparatus. In order to reduce the processing volume at the processor of the lecture hosting PC 600, image processing by deep learning may be carried out at the backend, thereby speeding the processing.

(Image Uptake by HDMI)

When using software linked with web conferencing in which emotion assessment is carried out in this manner using images of subjects, it is commonly intended for company in-house use, and emotion sensing cannot be carried out on a web conferencing PC in some cases due to security concerns. For example, since an emotion assessment program directly loads image information and captures the web conferencing screen, using it in an in-house personal computer can invite infection with computer viruses or may be recognized as a program with illegal access. HDMI output is an image outputting method that can be used without intranet constraints. Since HDMI video output can be outputted from an intranet similar to HDMI output from a PC to a projector, the HDMI output can be utilized for loading facial image data for a subject into a personal computer on an intranet, allowing emotion assessment to be carried out.

Figure 23:
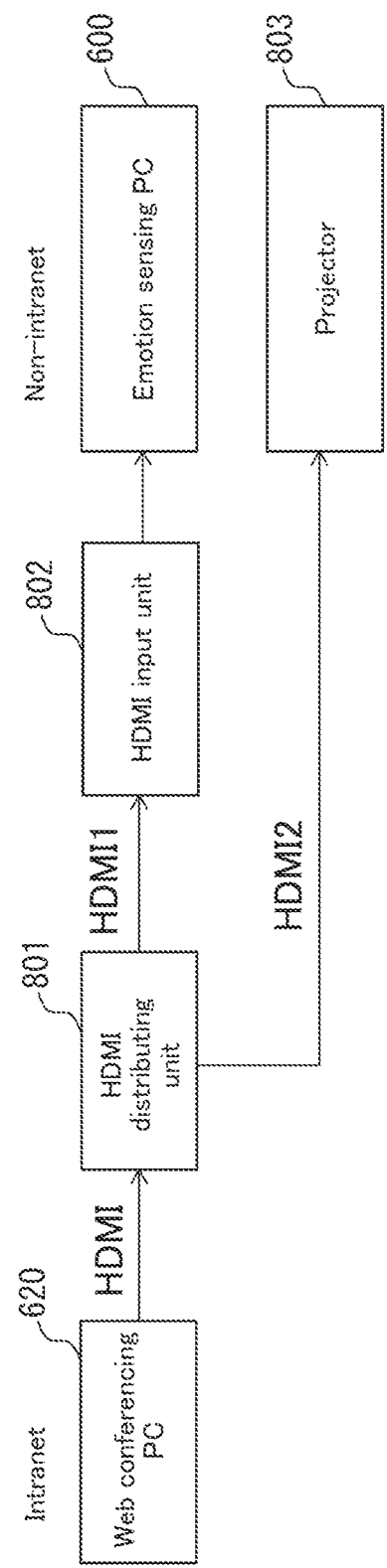
FIG. 23 is a configuration example for carrying out image capture using HDMI$^R$ output.

FIG. 23 shows a configuration example for carrying out image capture using HDMI output. The web conferencing PC 620 is connected to an intranet. The HDMI output from the web conferencing PC 620 is inputted into an HDMI distributing unit 801. The HDMI distributing unit 801 outputs and distributes an HDMI signal inputted from the web conferencing PC 620 to "HDMI1" and "HDMI2". HDMI1 is inputted into an HDMI input unit 802, and inputted into an emotion sensing PC 600 for emotion sensing. The emotion sensing PC 600 is not connected to the intranet (non-intranet). The emotion sensing PC 600 can utilize facial image data for a subject included in the HDMI output to carry out emotion sensing without connection to the intranet. The HDMI2 is inputted to a projector for display of the images of the web conferencing PC 620.

In this example, web conferencing images alone were loaded into an emotion sensing PC 600, as a non-intranet PC, from the HDMI output of a web conferencing PC 620 as an intranet PC, and emotion analysis was carried out at the emotion sensing PC 600, but there is no limitation to this example. That is, the HDMI output may be utilized for emotion sensing at the web conferencing PC 620 conducting the web conference. Moreover, the explanation was for an example of HDMI output as a type of video output loaded into a non-intranet PC that is not connected to the intranet, from a PC that is connected to the intranet, but there is no limitation to this example. In other words, the output method used may be one other than HDMI output, for loading of video output to a non-intranet PC from a PC connected to the intranet.

EXAMPLE 6

(Assessment of Causes of Elderly Communication Obstacles)

Figure 24:
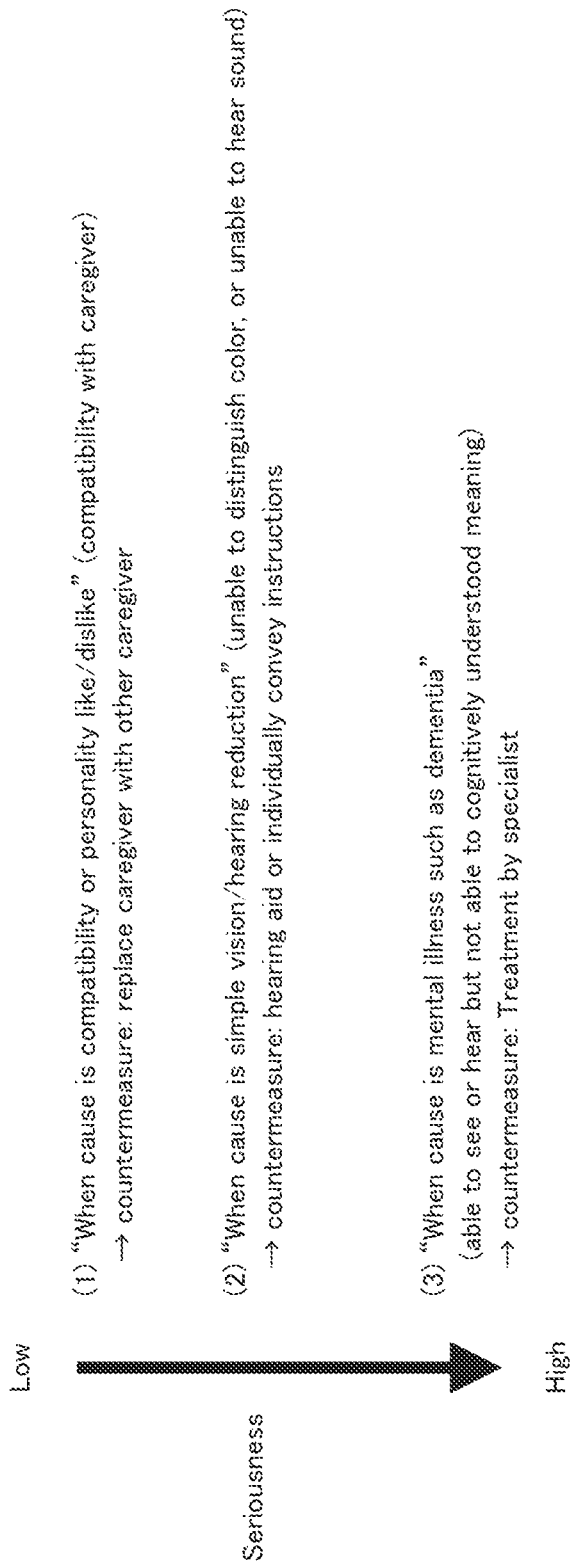
FIG. 24 shows examples of causes of and countermeasures against obstacles to communication between elderly persons and caregivers.

Troubles sometimes occur during communication between elderly persons and caregivers. Such troubles may be due to inability of the caregiver to assess factors that create obstacles to communication with elderly persons. FIG. 24 shows examples of causes of and countermeasures against obstacles to communication between elderly persons and caregivers. Causes of obstacles to elderly communication are thought to be the causes (1) to (3), in general order from low seriousness.
  (1) The first cause is that an elderly person may have a personal dislike of the caregiver, i.e. the cause is poor compatibility between the elderly person and the caregiver. One measure against the first cause is to change the caregiver for that elderly person to another caregiver.
  (2) The second cause is simple impairment of vision/hearing, which includes cases where colors cannot be distinguished due to impaired vision, and cases where sounds cannot be heard due to impaired hearing. Measures against the second cause may include compensating for vision impairment by using eyeglasses or using a hearing aid to help hearing, or to carry out communication by finger signs as individual transmission of information.
  (3) The third cause is mental illness such as dementia, which includes cases where the elderly person can see objects and hear sounds, but cannot cognitively understand their meaning. Measures against this third cause may include involving treatment by a specialist.

When ordinary vision/hearing evaluation is conducted for the second cause, for example, the first and third causes may also be contributing factors, and therefore it may not be possible to accurately identify the cause of obstructed communication. In order to accurately distinguish the first to third causes, the subject may be periodically provided with image stimuli and sound stimuli in the three categories, as shown in FIG. 25, estimating the cause by whether emotional expression or positive/negative emotions vary in synchronization with those periods.

In order to judge whether or not the first cause (compatibility) is a cause of obstructed communication, the elderly person may be shown images of a specific caregiver as image stimuli, or the elderly person may be presented with the audio of a specific caregiver as sound stimuli. The "specific caregiver" is the caregiver in charge of taking care of the elderly person who has a problem with communication, for example.

In order to judge whether or not the second cause (vision/hearing) is a cause of obstructed communication, the elderly person may be shown images of colors alone as image stimuli, or the elderly person may be presented with beat sounds at a specific frequency as sound stimuli.

In order to judge whether or not the third cause (mental illness) is a cause of obstructed communication, the elderly person may be shown illusion picture images or non-color stimulus fear-inducing images as image stimuli, or the elderly person may be presented with meaningful words as sound stimuli.

Figure 26:
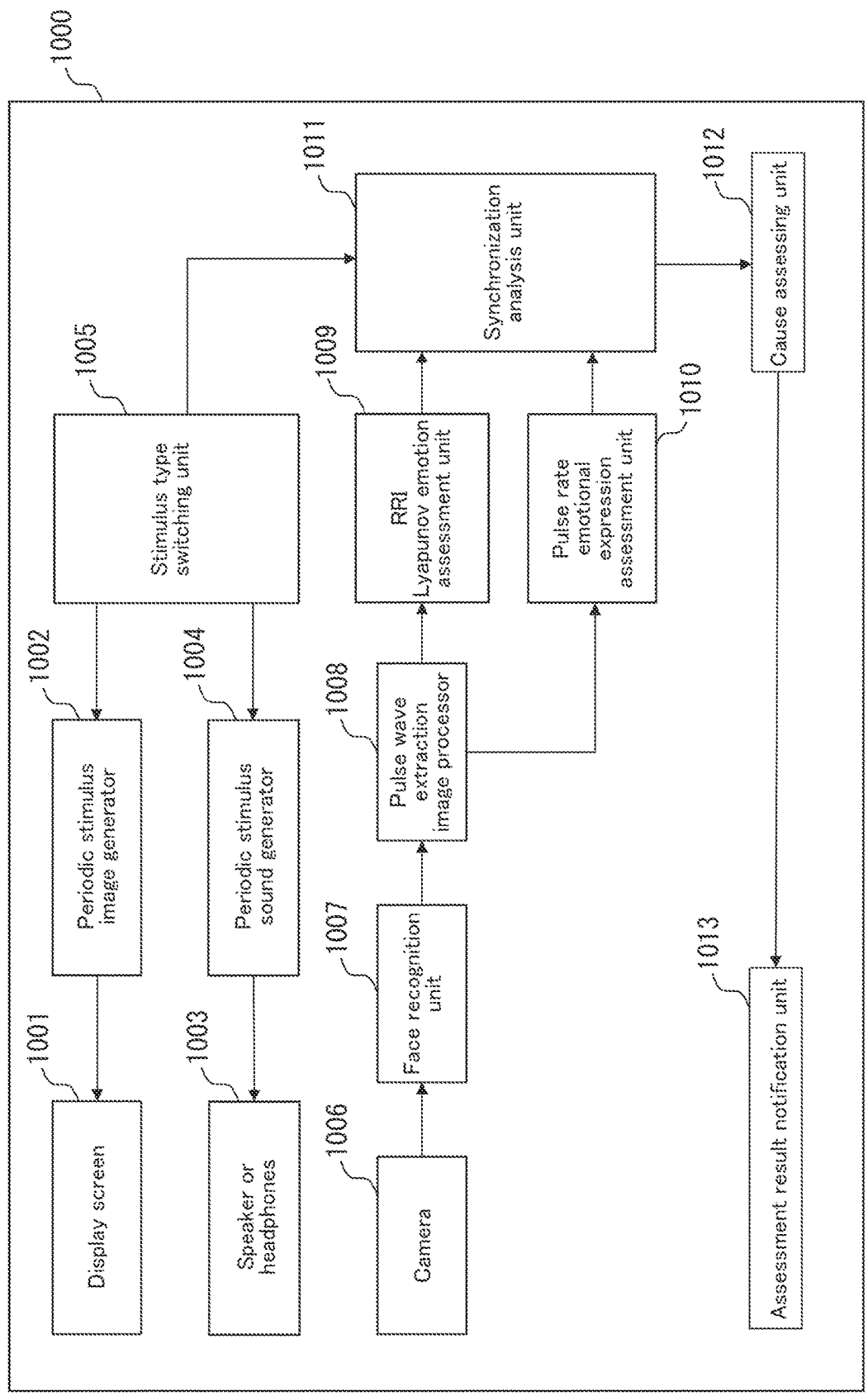
FIG. 26 is a block diagram for a subject condition assessing device, as the communication obstacle factor assessing device of Example 6.

FIG. 26 is a block diagram for a subject condition assessing device 1000, as a communication obstacle factor assessing device. The communication obstacle factor assessing device and subject condition assessing device are examples of emotion assessment apparatus. The subject condition assessing device 1000, as a communication obstacle factor assessing device, has a display screen 1001, a periodic stimulus image generator 1002, a speaker or headphones 1003, a periodic stimulus sound generator 1004, a stimulus type switching unit 1005, a camera 1006, a face recognition unit 1007, a pulse wave extraction image processor 1008, an RRI Lyapunov emotion assessment unit 1009, a pulse rate emotional expression assessment unit 1010, a synchronization analysis unit 1011, a cause assessing unit 1012 and an assessment result notification unit 1013.

The periodic stimulus image generator 1002 and periodic stimulus sound generator 1004 are examples of stimulus generators, which repeatedly generate stimuli for the visual and auditory senses of the subject which are stimuli of the same type, during multiple previously established periods before and after pause periods. The stimuli are of 3 types: a first stimulus, second stimulus and third stimulus as described below, and for example, the first stimulus is repeatedly generated as a stimulus of the same type. Each of the repeatedly generated stimuli may be different so long as they are each still classified as a first stimulus.

The display screen 1001 displays images generated by the periodic stimulus image generator 1002, which are to serve as image stimuli for the elderly participant. The display screen 1001 used may be a liquid crystal display device, an organic EL display device or a projector.

The speaker or headphones 1003 output audio generated by the periodic stimulus sound generator 1004, as sound stimuli for the elderly person.

The stimulus type switching unit 1005 switches the stimulation given to the elderly participant to and from either image stimuli or sound stimuli.

The camera 1006 takes images of the face of the elderly participant.

The face recognition unit 1007 recognizes images of the face from the images taken by the camera 1006.

The pulse wave extraction image processor 1008 is an example of a detecting unit, and it detects heartbeat information including the heart rate of the elderly participant.

The RRI Lyapunov emotion assessment unit 1009 is an example of a counting unit, and it counts the number of heart rate variations for transition from a state below the average heart rate to a state above the average heart rate, where heart rate increase is above a predetermined value during each predetermined time period.

The pulse rate emotional expression assessment unit 1010 is an example of an emotional expression assessment unit, and it assesses the presence of emotional expression by the subject corresponding to stimuli during each predetermined time period, based on the number of heart rate variations.

The synchronization analysis unit 1011 analyzes whether or not the multiple periods are synchronized with the timing of the presence of emotional expression as assessed by the emotional expression assessment unit.

The cause assessing unit 1012 is an example of an obstacle factor assessing unit, and it makes assessment regarding factors causing obstacles to communication for the subject with other persons, based on the analysis results of the synchronization analysis unit 1011.

The assessment result notification unit 1013 outputs the assessment results for the communication obstacle factors as assessed by the cause assessing unit 1012.

Stimuli generated by the periodic stimulus image generator 1002 and periodic stimulus sound generator 1004, as stimulus generators, are first stimuli whose generation can be recognized in a sensory manner either visually or audibly, and the cause factor assessing unit 1012 as the obstacle factor assessing unit assesses the presence of visual or auditory abnormalities. The first stimuli may be sensory stimuli whose generation is recognized upon visual or auditory stimulation. The "sensory stimuli" include stimuli whose generation can be recognized in a sensory manner either visually or audibly. Video is another example of a stimulus including images and audio.

Figure 27:
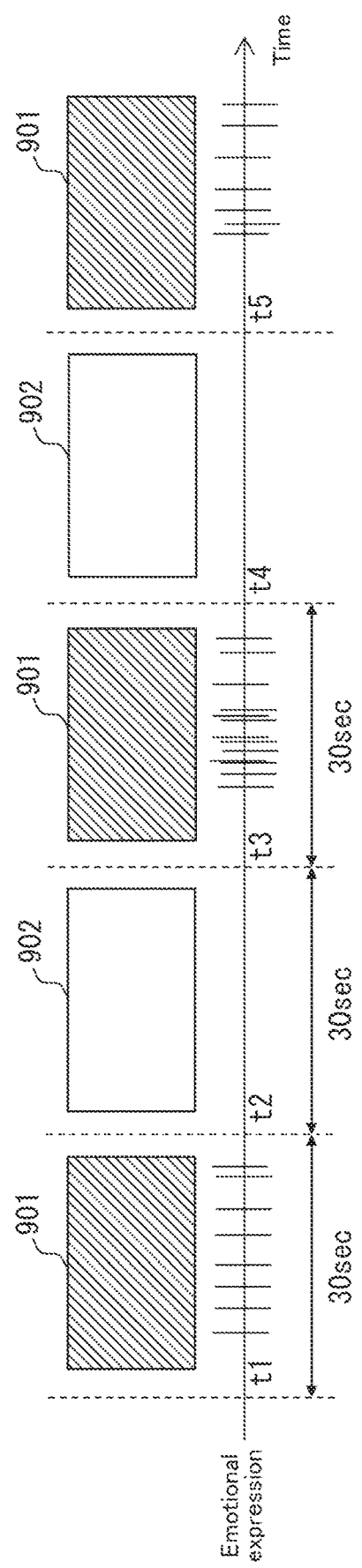
FIG. 27 is an example of time-dependent change in the emotional expression of an elderly subject with periodic exposure to color stimulus as a visual autonomic nerve response color (red, for example), as a first stimulus that can be recognized visually when generated.

A case where the first stimulus is a stimulus that can be recognized visually when generated will now be explained. FIG. 27 shows an example of time-dependent change in the emotional expression of an elderly subject with periodic exposure to color stimulus as a visual autonomic nerve response color (red, for example), as a first stimulus that can be recognized visually when generated. First, the display screen 1001 is situated to allow images to be visible to the elderly subject, and an image 901 that is red, for example, is displayed on the display screen 1001 for a predetermined period from times t1 to t2 (such as 30 sec). A white image 902 without color stimulus is then displayed on the display screen 1001 for a predetermined period (such as 30 sec) from times t2 to t3. From time t3 onward, images containing color stimuli and images without color stimuli (non-stimulating images) are alternately displayed on the display screen 1001. Switching between color stimuli and non-stimuli is carried out by the periodic stimulus image generator 1002.

Facial images of the elderly subject who has been shown color stimuli and non-stimuli are taken using the camera 1006.

The pulse wave extraction image processor 1008 is an example of a detecting unit, and it detects heartbeat information including the heart rate of the elderly person from the images of the elderly subject taken by the camera 1006.

The RRI Lyapunov emotion assessment unit 1009 is an example of an emotion assessment unit, and it assesses whether the emotion of the elderly subject is a negative emotion or a positive emotion, based on heartbeat information.

The pulse wave extraction image processor 1008 also functions as the counting unit, counting the number of heart rate variations for transition from a state below the average heart rate to a state above the average heart rate, where heart rate increase is above a predetermined value during a predetermined time period.

The pulse rate emotional expression assessment unit 1010, as an emotional expression assessment unit, assesses the presence or absence of the mental state of the participant, such as emotional expression, based on the number of heart rate variations.

The synchronization analysis unit 1011 analyzes whether or not the multiple periods of color stimuli and non-stimuli are synchronized with the timing of the presence of emotional expression as assessed by the emotional expression assessment unit.

The cause assessing unit 1012, as an obstacle factor assessing unit, assesses the presence of visual abnormalities based on whether or not the timing of color stimuli is in synchronization with the timing of emotional expression. In the example shown in FIG. 27, for example, emotional expression by the elderly person has been detected when an image 901 containing a color stimulus was displayed from times t1 to t2, while no emotional expression by the elderly person was detected when a white image 902 containing no color stimulus was displayed from times t2 to t3. That is, emotional expression was detected at a timing matching the display of the image 901 containing the color stimulus. In this case, the elderly subject may be judged to have recognized the color and may be assessed to have no visual abnormality.

Figure 28:
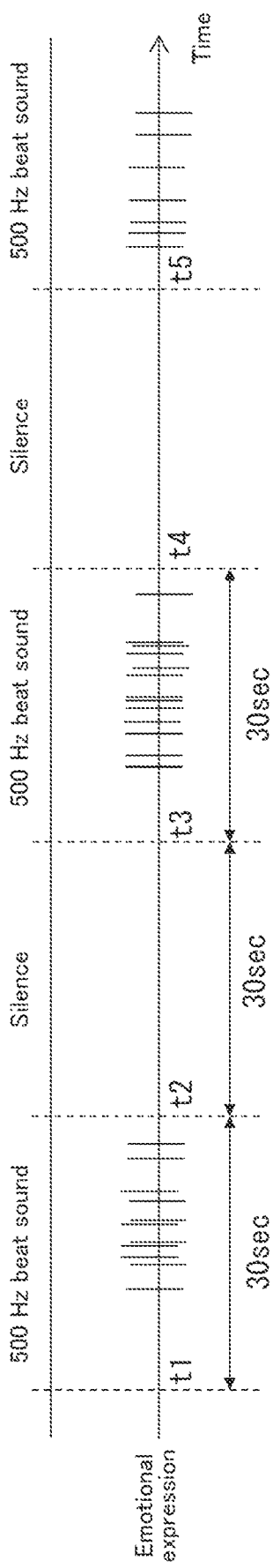
FIG. 28 is an example of time-dependent change in the emotion of an elderly subject with periodic exposure to a beat sound of a predetermined frequency, as a first stimulus that can be recognized audibly when generated.

A case where the first stimulus is a stimulus that can be recognized audibly when generated will now be explained. FIG. 28 is an example of time-dependent change in the emotional expression of an elderly subject with periodic exposure to a beat sound of a predetermined frequency (such as 500 Hz), as a first stimulus that can be recognized audibly when generated. First, a 500 Hz beat sound is outputted from a speaker or headphones 1003 for a predetermined period from times t1 to t2 (such as 30 sec). Next, sound is not outputted from the speaker or headphones 1003 (silence) for a predetermined period from times t2 to t3 (such as 30 sec). From time t3 onward, output of the 500 Hz beat sound and silence are alternately repeated. Switching between the 500 Hz beat sound and silence is carried out by the periodic stimulus sound generator 1004.

Facial images of the elderly subject who has been exposed to the 500 Hz beat sound and silence are taken using the camera 1006.

The pulse wave extraction image processor 1008 is an example of a detecting unit, and it detects heartbeat information including the heart rate of the elderly person from the images of the elderly subject taken by the camera 1006.

The RRI Lyapunov emotion assessment unit 1009 is an example of an emotion assessment unit, and it assesses whether the emotion of the elderly subject is a negative emotion or a positive emotion, based on heartbeat information.

The pulse wave extraction image processor 1008 also functions as the counting unit, counting the number of heart rate variations for transition from a state below the average heart rate to a state above the average heart rate, where heart rate increase is above a predetermined value during a predetermined time period.

The pulse rate emotional expression assessment unit 1010, as an emotional expression assessment unit, assesses the presence or absence of the mental state of the participant, such as emotional expression, based on the number of heart rate variations.

The synchronization analysis unit 1011 analyzes whether or not the multiple periods of sound stimuli and non-stimuli are synchronized with the timing of the presence of emotional expression as assessed by the emotional expression assessment unit.

The cause assessing unit 1012, as an obstacle factor assessing unit, assesses the presence of auditory abnormalities based on whether or not the timing of 500 Hz beat sound output is in synchronization with the timing of emotional expression. In the example shown in FIG. 28, for example, emotional expression by the elderly person has been detected when a 500 Hz beat sound was outputted from times t1 to t2, while no emotional expression by the elderly person was detected when no sound was generated from times t2 to t3. In other words, emotional expression was detected at a timing matching output of the 500 Hz beat sound. In this case, the elderly subject may be judged to have recognized the sound and may be assessed to have no auditory abnormality.

In the subject condition assessing device 1000 described above, stimulation may be with a first stimulus whose generation can be recognized simply by visual or auditory sensation. That is, the first stimulus is a stimulus whose generation can be recognized merely by visual sensation or only by auditory sensation (in a sensory manner), without requiring recognition of the information contained in the stimulus. The first stimulus may also be a stimulus that also has some information in the stimulus, whereby sensory recognition of the presence of the stimulus produces an emotional expression, and recognition of the information in the stimulus produces or sometimes produces an emotional expression.

The stimulus may also be a second stimulus that contains certain information the content of which can be understood either visually or audibly, and the obstacle factor assessing unit may assess the presence of any mental abnormality in the subject. The second stimulus may also be a cognitive stimulus accompanying cognition of the given information. For example, the second stimulus that is used may be an image such as an illusion picture where the color is non-stimulating, but a normally impossible form is hidden in the illusion picture and a reaction tends to result when the meaning of the illusion picture is understood. Alternatively, the second stimulus used may be audio wherein the sound itself is non-stimulating but a reaction tends to result when the meaning of the words are understood.

Figure 29:
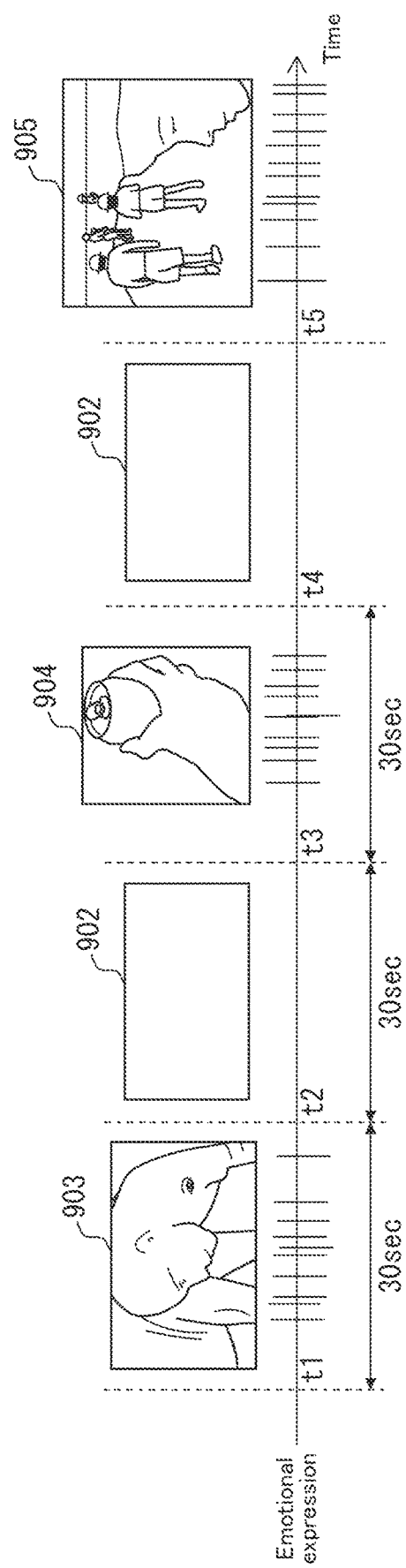
FIG. 29 is an example of time-dependent change in the emotional expression of an elderly subject, with periodic exposure to an illusion picture evocative of surprise or laughter when its meaning is understood, as a second stimulus including predetermined information with content that can be understood visually.

The use of an image containing certain information that can be understood as a second stimulus will be explained first. FIG. 29 shows an example of time-dependent change in the emotional expression of an elderly subject, with periodic exposure to an illusion picture evocative of surprise or laughter when its meaning is understood, as a second stimulus including predetermined information with content that can be understood visually. First, an image 903 in which an elephant ear is in the form of a human profile is displayed on the display screen 1001 for a predetermined period from times t1 to t2 (such as 30 sec). A white image 902 without an illusion picture is then displayed on the display screen 1001 for a predetermined period (such as sec) from times t2 to t3. Next, an image 904 in which the hand holding a can that should be the right hand is depicted as a left hand, is displayed on the display screen 1001 for a predetermined period from times t3 to t4 (such as 30 sec). A white image 902 without an illusion picture is then displayed on the display screen 1001 for a predetermined period (such as sec) from times t4 to t5. Next, an image 905 in which the shaded contour of the ground is in the form of a human profile is displayed on the display screen 1001 for a predetermined period from time t5 until a certain time (such as 30 sec). Switching between images with illusion pictures and images without illusion pictures is carried out by the periodic stimulus image generator 1002.

The facial image of the elderly subject viewing the images with illusion pictures and images without illusion pictures is taken with the camera 1006.

The pulse wave extraction image processor 1008 is an example of a detecting unit, and it detects heartbeat information including the heart rate of the elderly person from the images of the elderly subject taken by the camera 1006.

The RRI Lyapunov emotion assessment unit 1009 is an example of an emotion assessment unit, and it assesses whether the emotion of the elderly subject is a negative emotion or a positive emotion, based on heartbeat information.

The pulse wave extraction image processor 1008 also functions as the counting unit, counting the number of heart rate variations for transition from a state below the average heart rate to a state above the average heart rate, where heart rate increase is above a predetermined value during a predetermined time period.

The pulse rate emotional expression assessment unit 1010, as an emotional expression assessment unit, assesses the presence or absence of the mental state of the participant, such as emotional expression, based on the number of heart rate variations.

The synchronization analysis unit 1011 analyzes whether or not the multiple periods of displaying images with illusion pictures and images without illusion pictures are synchronized with the timing of the presence of emotional expression as assessed by the emotional expression assessment unit.

The cause assessing unit 1012, as an obstacle factor assessing unit, assesses the presence of mental abnormalities based on whether or not the timing of displaying illusion picture-containing images is in synchronization with the timing of emotional expression. In the example shown in FIG. 29, for example, emotional expression was detected when images 903, 904 and 905 with illusion pictures were displayed, while no emotional expression was detected when an image 902 without an illusion picture was displayed. That is, emotional expression was detected at a timing matching display of the images 903, 904, 905 with illusion pictures. In this case, the elderly subject may be judged to have recognized the meanings of the illusion pictures and may be assessed to have no mental abnormality.

Since it is sometimes difficult to understand the meaning of an image such as an illusion picture, when multiple illusion picture images wave been displayed, it may be assessed that there is no mental abnormality even if emotional expression was not detected for some of the illusion pictures if emotional expression was detected for the other illusion pictures, i.e. without requiring emotional expression to be detected for all of the illusion picture images. Multiple types of images with different contents may also be selected for images containing information whose content can be understood, for use as the second stimulus.

Figure 30:
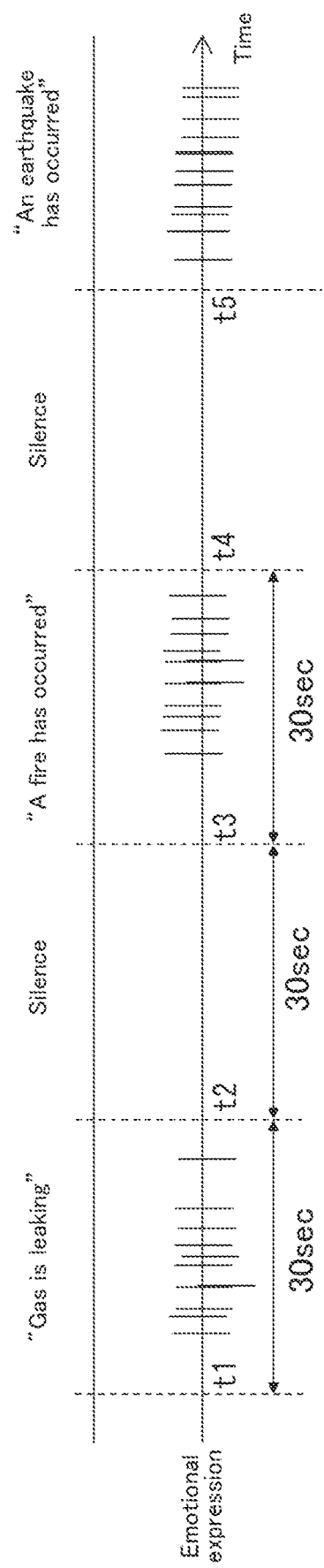
FIG. 30 is an example of time-dependent change in the emotional expression of an elderly subject, with periodic exposure to audio evocative of surprise or laughter when its meaning is understood, as a second stimulus including predetermined information with content that can be understood audibly.

The use of audio containing certain information that can be understood as a second stimulus will now be explained. FIG. 30 shows an example of time-dependent change in the emotional expression of an elderly subject, with periodic exposure to audio evocative of surprise or laughter when its meaning is understood, as a second stimulus including predetermined information with content that can be understood audibly. First, a voice saying "gas is leaking" is outputted from a speaker or headphones 1003 either once or several times for a predetermined period from times t1 to t2 (such as 30 sec). Next, sound is not outputted (silence) for a predetermined period from times t2 to t3 (such as 30 sec). A voice saying "a fire has occurred" is then outputted from the speaker or headphones 1003 either once or several times for a predetermined period from times t3 to t4 (such as 30 sec). Next, sound is not outputted (silence) for a predetermined period from times t4 to t5 (such as 30 sec). A voice saying "an earthquake has occurred" is then outputted from the speaker or headphones 1003 either once or several times for a predetermined period from time t5 until a certain time (such as 30 sec). Switching between voice output and silence is carried out by the periodic stimulus image generator 1002.

Facial images of the elderly subject with output of voices with specific meaning and without output of voices are taken using the camera 1006.

The pulse wave extraction image processor 1008 is an example of a detecting unit, and it detects heartbeat information including the heart rate of the elderly person from the images of the elderly subject taken by the camera 1006.

The RRI Lyapunov emotion assessment unit 1009 is an example of an emotion assessment unit, and it assesses whether the emotion of the elderly subject is a negative emotion or a positive emotion, based on heartbeat information.

The pulse wave extraction image processor 1008 also functions as the counting unit, counting the number of heart rate variations for transition from a state below the average heart rate to a state above the average heart rate, where heart rate increase is above a predetermined value during a predetermined time period.

The pulse rate emotional expression assessment unit 1010, as an emotional expression assessment unit, assesses the presence or absence of the mental state of the participant, such as emotional expression, based on the number of heart rate variations.

The synchronization analysis unit 1011 analyzes whether or not the multiple periods of sound stimuli and non-stimuli are synchronized with the timing of the presence of emotional expression as assessed by the emotional expression assessment unit.

The cause assessing unit 1012, as an obstacle factor assessing unit, assesses the presence of mental abnormalities based on whether or not the timing of voice output is in synchronization with the timing of emotional expression. In the example shown in FIG. 30, for example, emotional expression was detected when voice audio with a specific meaning has been outputted, while emotional expression was not detected when voice audio was not outputted. In other words, emotional expression was detected at a timing matching output of voice audio with a specific meaning. In this case, the elderly subject may be judged to have recognized the meanings of the words and may be assessed to have no mental abnormality.

The pulse wave extraction image processor 1008 also functions as a calculating unit to calculate the complexity of changes in fluctuation in heartbeat interval from heartbeat information. The pulse wave extraction image processor 1008 may calculate the complexity of changes in fluctuation in heartbeat interval from the heartbeat information, using the maximal Lyapunov exponent as the indicator, for example. The RRI Lyapunov emotion assessment unit 1009 also functions as an emotion assessment unit to assess whether the emotion of the subject is a negative emotion or a positive emotion, based on the complexity. For example, the RRI Lyapunov emotion assessment unit 1009 may assess whether the emotion of the subject is a negative emotion or a positive emotion, based on the maximal Lyapunov exponent calculated by the pulse wave extraction image processor 1008, for example. The stimulus given to the elderly subject by the stimulus generator may be a third stimulus including at least an image or voice of a specific person. The cause assessing unit 1012, as an obstacle factor assessing unit, may assess the compatibility between the subject and a specific person.

Figure 31:
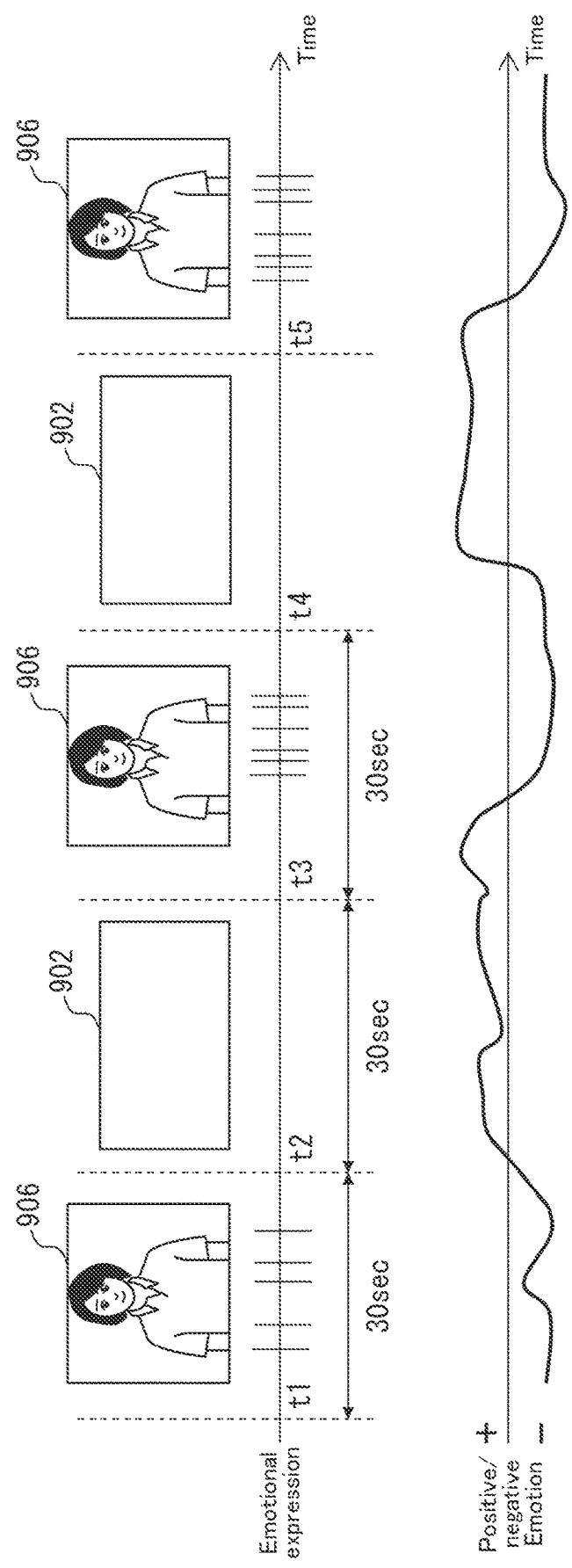
FIG. 31 is an example of time-dependent change in emotional expression and positive and negative emotion of an elderly subject, with periodic exposure of images of a caregiver to an elderly participant, as a third stimulus including images of a specific person.

An example in which the third stimulus is a stimulus including images of a specific person will be explained first. FIG. 31 shows an example of time-dependent change in emotional expression and positive and negative emotion of an elderly subject, with periodic exposure of images of a caregiver to an elderly subject, as a third stimulus including images of a specific person. First, an image of a caregiver 906 is displayed on the display screen 1001 for a predetermined period (such as 30 sec) from times t1 to t2. A white image 902 without an image of the caregiver is then displayed on the display screen 1001 for a predetermined period (such as sec) from times t2 to t3. From time t3 onward, the images of the caregiver 906 and white images 902 without images of the caregiver are repeatedly displayed on the display screen 1001 in an alternating manner. Switching between images of the caregiver 906 and white images 902 without images of the caregiver is carried out by the periodic stimulus image generator 1002.

Facial images of the elderly subject viewing the images of the caregiver 906 and white images 902 without images of the caregiver are taken with the camera 1006.

The pulse wave extraction image processor 1008 is an example of a detecting unit, and it detects heartbeat information including the heart rate of the elderly person from the images of the elderly subject taken by the camera 1006.

The RRI Lyapunov emotion assessment unit 1009 is an example of an emotion assessment unit, and it assesses whether the emotion of the elderly subject is a negative emotion or a positive emotion, based on heartbeat information. The RRI Lyapunov emotion assessment unit 1009 may assess whether the emotion of the elderly subject is a negative emotion or a positive emotion, based on the complexity of changes in fluctuation in heartbeat interval calculated from the heartbeat information by the pulse wave extraction image processor 1008.

The pulse wave extraction image processor 1008 also functions as the counting unit, counting the number of heart rate variations for transition from a state below the average heart rate to a state above the average heart rate, where heart rate increase is above a predetermined value during a predetermined time period.

The pulse rate emotional expression assessment unit 1010, as an emotional expression assessment unit, assesses the mental state of the elderly subject, such as the presence of emotional expression, corresponding to stimuli during each predetermined time period, based on the number of heart rate variations.

The synchronization analysis unit 1011 analyzes whether or not the multiple periods of displaying images of the caregiver 906 and white images 902 without images of the caregiver are synchronized with the timing of the presence of emotional expression as assessed by the emotional expression assessment unit, and the timing at which the elderly person expresses positive/negative emotion.

The cause assessing unit 1012, as an obstacle factor assessing unit, assesses the compatibility between the elderly subject and the caregiver, based on whether or not the timing of display of images of the caregiver 906 is synchronized with the timing of emotional expression, and based on whether the emotion is positive or negative.

It is possible that emotional expression will be seen when the elderly subject has been shown an image of the caregiver, regardless of whether compatibility between the elderly person and the caregiver is good or poor. Therefore, when an elderly person shows emotional expression after having seen an image of a caregiver, it may be assessed that the elderly person is experiencing some emotion with regard to the caregiver. However, merely the presence or absence of emotional expression does not allow assessment of whether compatibility between the elderly person and the caregiver is good or poor.

The cause assessing unit 1012 therefore assesses whether compatibility between the elderly person and the caregiver is good or poor by using the assessment results (positive/negative emotion) from the RRI Lyapunov emotion assessment unit 1009.

For example, when emotional expression is shown after the elderly person has viewed an image of a caregiver and positive emotion has been shown by the elderly person at the same timing, then the cause assessing unit 1012 can assess that compatibility between the elderly person and caregiver is good, i.e. that the elderly person personally likes the caregiver.

On the other hand, when emotional expression is shown after the elderly person has viewed an image of a caregiver and negative emotion has been shown by the elderly person at the same timing, then the cause assessing unit 1012 can assess that compatibility between the elderly person and caregiver is poor, i.e. that the elderly person personally dislikes the caregiver.

The cause assessing unit 1012 thus has a function as an emotional expression assessment unit, and the assessment results (positive/negative emotion) from the RRI Lyapunov emotion assessment unit 1009 as the emotion assessment unit can be used for assessment of mental state (level of compatibility).

In this case, the pulse rate emotional expression assessment unit 1010 and cause assessing unit 1012 perform functions as emotional expression assessment units.

The level of compatibility is triggered by a causative mental state of the elderly person as the subject (unconscious or conscious mental state of the subject toward the caregiver, such as liking or disliking the caregiver). The emotional expression assessment unit therefore assesses the level of compatibility as the mental state, as described above.

In the example shown in FIG. 31, for example, the emotional expression is detected at a timing at which images of the caregiver 906 are shown, and negative emotion is detected. In this case, it can at least be assessed that the compatibility between the elderly person and the caregiver is poor, since the elderly subject has poor compatibility with the caregiver.

Figure 32:
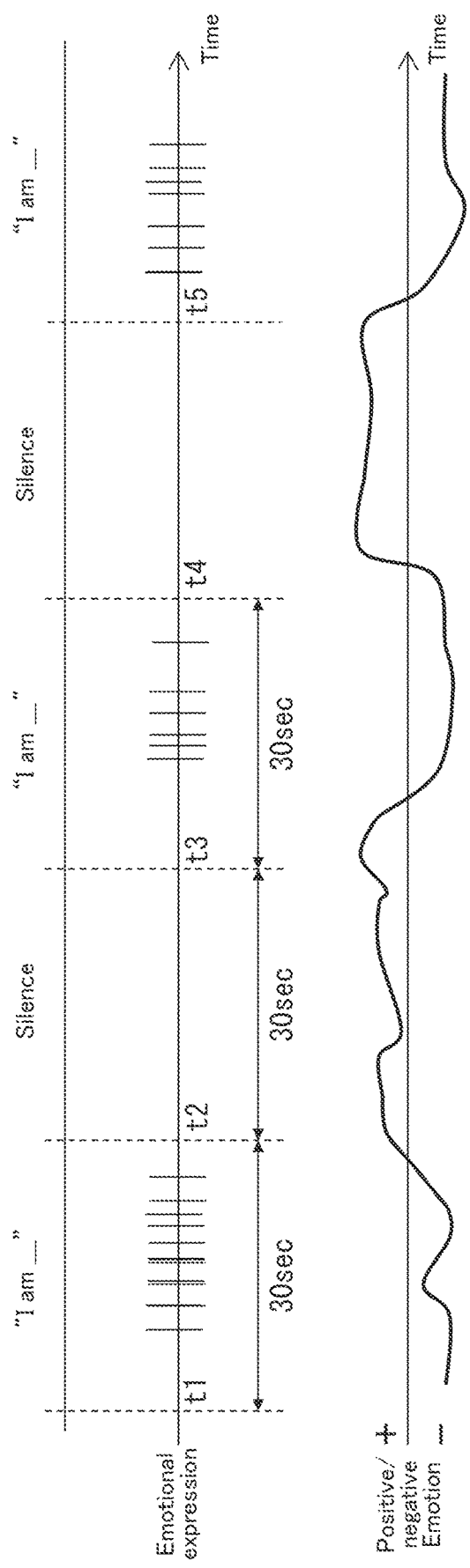
FIG. 32 is an example of time-dependent change in emotional expression and positive and negative emotion of an elderly subject, with periodic exposure of the voice of a caregiver to an elderly subject, as a third stimulus including the voice of a specific person.

An example in which the third stimulus is a stimulus including the voice of a specific person will be explained next. FIG. 32 shows an example of time-dependent change in emotional expression and positive and negative emotion of an elderly subject, with periodic exposure of the voice of a caregiver to an elderly subject, as a third stimulus including the voice of a specific person. First, a voice saying "I am _____", inserting the name of the caregiver, is outputted from a speaker or headphones 1003 either once or several times for a predetermined period from times t1 to t2 (such as 30 sec). Next, output of the voice is stopped (silence) for a predetermined period from times t2 to t3 (such as 30 sec). From time t3 onward, output of the voice of the caregiver and a state of silence are repeated in an alternating manner. Switching between output of the voice of the caregiver and a state of silence is carried out by the periodic stimulus sound generator 1004.

Facial images of the elderly subject with periodic exposure to the voice of the caregiver saying their own name as, "I am _____" are taken using the camera 1006.

The pulse wave extraction image processor 1008 is an example of a detecting unit, and it detects heartbeat information including the heart rate of the elderly person from the images of the elderly subject taken by the camera 1006.

The RRI Lyapunov emotion assessment unit 1009 is an example of an emotion assessment unit, and it assesses whether the emotion of the elderly subject is a negative emotion or a positive emotion, based on heartbeat information. The RRI Lyapunov emotion assessment unit 1009 may assess whether the emotion of the elderly subject is a negative emotion or a positive emotion, based on the complexity of changes in fluctuation in heartbeat interval calculated from the heartbeat information by the pulse wave extraction image processor 1008.

The pulse wave extraction image processor 1008 also functions as the counting unit, counting the number of heart rate variations for transition from a state below the average heart rate to a state above the average heart rate, where heart rate increase is above a predetermined value during a predetermined time period.

The pulse rate emotional expression assessment unit 1010, as an emotional expression assessment unit, assesses the mental state of the elderly subject, such as the presence of emotional expression, corresponding to stimuli during each predetermined time period, based on the number of heart rate variations.

The synchronization analysis unit 1011 analyzes whether or not the multiple periods of sound stimuli and non-stimuli are synchronized with the timing of the presence of emotional expression as assessed by the emotional expression assessment unit and the timing at which the elderly person exhibits positive/negative emotion.

The cause assessing unit 1012, as an obstacle factor assessing unit, assesses the level of compatibility between the elderly subject and the caregiver, based on whether or not the timing of output of the voice of the caregiver saying their own name as "I am _____" is synchronized with the timing of emotional expression, and based on whether the emotion is positive or negative.

It is possible that emotional expression will be seen when the elderly subject has heard the voice of the caregiver, regardless of whether compatibility between the elderly person and the caregiver is good or poor. When an elderly person shows emotional expression after having heard the voice of the caregiver, therefore, it may be assessed that the elderly person is experiencing some emotion with regard to the caregiver. However, merely the presence or absence of emotional expression does not allow assessment of whether compatibility between the elderly person and the caregiver is good or poor.

The cause assessing unit 1012 therefore assesses whether compatibility between the elderly person and the caregiver is good or poor by using the assessment results (positive/negative emotion) from the RRI Lyapunov emotion assessment unit 1009.

For example, when emotional expression is shown after the elderly person has heard the voice of the caregiver and positive emotion has been shown by the elderly person at the same timing, then the cause assessing unit 1012 can assess that compatibility between the elderly person and caregiver is good, i.e. that the elderly person personally likes the caregiver.

On the other hand, when emotional expression is shown after the elderly person has heard the voice of the caregiver and negative emotion has been shown by the elderly person at the same timing, then the cause assessing unit 1012 can assess that compatibility between the elderly person and caregiver is poor, i.e. that the elderly person personally dislikes the caregiver.

The cause assessing unit 1012 thus has a function as an emotional expression assessment unit, and the assessment results (positive/negative emotion) from the RRI Lyapunov emotion assessment unit 1009 as the emotion assessment unit can be used for assessment of mental state (level of compatibility).

In this case, the pulse rate emotional expression assessment unit 1010 and cause assessing unit 1012 perform functions as emotional expression assessment units.

The level of compatibility is triggered by a causative mental state of the elderly person as the subject (unconscious or conscious mental state of the subject toward the caregiver, such as liking or disliking the caregiver). The emotional expression assessment unit therefore assesses the level of compatibility as the mental state, as described above.

In the example shown in FIG. 32, for example, the emotional expression is detected at a timing at which the voice of the caregiver saying their own name as "I am _____" is outputted, and negative emotion is detected. In this case, it can be assessed that compatibility between the elderly subject and the caregiver is poor.

The periodic stimulus image generator 1002 and periodic stimulus sound generator 1004, as stimulus generators, repeat an operation of generating any of the first to third stimuli during a predetermined time period, and subsequently generating a different stimulus from among the first to third stimuli, at least until three of the first to third stimuli are generated. The pulse rate emotional expression assessment unit 1010 assesses that the subject has emotional expression when the number of heart rate variations is two or more during each stimulus generating period and each stimulus pause period (all corresponding to the predetermined time period). This is because emotional expression can be exhibited once even without generation of a stimulus, simply in response to switching between screens in the stimulus generating period and stimulus pause period. In other words, such emotional expression is emotional expression that is not due to the first to third stimuli, and should therefore be excluded from assessment of emotional expression due to the first to third stimuli. The first to third stimuli generated by the periodic stimulus image generator 1002 and periodic stimulus sound generator 1004 are stimuli that produce at least two or more emotional expressions. This is because the purpose is not to test reflective reaction such as surprise, as assessed by a single heart rate variability count by each stimulus, but rather to test whether or not there has been a change in mental state as assessed by a heart rate variability count of two or more.

By assessing the presence or absence of emotional expression in the elderly person after the first and second stimuli have been given to the elderly person, and assessing the presence or absence of positive/negative emotion and emotional expression by the elderly person after the third stimulus has been given to the elderly person, it is possible to assess the cause of obstructed communication with the elderly person. In other words, the cause assessing unit 1012, as an obstacle factor assessing unit, can make multiple assessments regarding the presence or absence of visual or auditory abnormalities and the presence or absence of mental abnormality in the subject, and the level of compatibility with specific persons, and for assessment of the obstacle factors, can also assess which of the multiple assessments is related to the obstacle factors for a subject. FIG. 33 shows an example of assessment of the cause of obstructed communication with an elderly person.

An example in which the elderly person is assessed to be in a normal state will be explained first. When a reaction is received by an elderly person in response to a first stimulus for vision/hearing assessment, the elderly person can be assessed to have no visual or auditory abnormality. When a reaction is received from the elderly person in response to a second stimulus for mental illness assessment, the elderly person can be judged to be in a state without mental abnormality. When there is no reaction or a positive reaction (positive emotion) from the elderly person in response to a third stimulus for compatibility assessment, it can be assessed that the compatibility between the elderly person and the caregiver is not poor.

An example in which an elderly person is assessed to be in a state with mental abnormality will now be explained. When a reaction is exhibited by an elderly person in response to a first stimulus for vision/hearing assessment, the elderly person can be assessed to have no visual or auditory abnormality. When no reaction has been received from the elderly person in response to the second stimulus for mental illness assessment, this means that the meaning of the images or audio in the second stimulus could not be understood, and it can be judged that the elderly person is in a state with mental abnormality. When there is no reaction or a positive reaction (positive emotion) from the elderly person in response to a third stimulus for compatibility assessment, it can be assessed that the compatibility between the elderly person and the caregiver is not poor.

An example in which an elderly person is assessed to be in a state with auditory abnormality will now be explained. When a reaction is exhibited by an elderly person in response to a first stimulus for vision assessment, the elderly person can be assessed to have no visual abnormality. When no reaction is exhibited by an elderly person in response to the first stimulus for hearing assessment, the elderly person can be assessed to be in a state with auditory abnormality. When the elderly person has an auditory abnormality, the presence or absence of mental abnormality cannot be assessed from the reaction obtained when the elderly person has been given a second stimulus containing audio for assessment of mental illness. Consequently, the designation "no/yes" is used as shown in the table of FIG. 33, in order to assess auditory abnormality regardless of the presence or absence of acoustic response to the second stimulus that contains audio. When there is no reaction or a positive reaction (positive emotion) from the elderly person in response to a third stimulus for compatibility assessment, it can be assessed that the compatibility between the elderly person and the caregiver is not poor. The example shown in FIG. 33 shows a case where compatibility between the elderly person and the caregiver is good, but it may be the case that the elderly person has an auditory abnormality and compatibility with the caregiver is not good.

An example in which an elderly person is assessed to be in a state with visual abnormality will now be explained. When a reaction is exhibited by an elderly person in response to a first stimulus for hearing assessment, the elderly person can be assessed to have no auditory abnormality. When no reaction is exhibited by the elderly person in response to a first stimulus for vision assessment, the elderly person can be assessed to be in a state with visual abnormality. When the elderly person has a visual abnormality, the presence or absence of mental abnormality cannot be assessed from the reaction obtained when the elderly person has been given a second stimulus containing an image for assessment of mental illness. Consequently, the designation "no/yes" is used as shown in the table of FIG. 33, in order to assess visual abnormality regardless of the presence or absence of an image response to the second stimulus that contains an image. When there is no reaction or a positive reaction (positive emotion) from the elderly person in response to a third stimulus for compatibility assessment, it can be assessed that compatibility between the elderly person and the caregiver is not poor. The example shown in FIG. 33 shows a case where compatibility between the elderly person and the caregiver is good, but it may be the case that the elderly person has an auditory abnormality and compatibility with the caregiver is not good.

An example of assessing the level of compatibility of an elderly person will now be explained. When a reaction is exhibited by an elderly person in response to a first stimulus for vision/hearing assessment, the elderly person can be assessed to have no visual or auditory abnormality. When a reaction is received from the elderly person in response to a second stimulus for mental illness assessment, the elderly person can be judged to be in a state without mental abnormality. When a reaction has been received from the elderly person in response to a third stimulus for compatibility assessment, and a negative reaction (negative emotion) is exhibited, it can be assessed that compatibility between the elderly person and the caregiver is poor. When a negative reaction has been received by the elderly person who has been given at least one image stimulus and/or sound stimulus as a third stimulus for compatibility assessment, then it may be assessed that compatibility between the elderly person and the caregiver is poor. When a reaction has been received from the elderly person in response to a third stimulus for compatibility assessment, and a positive reaction (positive emotion) is exhibited, unlike the case shown in FIG. 33, it can be assessed that compatibility between the elderly person and the caregiver is good.

A method for evaluating the presence or absence of emotional expression will now be explained. FIG. 34(A) shows an example of true values for reactions exhibited after exposure to periodic stimulation. First, a predetermined period from times t1 to t2 (such as 30 sec) is designated as a stimulus pause period in which stimulation is not given to the subject. It is expected that the subject will not exhibit a reaction during this time, and therefore the true value is "0". Next, a predetermined period from times t2 to t3 (such as 30 sec) is designated as a stimulus generating period in which stimulation is given to the subject. It is expected that the subject will exhibit a reaction during this time, and therefore the true value is "1". From time t3 onward, an true value of "0" for the stimulus pause period and an true value of "1" for the stimulus generating period is periodically repeated, when having periodically repeated a stimulus pause period and stimulus generating period.

FIG. 34(B) shows an example of assessment of emotional expression when a participant has been exposed to a stimulus at the timing represented in FIG. 34(A). For example, if times t1 to t2 represent a stimulus pause period and no emotional expression was detected when stimulus was given to the subject, the emotional expression is "no" and the value is represented as "0". Since the true value at this time is "0" based on FIG. 34(A), the emotional expression during the stimulus pause period matches the true value. If times t2 to t3 represent a stimulus generating period and emotional expression was detected when stimulus was given to the subject, the emotional expression is "yes" and the value is represented as "1". Since the true value at this time is "1" based on FIG. 34(A), the emotional expression during the stimulus generating period matches the true value.

The stimulus pause period and stimulus generating period are periodically repeated from times t3 to t11, and emotional expression was assessed during a total of 10 periods. If emotional expression was not detected during the stimulus generating period from times t6 to t7, the emotional expression is "no" ("0"). However, since the true value during the period is "1", the emotional expression assessment results do not match the true value. Of the total of 10 periods from t1 to t11, the emotional expression assessment results match the true value during the other 9 periods excluding the period from t6 to t7, and therefore the synchronization rate is calculated as 90%. The synchronization analysis unit 1011 makes an assessment based on whether or not the percentage of synchronization with the presence or absence of emotional expression during the stimulus generating period and stimulus pause period, i.e. the synchronization rate, is above a predetermined value. For example, if the predetermined value is 70% and the calculated synchronization rate is 90%, then the predetermined value of 70% is exceeded, and it can therefore be assessed that emotional expression is synchronized with the stimulus.

In the example described above, assessment was made by calculating the synchronization rate for the presence or absence of emotional expression for multiple periods of stimulus and stimulus pause periods, but there is no limitation to this example. That is, if number of stimulus generations and the number of stimulus pauses are fixed, then assessment of whether or not the frequency of synchronization is above a predetermined number, even if the synchronization rate is not calculated, may still be considered to be assessment based on the synchronization rate (percentage of synchronization). For example, when the total of stimulus generating periods and stimulus pause periods is fixed at 10 periods, as shown in FIG. 34(A) and FIG. 34(B), and the number of synchronized times among the stimulus generating periods and stimulus pause periods is above a predetermined number (for example, 7 times), then the synchronization rate may be considered to be above the predetermined value of 70% and an assessment of "synchronized" may be made.

By using the subject condition assessing device 1000, as a communication obstacle factor assessing device, it is possible to carry out examination on the first day that an elderly person is admitted to a nursing home, and to ascertain the type of the admitted elderly person. For assessing compatibility between an elderly person and a caregiver, such assessment cannot be made if the caregiver and the elderly person have not interacted within a predetermined period, and therefore the examination may be made at about 1 month after the elderly person is admitted to the nursing home, for example. By assessing the cause of obstructed communication between an elderly person and a caregiver it is possible to appropriately select a countermeasure to aid communication.

[Supplementary Notes]

Example 6 described above is a specific example of the invention as exemplified in the following supplementary notes.

(Supplementary Note 1)

A subject condition assessing apparatus having:
 a stimulus generation unit that generates a visual or auditory stimulus for a subject every previously established number of predetermined time periods with intervening pause periods,
 a detecting unit that detects heartbeat information including the heart rate of the subject,
 a counting unit that counts the number of heart rate variations within the predetermined time period, the heart rate variations being transitions from a state in which the heart rate is below the average heart rate to a state in which the heart rate is greater than or equal to the average heart rate and being with heart rate increase greater than or equal to a predetermined value,
 an emotional expression assessment unit that assesses the presence or absence of emotional expression by the subject in response to stimuli every predetermined time period, based on the number of heart rate variations,
 a synchronization analysis unit that analyzes whether or not the timing of the multiple periods is synchronized with timing of the presence or absence of emotional expression as assessed by the emotional expression assessment unit, and
 an obstacle factor assessing unit that performs assessment regarding communication obstacle factors between the subject and others, based on the analysis results from the synchronization assessing unit.

Previously known devices for assessing communication obstacle factors include devices that assess the presence or absence of visual, auditory or cognitive abnormalities based on visual and auditory sensing by the subject. Devices of the prior art, however, have made assessment by reactions from the subject such as responses or button pushing, with assessment being impossible when such responsive actions are difficult. Devices that assess communication obstacle factors based on subject electroencephalograms are also known. Such devices are large, however, and require wide spaces for installation. In addition, such devices require advanced analysis means, limiting the types of personnel that can manage them.

It is therefore preferred to determine communication obstacle factors for subjects more easily and with simpler configurations, while reducing the restrictions of installation locations and managing personnel.

Since the subject condition assessing apparatus described by the supplementary notes perform assessment of obstacle factors based on the number of heart rate variation for transition to a state above the average heart rate and "analysis of synchronization with timing of the presence or absence of emotional expression", they have simple configurations and reduce restrictions on installation locations, while also being able to assess communication obstacle factors on subjects by simple testing, thus allowing restrictions on the managing personnel to be reduced as well.

(Supplementary Note 2)

The subject condition assessing apparatus according to supplementary note 1, wherein:
 the stimulus is a first stimulus that can be recognized in a sensory manner visually or audibly when generated, and
 the obstacle factor assessing unit assesses the presence or absence of visual or auditory abnormalities.

In the subject condition assessing apparatus according to supplementary note 2, the stimulus is a first stimulus whose generation can be recognized simply by visual or auditory sensation.

(Supplementary Note 3)

The subject condition assessing apparatus according to supplementary note 1 or 2, wherein:
 the stimulus is a second stimulus with informational content that can be understood, and
 the obstacle factor assessing unit assesses the presence or absence of mental abnormalities of the subject.

(Supplementary Note 4)

The subject condition assessing apparatus according to any one of supplementary notes 1 to 3, which further has:
 a calculating unit that calculates the complexity of changes in fluctuation in heartbeat interval from heartbeat information, and
 an emotion assessment unit that assesses whether emotion of the subject is negative emotion or positive emotion based on the complexity,
 wherein the stimulus is a third stimulus including at least an image or voice of a specific person, and
 the obstacle factor assessing unit assesses compatibility between the subject and the specific person.

(Supplementary Note 5)

The subject condition assessing apparatus according to supplementary note 4, wherein the obstacle factor assessing unit:
 can make multiple assessments regarding the presence or absence of visual or auditory abnormalities, the presence or absence of mental abnormality in the subject, and the compatibility with the specific person, and
 for assessment of obstacle factors, assesses which of the multiple assessments causes the obstacle factors for the subject.

(Supplementary Note 6)

The subject condition assessing apparatus according to supplementary note 4, wherein the stimulus generator repeats an operation of generating any of the first to third stimuli during a predetermined time period, and subsequently generating a different stimulus from among the first to third stimuli, at least until three of the first to third stimuli are generated.

(Supplementary Note 7)

The subject condition assessing apparatus according to any one of supplementary notes 1 to 6, wherein the synchronization analysis unit makes assessment based on whether or not the percentage of synchronization of the presence or absence of emotional expression is greater than or equal to a predetermined value during the stimulus generating period and the stimulus pause period.

The subject condition assessing apparatus of supplementary note 7 includes cases where the number of times the stimulus is generated is fixed and the number of synchronizations is greater than or equal to a predetermined number.

(Supplementary Note 8)

The subject condition assessing apparatus according to any one of supplementary notes 1 to 7, wherein the first stimulus is a sensory stimulus whose generation is recognized by visual or auditory stimulation.

(Supplementary Note 9)

The subject condition assessing apparatus according to any one of supplementary notes 3 to 8, wherein the second stimulus is a cognitive stimulus associated with cognition of predetermined information.

The invention claimed is:

1. An emotion assessment apparatus comprising a processor and a memory storing instructions that, when executed, cause the processor to:
    detect heartbeat information including the heart rate of a subject,
    assess whether the emotion of the subject is a negative emotion or a positive emotion based on the heartbeat information,
    count the number of heart rate variations within a predetermined time period, the heart rate variations being transitions from a state in which the heart rate is below the average heart rate to a state in which the heart rate is greater than or equal to the average heart rate and being with heart rate increase greater than or equal to a predetermined value,
    assess the mental state of the subject based on the number of heart rate variations and using the assessment results of the emotion of the subject to assess the mental state, and
    output the assessment results of the mental state of the subject,
    wherein the mental state of the subject includes at least one of a stable state, a surprised state, an emotionally moved state or an angry state.

2. The emotion assessment apparatus according to claim 1, wherein the instructions further cause the processor to photograph the face of the subject, and:
    detect heartbeat information based on changes in image data acquired by photographing the face of the subject.

3. The emotion assessment apparatus according to claim 1, wherein:
    the mental state includes a first mental state that can be assessed based on the number of heart rate variations regardless of whether the emotion is positive or negative, and a second mental state that can be assessed based on whether the emotion is positive or negative and on the number of heart rate variations, and
    the instructions further cause the processor to use the assessment results of the emotion of the subject at least when assessing the second mental state.

4. The emotion assessment apparatus according to claim 1, wherein:
    the predetermined time period is repeatedly set, and
    the instructions further cause the processor to perform assessment for each predetermined time period.

5. The emotion assessment apparatus according to claim 2, wherein the instructions further cause the processor to photograph faces of multiple subjects,
    identify each face from the screen on which the multiple subjects are displayed and identify measuring locations for each identified face, and
    acquire heartbeat information based on changes in the images at the measuring location for each face.

6. The emotion assessment apparatus according to claim 1, wherein:
    the subjects are students attending a lecture, and
    the instructions further cause the processor to assess whether or not the students are in the optimal mental state for attending the lecture, based on the number of heart rate variations and the assessment results of the emotion of the students.

7. The emotion assessment apparatus according to claim 1, wherein:
    the instructions further cause the processor to
    generate first stimuli being recognized in a sensory manner either visually or audibly when generated, second stimuli with informational content, the informational content being understood either visually or audibly, and third stimuli including at least one of an image or voice of a specific person, and
    repeatedly generate the same type of stimuli during multiple previously established periods with intervening a pause period, and
    assess the mental state of the subject at least during the multiple previously established periods.

8. The emotion assessment apparatus according to claim 1, wherein the negative emotions are emotions felt by the subject when the subject is in at least one condition of brain fatigue, anxiety or depression.

9. The emotion assessment apparatus according to claim 1, wherein the instructions further cause the processor to assess that the mental state is a surprised state when the number of heart rate variations is one time.

10. The emotion assessment apparatus according to claim 1, wherein the instructions further cause the processor to assess that the mental state is an emotionally moved state when the number of heart rate variations is multiple times and the emotion of the subject is a positive emotion.

11. The emotion assessment apparatus according to claim 1, wherein the instructions further cause the processor to assess that the mental state is an angry state when the number of heart rate variations is multiple times and the emotion of the subject is a negative emotion.

12. The emotion assessment apparatus according to claim 1, wherein the instructions further cause the processor to assess that the mental state is a stable state when the number of heart rate variations is zero times and a state in which the heart rate is below the average heart rate has been maintained during the predetermined time period.

13. The emotion assessment apparatus according to claim 1, wherein the instructions further cause the processor to assess that the mental state is an emotion-unassessable state when the number of heart rate variations is zero times and a state in which the heart rate is greater than or equal to the average heart rate during the predetermined time period, the emotion-unassessable state in which the mental state cannot be assessed.

14. A computer-readable non-transitory storage media storing an emotion assessment program causing a computer to perform a process, the process comprising:
    detecting heartbeat information including the heart rate of a subject;
    assessing whether the emotion of the subject is a negative emotion or a positive emotion based on the heartbeat information;
    counting the number of heart rate variations within a predetermined time period, the heart rate variations being transitions from a state in which the heart rate is below the average heart rate to a state in which the heart rate is greater than or equal to the average heart rate and being with heart rate increase greater than or equal to a predetermined value;

assessing the mental state of the subject based on the number of heart rate variations, and using the assessment results of the emotion of the subject to assess the mental state; and outputting the assessment results of the mental state of the subject, wherein the mental state of the subject includes at least one of a stable state, a surprised state, an emotionally moved state or an angry state.

15. An emotion assessment method comprising:

detecting heartbeat information including the heart rate of a subject, assessing whether the emotion of the subject is a negative emotion or a positive emotion based on the heartbeat information, counting the number of heart rate variations within a predetermined time period, the heart rate variations being transitions from a state in which the heart rate is below the average heart rate to a state above the average heart rate and with heart rate increase greater than or equal to a predetermined value, assessing the mental state of the subject based on the number of heart rate variations, and using the assessment results of the emotion of the subject to assess the mental state, and outputting the assessment results of the mental state of the subject, wherein the mental state of the subject includes at least one of a stable state, a surprised state, an emotionally moved state or an angry state.

* * * * *